United States Patent
Molteni et al.

(10) Patent No.: US 9,102,671 B2
(45) Date of Patent: Aug. 11, 2015

(54) COMPOUNDS AND COMPOSITIONS AS TRK INHIBITORS

(75) Inventors: Valentina Molteni, San Diego, CA (US); Yi Fan, San Diego, CA (US); Jon Loren, San Diego, CA (US); Jeffrey M. Smith, San Diego, CA (US); Brenton T. Flatt, San Diego, CA (US)

(73) Assignee: Novartis AG, Basel (CH)

( * ) Notice: Subject to any disclaimer, the term of this patent is extended or adjusted under 35 U.S.C. 154(b) by 84 days.

(21) Appl. No.: 14/000,578

(22) PCT Filed: Feb. 23, 2012

(86) PCT No.: PCT/US2012/026377
§ 371 (c)(1),
(2), (4) Date: Aug. 20, 2013

(87) PCT Pub. No.: WO2012/116217
PCT Pub. Date: Aug. 30, 2012

(65) Prior Publication Data
US 2013/0331397 A1    Dec. 12, 2013

Related U.S. Application Data

(60) Provisional application No. 61/446,572, filed on Feb. 25, 2011.

(51) Int. Cl.
*A61K 31/497* (2006.01)
*C07D 471/04* (2006.01)
*C07D 207/09* (2006.01)

(52) U.S. Cl.
CPC ............ *C07D 471/04* (2013.01); *C07D 207/09* (2013.01)

(58) Field of Classification Search
None
See application file for complete search history.

(56) References Cited

FOREIGN PATENT DOCUMENTS

| WO | WO2009140128 | | 11/2009 |
|---|---|---|---|
| WO | WO 2009140128 A2 | * | 11/2009 |
| WO | WO2010048314 | | 4/2010 |
| WO | WO2012034091 | | 3/2012 |

OTHER PUBLICATIONS

Claude J. Rogers et al: "Hammett Correlation of Nornicotine Analogues in the Aqueous Aldol Reaction: Implications for Green Organocatalysis", The Journal of Organic Chemistry, vol. 70, No. 9, Apr. 1, 2005, pp. 3705-3708.

Min Shi et al: "Gold(I)-Catalyzed Domino Ring-Opening Ring Closing Hydroamination of Methylenecyclopropanes (MCPs) with Sulfonamides: Facile Preparation of Pyrrolidine Derivatives", Organic Letters, vol. 8, No. 18, Aug. 1, 2006, pp. 4043-4046.

R. Karl Dieter et al: "Halogen- and N-Haloimide-Promoted Homo- and Heterocoupling of a-(N-Carbamoyl) alkylcuprates and a-(Alkoxy)alkylcuprates", The Journal of Organic Chemistry, vol. 69, No. 8, Apr. 1, 2004, pp. 2867-2870.

Ki Hwan Kim et al: "Quantitative structure-activity relationships of nicotine analogues as neuronal nicotinic acetylcholine receptor ligands", Bioorganic & Medicinal Chemistry, vol. 4, No. 12, Jan. 1, 1996, p. 2211.

* cited by examiner

*Primary Examiner* — Jeffrey S Lundgren
*Assistant Examiner* — Tori M Strong
(74) *Attorney, Agent, or Firm* — The Genomics Institute of the Novartis Research Foundation; Daniel E. Raymond

(57) ABSTRACT

The invention provides compounds, pharmaceutical compositions comprising such compounds and methods of using such compounds to treat or prevent diseases or disorders associated with abnormal or deregulated TRK kinase activity.

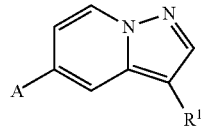

Formula (I)

wherein:
A is

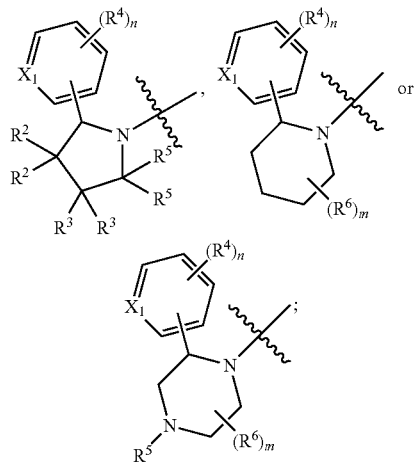

$X_1$ is CH or N;

19 Claims, No Drawings

COMPOUNDS AND COMPOSITIONS AS TRK INHIBITORS

CROSS-REFERENCE TO RELATED APPLICATIONS

This application is a 371 U.S. national phase application of international application number PCT/US2012/026377 filed 23 Feb. 2012, which application claims the benefit of priority under 35 U.S.C. §119(e) to U.S. Provisional Patent Application No. 61/446,572, filed 25 Feb., 2011. The disclosures of which are incorporated herein by reference in its entirety and for all purposes.

FIELD OF THE INVENTION

The invention relates to protein kinase inhibitors, and methods of using such compounds.

BACKGROUND OF THE INVENTION

Protein kinases (PK) are a large set of structurally related phosphoryl transferases having highly conserved structures and catalytic functions. Protein kinases are enzymatic components of the signal transduction pathways which catalyze the transfer of the terminal phosphate from ATP to the hydroxy group of tyrosine, serine and/or threonine residues of proteins, and are therefore categorized into families by the substrates they phosphorylate: Protein Tyrosine Kinases (PTK), and Protein Serine/Threonine Kinases.

Protein kinases play a critical role in the control of cell growth and differentiation and are responsible for the control of a wide variety of cellular signal transduction processes, wherein protein kinases are key mediators of cellular signals leading to the production of growth factors and cytokines. The overexpression or inappropriate expression of normal or mutant protein kinases plays a significant role in the development of many diseases and disorders including, central nervous system disorders such as Alzheimer's, inflammatory disorders such as arthritis, bone diseases such as osteoporosis, metabolic disorders such as diabetes, blood vessel proliferative disorders such as angiogenesis, autoimmune diseases such as rheumatoid arthritis, ocular diseases, cardiovascular disease, atherosclerosis, cancer, thrombosis, psoriasis, restenosis, schizophrenia, pain sensation, transplant rejection and infectious diseases such as viral, and fungal infections.

Examples of protein-tyrosine kinases include, but are not limited to, Irk, IGFR-1, Syk, Zap-70, Bmx, Btk, CHK (Csk homologous kinase), CSK (C-terminal Src Kinase), Itk-1, Src (c-Src, Lyn, Fyn, Lck, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-I or c-MET), PDGFR (α and β), Tie-1, Tie-2 (also Tek-1 or Tek), VEGFR1 (also FLT-1), VEGFR2 (also KDR), FLT-3, FLT-4, c-KIT, JAK1, JAK2, JAK3, TYK2, LOK, RET, TRKA, TRKB, TRKC, PYK2, ALK (Anaplastic Lymphoma Kinase), EPHA (1-8), EPHB (1-6), RON, Ros, Fes, Fer or EPHB4 (also EPHB4-1).

Examples of protein-serine/threonine kinases include, but are not limited to, Ark, ATM (1-3), CamK (1-IV), CamKK, Chk1 and 2 (Checkpoint kinases), CK1, CK2, Erk, IKK-I (also IKK-α or CHUK), IKK-2 (also IKK-β), Ilk, Jnk (1-3), LimK (1 and 2), MLK3Raf (A, B and C), CDK (1-10), PKC (including all PKC subtypes), Plk (1-3), NIK, Pak (1-3), PDK1, PKR, RhoK, RIP, RIP-2, GSK3 (α and β), PKA, P38, Erk (1-3), PKB (including all PKB subtypes) (also AKT-1, AKT-2, AKT-3 or AKT3-1), IRAK1, FRK, SGK, TAK1 or Tp1-2 (also COT).

SUMMARY OF THE INVENTION

Provide herein are compounds and pharmaceutical compositions thereof, which are useful as inhibitors of TRKA, TRKB and/or TRKC kinases. Various embodiments of the invention are described herein. It will be recognized that features specified in each embodiment may be combined with other specified features to provide further embodiments.

In one aspect, the present invention provides compounds having Formula (I), and the pharmaceutically acceptable salts, pharmaceutically acceptable solvates (e.g. hydrates), the N-oxide derivatives, protected derivatives, individual stereoisomers and mixture of stereoisomers thereof:

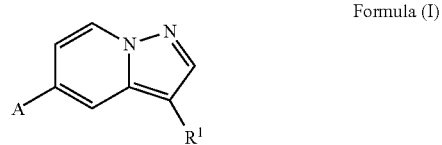

Formula (I)

wherein:
A is

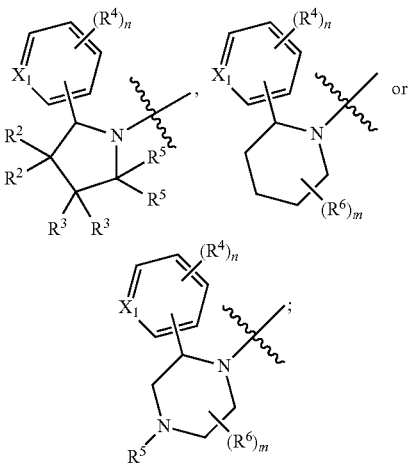

$X_1$ is CH or N;
$R^1$ is —C(O)NH$_2$, —C(O)N(R$^7$)$_2$, —C(O)N(R$^8$)$_2$, —NR$^7$C(O)R$^8$, —NR$^7$C(O)N(R$^7$)$_2$, —NR$^7$C(O)N(R$^8$)$_2$, —NR$^7$C(O)N(R$^9$)$_2$; —C(O)OR$^7$, —NR$^7$C(O)OR$^7$, —NR$^7$C(O)OR$^8$, —C(O)NR$^7$R$^8$, —C(O)NR$^7$C(O)OR$^7$, —C(O)NR$^7$C(O)NH$_2$, —C(O)NR$^7$C(O)N(R$^7$)$_2$ or H;
each $R^2$ is independently selected from H and $C_1$-$C_6$alkyl;
each $R^3$ is independently selected from H, $C_1$-$C_6$alkyl, —CN, —C(O)N(R$^7$)$_2$, —OR$^7$ and halo, or the two $R^3$ together with the C atom they are attached form a cyclopropyl group spiro attached to the pyrrolidine;
or a $R^2$ and a $R^3$ together with the C atom they are attached form a cyclopropyl ring fused to the pyrrolidine;
each $R^4$ is independently selected from H, halo, —OR$^7$, $C_1$-$C_6$alkyl, $C_1$-$C_6$alkyl substituted with 1-3 halo, $C_1$-$C_6$alkoxy substituted with 1-3 halo, —CN and —C(O)N(R$^7$)$_2$;

each $R^5$ is independently selected from H and $C_1$-$C_6$alkyl;
each $R^6$ is independently selected from H, $C_1$-$C_6$alkyl, —CN, —$OR^7$ and halo;
each $R^7$ is independently selected from H, $C_1$-$C_6$alkyl or $C_1$-$C_6$alkyl substituted with 1-3 —OH;
each $R^8$ is independently selected from H, $C_1$-$C_6$alkyl, phenyl, benzyl, phenyl substituted with 1-3 groups independently selected from $R^6$, benzyl substituted with 1-3 groups independently selected from $R^6$, an unsubstituted 5-6 membered heterocycloalkyl having 1 to 2 heteroatoms independently selected from O and N, a 5-6 membered heterocycloalkyl having 1 to 2 heteroatoms independently selected from O and N which is substituted with 1-3 groups independently selected from $R^6$, an unsubstituted $C_3$-$C_6$cycloalkyl, a $C_3$-$C_6$cycloalkyl substituted with 1-3 groups independently selected from $R^6$, an unsubstituted 5-6 membered heteroaryl having 1 to 2 heteroatoms independently selected from O and N, a 5-6 membered heteroaryl having 1 to 2 heteroatoms independently selected from O and N which is substituted with 1-3 groups independently selected from $R^6$;
each $R^9$ is a $C_1$-$C_6$alkyl and together with the N atom they are attached form an unsubstituted 5-6 membered heterocycloalkyl or a 5-6 membered heterocycloalkyl substituted with 1-3 groups independently selected from $R^6$.
m is 0, 1, 2, 3 or 4, and
n is 0, 1 or 2.

In certain embodiments, such compounds of Formula (I) A is

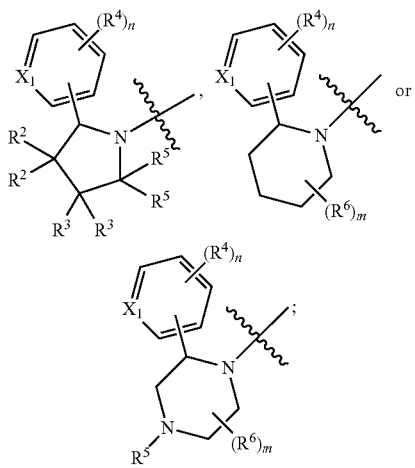

$X_1$ is CH or N;
$R^1$ is —C(O)NH$_2$, —C(O)N($R^7$)$_2$, —C(O)N($R^8$)$_2$, —NR$^7$C(O)R$^8$, —NR$^7$C(O)N($R^7$)$_2$, —NR$^7$C(O)N($R^8$)$_2$, —NR$^7$C(O)N($R^9$)$_2$; —C(O)OR$^7$—, —NR$^7$C(O)OR$^7$, —C(O)NR$^7$C(O)OR$^7$, —C(O)NR$^7$C(O)NH$_2$, —C(O)NR$^7$C(O)N($R^7$)$_2$ or H;
each $R^2$ is independently selected from H and $C_1$-$C_6$alkyl;
each $R^3$ is independently selected from H, $C_1$-$C_6$alkyl, —CN, —$OR^7$ and halo, or the two $R^3$ together with the C atom they are attached form a cyclopropyl group spiro attached to the pyrrolidine;
or a $R^2$ and a $R^3$ together with the C atom they are attached form a cyclopropyl ring fused to the pyrrolidine;
each $R^4$ is independently selected from H, halo, —$OR^7$, $C_1$-$C_6$alkyl, $C_1$-$C_6$alkyl substituted with 1-3 halo, $C_1$-$C_6$alkoxy substituted with 1-3 halo, —CN and —C(O)N($R^7$)$_2$;

each $R^5$ is independently selected from H and $C_1$-$C_6$alkyl;
each $R^6$ is independently selected from H, $C_1$-$C_6$alkyl, —CN, —$OR^7$ and halo;
each $R^7$ is independently selected from H, $C_1$-$C_6$alkyl or $C_1$-$C_6$alkyl substituted with 1-3 —OH;
each $R^8$ is independently selected from H, $C_1$-$C_6$alkyl, phenyl, phenyl substituted with 1-3 groups independently selected from $R^6$, an unsubstituted 5-6 membered heterocycloalkyl having 1 to 2 heteroatoms independently selected from O and N, a 5-6 membered heterocycloalkyl having 1 to 2 heteroatoms independently selected from O and N which is substituted with 1-3 groups independently selected from $R^6$, an unsubstituted $C_3$-$C_6$cycloalkyl, a $C_3$-$C_6$cycloalkyl substituted with 1-3 groups independently selected from $R^6$, an unsubstituted 5-6 membered heteroaryl having 1 to 2 heteroatoms independently selected from O and N, a 5-6 membered heteroaryl having 1 to 2 heteroatoms independently selected from O and N which is substituted with 1-3 groups independently selected from $R^6$;
each $R^9$ is a $C_1$-$C_6$alkyl and together with the N atom they are attached form an unsubstituted 5-6 membered heterocycloalkyl or a 5-6 membered heterocycloalkyl substituted with 1-3 groups independently selected from $R^6$;

m is 0, 1, 2, 3 or 4, and n is 0, 1 or 2.

In certain embodiments, such compounds of Formula (I) are compounds having the structure of Formula (II), Formula (III) or Formula (IV):

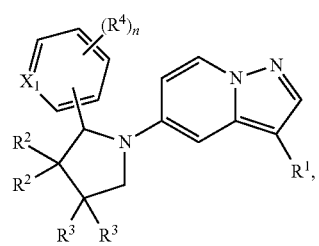

Formula (II)

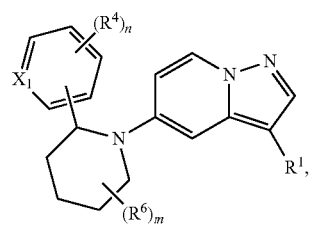

Formula (III)

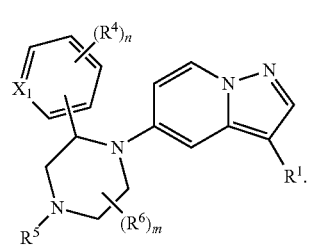

Formula (IV)

In certain embodiments, compounds of Formula (I) are compounds having the structure of Formula (II):

In certain embodiments, such compounds of Formula (I) are compounds having the structure of Formula (II-a) or Formula (II-b):

In certain embodiments, such compounds of Formula (I) are compounds having the structure of Formula (III-a) or Formula (III-b):

In certain embodiments, such compounds of Formula (I) are compounds having the structure of Formula (IV-a) or Formula (IV-b):

In certain embodiments, such compounds of Formula (I) are compounds having the structure of Formula (II-c):

In certain embodiments, such compounds of Formula (I) are compounds having the structure of Formula (II-d), Formula (II-e), Formula (II-f), Formula (II-g), Formula (II-h), Formula (II-i), Formula (II-j) or Formula (II-k):

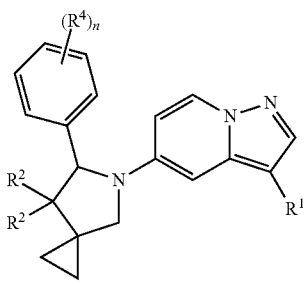
Formula (II-f)

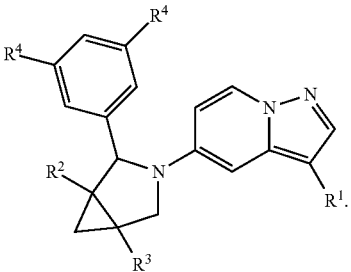
Formula (II-k)

In certain embodiments of such compounds of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b), each $R^7$ is independently selected from H, methyl and ethyl.

In certain embodiments of such compounds of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b), each $R^4$ is independently selected from H, F, —CN, —C(O)NH$_2$, —OCF$_3$, —OCHF$_2$ and —OCH$_2$F.

In certain embodiments of such compounds of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b), each $R^3$ is independently selected from H, —CN, —C(O)NH$_2$ and F, and wherein each $R^2$ is H.

In certain embodiments of such compounds of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b), each $R^3$ is independently selected from H and F, and wherein each $R^2$ is H.

In certain embodiments of such compounds of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b), $R^1$ is —C(O)NH$_2$, —C(O)N(R$^7$)$_2$ or —C(O)OR$^7$.

In certain embodiments of such compounds of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b), $R^1$ is —C(O)NH$_2$.

In certain embodiments compounds of Formula (I) are selected from 5-((2R,4S)-2-(3-cyano-5-fluorophenyl)-4-fluoropyrrolidin-1-yl)pyrazolo[1,5-a]pyridine-3-carboxamide; ethyl 5-((2R,4S)-4-fluoro-2-(3-fluorophenyl)pyrrolidin-1-yl)pyrazolo[1,5-a]pyridine-3-carboxylate; (R)-ethyl 5-(4,4-difluoro-2-(3-fluorophenyl)pyrrolidin-1-yl)pyrazolo[1,5-a]pyridine-3-carboxylate; 5-((2R,4S)-4-fluoro-2-(3-fluorophenyl)pyrrolidin-1-yl)pyrazolo[1,5-a]pyridine-3- carboxylic acid; (R)-5-(4,4-difluoro-2-(3-fluorophenyl) pyrrolidin-1-yl)pyrazolo[1,5-a]pyridine-3-carboxylic acid; 5-((2R,4S)-4-fluoro-2-(3-fluorophenyl)pyrrolidin-1-yl) pyrazolo[1,5-a]pyridine-3-carboxamide; (R)-5-(4,4-difluoro-2-(3-fluorophenyl)pyrrolidin-1-yl)pyrazolo[1,5-a]pyridine-3-carboxamide; ethyl 5-((2R,4S)-2-(3-cyano-5-fluorophenyl)-4-fluoropyrrolidin-1-yl)pyrazolo[1,5-a]pyridine-3-carboxylate; (R)-ethyl 5-(2-(3-cyano-5-fluorophenyl)-4,4-difluoropyrrolidin-1-yl)pyrazolo[1,5-a]pyridine-3-carboxylate; (R)-5-(2-(3-carbamoyl-5-fluorophenyl)-4,4-difluoropyrrolidin-1-yl)pyrazolo[1,5-a]pyridine-3-carboxamide, and (R)-5-(2-(3-cyano-5-fluorophenyl)-4,4-difluoropyrrolidin-1-yl)pyrazolo[1,5-a]pyridine-3-carboxamide.

In certain embodiments compounds of Formula (I) are selected from 5-[2-(3-fluorophenyl)piperidin-1-yl]pyrazolo[1,5-a]pyridine-3-carboxamide; 5-{2-[2-(trifluoromethyl)phenyl]pyrrolidin-1-yl}pyrazolo[1,5-a]pyridine-3-carboxamide; N-ethyl-5-[(2R,4S)-4-fluoro-2-(3-fluorophenyl) pyrrolidin-1-yl]pyrazolo[1,5-a]pyridine-3-carboxamide; 5-[(2R,4S)-4-fluoro-2-(3-fluorophenyl)pyrrolidin-1-yl]-N,N-dimethylpyrazolo[1,5-a]pyridine-3-carboxamide; N-tert-butyl-5-[(2R,4S)-4-fluoro-2-(3-fluorophenyl)pyrrolidin-1-yl]pyrazolo[1,5-a]pyridine-3-carboxamide; 5-[(2R,4S)-4-fluoro-2-(3-fluorophenyl)pyrrolidin-1-yl]-N-(2-hydroxyethyl)pyrazolo[1,5-a]pyridine-3-carboxamide; 5-(4,4-difluoro-2-{5-fluoro-2-[(propan-2-yl)carbamoyl] phenyl}pyrrolidin-1-yl)pyrazolo[1,5-a]pyridine-3-carboxamide; ethyl 5-[(2R,4S)-4-cyano-2-(3-fluorophenyl) pyrrolidin-1-yl]pyrazolo[1,5-a]pyridine-3-carboxylate; ethyl 5-[(2R,4S)-4-carbamoyl-2-(3-fluorophenyl)pyrrolidin-1-yl]pyrazolo[1,5-a]pyridine-3-carboxylate; benzyl N-{5-[(2R,4S)-4-fluoro-2-(3-fluorophenyl)pyrrolidin-1-yl]pyrazolo[1,5-a]pyridin-3-yl}carbamate; 5-[(2R,4S)-4-fluoro-2-(3-fluorophenyl)pyrrolidin-1-yl]-N-phenylpyrazolo[1,5-a] pyridine-3-carboxamide; {5-[(2R,4S)-4-fluoro-2-(3-fluorophenyl)pyrrolidin-1-yl]pyrazolo[1,5-a]pyridin-3-yl}urea; 5-[(2R,4R)-2-(3-fluorophenyl)-4-hydroxypyrrolidin-1-yl]pyrazolo[1,5-a]pyridine-3-carboxamide; 5-[(2R,4S)-4-cyano-2-(3-fluorophenyl) pyrrolidin-1-yl]pyrazolo[1,5-a]pyridine-3-carboxamide, and (3S,5R)-1-{3-carbamoylpyrazolo[1,5-a]pyridin-5-yl}-5-(3-fluorophenyl)pyrrolidine-3-carboxamide.

In certain embodiments compounds of Formula (I) is 5-((2R,4S)-2-(3-cyano-5-fluorophenyl)-4-fluoropyrrolidin-1-yl)pyrazolo[1,5-a]pyridine-3-carboxamide.

In certain embodiments compounds of Formula (I) is N-ethyl-5-[(2R,4S)-4-fluoro-2-(3-fluorophenyl)pyrrolidin-1-yl]pyrazolo[1,5-a]pyridine-3-carboxamide.

In certain embodiments compounds of Formula (I) is ethyl 5-[(2R,4S)-4-cyano-2-(3-fluorophenyl)pyrrolidin-1-yl] pyrazolo[1,5-a]pyridine-3-carboxylate.

In certain embodiments compounds of Formula (I) is ethyl 5-[(2R,4S)-4-carbamoyl-2-(3-fluorophenyl)pyrrolidin-1-yl] pyrazolo[1,5-a]pyridine-3-carboxylate.

Another aspect provided herein are pharmaceutical compositions comprising a therapeutically effective amount of a compound of Formula (I), Formula (II), Formula (III), Formula (IV), Formula (II-a), Formula (II-b), Formula (II-c), Formula (II-d), Formula (II-e), Formula (II-f), Formula (IH), Formula (II-g), Formula (II-h), Formula (II-i), Formula (II-j), Formula (II-k), Formula (III-a), Formula (III-b), Formula (IV-a) or Formula (IV-b) and a pharmaceutically acceptable carrier.

Another aspect provided herein are pharmaceutical compositions comprising a therapeutically effective amount of a compound of Formula (I) and a pharmaceutically acceptable carrier.

Another aspect provided herein are pharmaceutical compositions comprising a therapeutically effective amount of a compound of In certain embodiments of such compounds of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b) and a pharmaceutically acceptable carrier.

In certain embodiments of such pharmaceutical compositions, such pharmaceutical compositions are formulated for intravenous, oral administration, rectal administration inhalation, nasal administration, topical administration, ophthalmic administration or otic administration. In certain embodiments of such pharmaceutical compositions, the pharmaceutical composition is a tablet, a pill, a capsule, a liquid, an inhalant, a nasal spray solution, a suppository, a solution, an emulsion, an ointment, eye drop or ear drop.

Another aspect provided herein is the use of a compound of In certain embodiments of such compounds of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b) in the manufacture of a medicament for treating a TRK mediated disease or condition. In certain embodiments of such uses, the disease or condition is cancer, a proliferative diseases, a pain disorder, a dermatological disease, a metabolic disease, a muscle disease, a neurodegenerative disease, a neurological disease, an immunodeficiency disease, an immunologically-mediated disease, an autoimmune disease, an autoimmune mediated disease, a bone disease, an inflammatory disease, fibrosis, an ophthalmic disease, an infectious disease, a viral disease, wound repair, a respiratory disease, a pulmonary disease, a renal disease, a kidney disease, a liver disease, a cardiovascular disease, a vascular disease, heart disease, cell death and hyperplasiaan inflammatory disease. In certain embodiments of such uses, the disease or condition is asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, HIV or lupus. In certain embodiments of such uses, the disease or condition is condition is papillary thyroid carcinoma, pancreatic cancer, colon cancer, breast carcinoma, neuroblastoma, pain, cachexia, dermatitis or asthma.

Another aspect provided herein is the use of a compound of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b) in the manufacture of a medicament for treating a TRK mediated disease or condition. In certain embodiments of such uses, the disease or condition is cancer, a proliferative diseases, a pain disorder, a dermatological disease, a metabolic disease, a muscle disease, a neurodegenerative disease, a neurological disease, an immunodeficiency disease, an immunologically-mediated disease, an autoimmune disease, an autoimmune mediated disease, a bone disease, an inflammatory disease, fibrosis, an ophthalmic disease, an infectious disease, a viral disease, wound repair, a respiratory disease, a pulmonary disease, a renal disease, a kidney disease, a liver disease, a cardiovascular disease, a vascular disease, heart disease, cell death and hyperplasiaan inflammatory disease. In certain embodiments of such uses, the disease or condition is asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, HIV or lupus. In certain embodiments of such uses, the disease or condition is condition is papillary thyroid carcinoma, pancreatic cancer, colon cancer, breast carcinoma, neuroblastoma, pain, cachexia, dermatitis or asthma.

Another aspect provided herein is the use of a compound of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b) in the manufacture of a medicament for treating a TRK kinase-mediated disease or condition, wherein the disease or condition is papillary thyroid carcinoma, pancreatic cancer, colon cancer, breast carcinoma, neuroblastoma, pain, cachexia, dermatitis or asthma.

Another aspect provided herein are medicaments for treating a TRK mediated disease or condition in a patient wherein the medicament comprises a therapeutically effective amount of a compound of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b). In certain embodiments of such medicaments, the disease or condition is cancer, a proliferative diseases, a pain disorder, a dermatological disease, a metabolic disease, a muscle disease, a neurodegenerative disease, a neurological disease, an immunodeficiency disease, an immunologically-mediated disease, an autoimmune disease, an autoimmune mediated disease, a bone disease, an inflammatory disease, fibrosis, an ophthalmic disease, an infectious disease, a viral disease, wound repair, a respiratory disease, a pulmonary disease, a renal disease, a kidney disease, a liver disease, a cardiovascular disease, a vascular disease, heart disease, cell death and hyperplasiaan inflammatory disease. In certain embodiments of such medicaments, the disease or condition is asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, HIV or lupus. In certain embodiments of such medicaments, the disease or condition is condition is papillary thyroid carcinoma, pancreatic cancer, colon cancer, breast carcinoma, neuroblastoma, pain, cachexia, dermatitis or asthma.

Another aspect provided herein is a method for inhibiting a TRK kinase comprising administering to a system or a subject in need thereof, a therapeutically effective amount of a compound of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b), or pharmaceutically acceptable salts or pharmaceutical compositions thereof.

Another aspect provided herein is a method for treating a TRK kinase-mediated disease or condition, comprising administering to a system or subject in need of such treatment an effective amount of a compound of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b), or pharmaceutically acceptable salts or pharmaceutical compositions thereof, wherein the disease or condition is selected from cancer, pain, cachexia, a proli-ferative diseases, a pain disorder, a dermatological disease, a metabolic disease, a muscle disease, a neurodegenerative disease, a neurological disease, an immunodeficiency disease, an immunologically-mediated disease, an autoimmune disease, an autoimmune mediated disease, a bone disease, an inflammatory disease, fibrosis, an ophthalmic disease, an infectious disease, a viral disease, wound repair, a respiratory disease, a pulmonary disease, a renal disease, a kidney disease, a liver disease, a cardiovascular disease, a vascular disease, heart disease, cell death and hyperplasiaan inflammatory disease and wherein the compound is a compound of Formula (I). In certain embodiments of such methods the disease is asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, HIV, lupus, colon cancer or papillary thyroid carcinoma. In certain embodiments of such methods, the disease or condition is condition is papillary thyroid carcinoma, pancreatic cancer, colon cancer, breast carcinoma, neuroblastoma, pain, cachexia, dermatitis or asthma.

Another aspect provided herein is a method for treating a TRK kinase-mediated disease or condition, comprising administering to a system or subject in need of such treatment an effective amount of a compound of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b), or pharmaceutically acceptable salts or pharmaceutical compositions thereof, wherein the disease or condition is papillary thyroid carcinoma, pancreatic cancer, colon cancer, breast carcinoma, neuroblastoma, pain, cachexia, dermatitis or asthma.

Another aspect provided herein are methods for treating a cell-proliferative condition, comprising administering to a system or subject in need of such treatment an effective amount of a compound of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b), or pharmaceutically acceptable salts or pharmaceutical compositions thereof; wherein the cell-proliferative condition is lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer or gastrointestinal cancer. In certain embodiments of such methods, the cell-proliferative condition is anaplastic large-cell lymphoma, pancreatic cancer, ovarian cancer and lung cancer.

Another aspect provided herein are compounds Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b) for use in a the treatment of a disease wherein TRK kinase activity is implicated, wherein the disease is selected from cancer, pain, cachexia, a proliferative diseases, a pain disorder, a dermatological disease, a metabolic disease, a muscle disease, a neurodegenerative disease, a neurological disease, an immunodeficiency disease, an immunologically-mediated disease, an autoimmune disease, an autoimmune mediated disease, a bone disease, an inflammatory disease, fibrosis, an ophthalmic disease, an infectious disease, a viral disease, wound repair, a respiratory disease, a pulmonary disease, a renal disease, a kidney disease, a liver disease, a cardiovascular disease, a vascular disease, heart disease, cell death and hyperplasia, an inflammatory disease. In certain embodiments the disease is asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, HIV, lupus, colon cancer or papillary thyroid carcinoma. In certain embodiments the disease is papillary thyroid carcinoma, pancreatic cancer, colon cancer, breast carcinoma, neuroblastoma, pain, cachexia, dermatitis or asthma.

Another aspect provided herein are compounds of Formula (I), Formula (II), Formula (III), Formula (IV), Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (III-a), Formula (III-b), Formula (IV-a) or Formula (IV-b) for use in a the treatment of a disease wherein TRK kinase activity is implicated, wherein the disease is selected from papillary thyroid carcinoma, pancreatic cancer, colon cancer, breast carcinoma, neuroblastoma, pain, cachexia, dermatitis and asthma.

Another aspect provided herein are compounds of Formula (A), or pharmaceutically acceptable salt thereof:

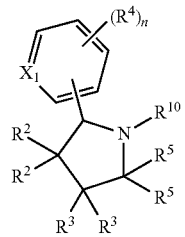

(Formula A)

wherein:
X$_1$ is CH or N;
each R$^2$ is independently selected from H and C$_1$-C$_6$alkyl;
each R$^3$ is independently selected from H, C$_1$-C$_6$alkyl, —CN, —C(O)N(R$^7$)$_2$, —OR$^7$ and halo, or the two R$^3$ together with the C atom they are attached form a cyclopropyl group spiro attached to the pyrrolidine;
or a R$^2$ and a R$^3$ together with the C atom they are attached form a cyclopropyl ring fused to the pyrrolidine;
each R$^4$ is independently selected from H, halo, —OR$^7$, C$_1$-C$_6$alkyl, C$_1$-C$_6$alkyl substituted with 1-3 halo, C$_1$-C$_6$alkoxy substituted with 1-3 halo, —CN and —C(O)N(R$^7$)$_2$;
each R$^5$ is independently selected from H;
R$^{10}$ is H or an amine protecting group, and
n is 0, 1 or 2.

In certain embodiments of such compounds of Formula (A), the compound of Formula (A) is a compound of Formula (B),

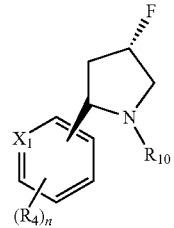

Formula (B)

wherein:
X$_1$ is CH or N;
each R$^4$ is independently selected from H, halo, —OR$^7$, C$_1$-C$_6$alkyl, C$_1$-C$_6$alkyl substituted with 1-3 halo, C$_1$-C$_6$alkoxy substituted with 1-3 halo, —CN and —C(O)N(R$^7$)$_2$;
R$^{10}$ is H or an amine protecting group, and
n is 0, 1 or 2.

In a certain embodiment of such compounds of Formula (B), the compound of Formula (B) is

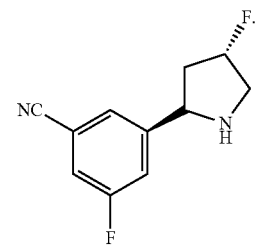

Another aspect provided herein are compounds of Formula (II), or pharmaceutically acceptable salt thereof:

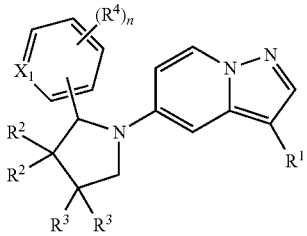

Formula (II)

prepared by a process comprising coupling in the presence of a catalyst an amine of Formula A

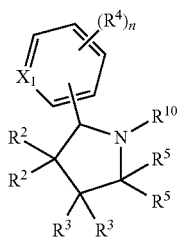

(Formula A)

with a compound of Formula C

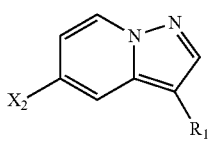

(Formula C)

wherein:
$X_1$ is CH or N;
$X_2$ is I, Br or Cl;
$R^1$ is —C(O)NH$_2$, —C(O)N(R$^7$)$_2$, —C(O)N(R$^8$)$_2$, —NR$^7$C(O)R$^8$, —NR$^7$C(O)N(R$^7$)$_2$, —NR$^7$C(O)N(R$^8$)$_2$, —NR$^7$C(O)N(R$^9$)$_2$; —C(O)OR$^7$, —NR$^7$C(O)OR$^7$, —NR$^7$C(O)OR$^8$, —C(O)NR$^7$R$^8$, —C(O)NR$^7$C(O)OR$^7$, —C(O)NR$^7$C(O)NH$_2$, —C(O)NR$^7$C(O)N(R$^7$)$_2$ or H;
each $R^2$ is independently selected from H and $C_1$-$C_6$alkyl;
each $R^3$ is independently selected from H, $C_1$-$C_6$alkyl, —CN, —C(O)N(R$^7$)$_2$, —OR$^7$ and halo, or the two $R^3$ together with the C atom they are attached form a cyclopropyl group spiro attached to the pyrrolidine;
or a $R^2$ and a $R^3$ together with the C atom they are attached form a cyclopropyl ring fused to the pyrrolidine;
each $R^4$ is independently selected from H, halo, —OR$^7$, $C_1$-$C_6$alkyl, $C_1$-$C_6$alkyl substituted with 1-3 halo, $C_1$-$C_6$alkoxy substituted with 1-3 halo, —CN and —C(O)N(R$^7$)$_2$;
each $R^5$ is independently selected from H;
each $R^6$ is independently selected from H, $C_1$-$C_6$alkyl, —CN, —OR$^7$ and halo;
each $R^7$ is independently selected from H, $C_1$-$C_6$alkyl or $C_1$-$C_6$alkyl substituted with 1-3 —OH;
each $R^8$ is independently selected from H, $C_1$-$C_6$alkyl, phenyl, benzyl, phenyl substituted with 1-3 groups independently selected from $R^6$, benzyl substituted with 1-3 groups independently selected from $R^6$, an unsubstituted 5-6 membered heterocycloalkyl having 1 to 2 heteroatoms independently selected from O and N, a 5-6 membered heterocycloalkyl having 1 to 2 heteroatoms independently selected from O and N which is substituted with 1-3 groups independently selected from $R^6$, an unsubstituted $C_3$-$C_6$cycloalkyl, a $C_3$-$C_6$cycloalkyl substituted with 1-3 groups independently selected from $R^6$, an unsubstituted 5-6 membered heteroaryl having 1 to 2 heteroatoms independently selected from O and N, a 5-6 membered heteroaryl having 1 to 2 heteroatoms independently selected from O and N which is substituted with 1-3 groups independently selected from $R^6$;
each $R^9$ is a $C_1$-$C_6$alkyl and together with the N atom they are attached form an unsubstituted 5-6 membered heterocycloalkyl or a 5-6 membered heterocycloalkyl substituted with 1-3 groups independently selected from $R^6$;
$R^{10}$ is H, and
m is 0, 1, 2, 3 or 4, and
n is 0, 1 or 2.

In certain embodiments of such compounds of Formula (II), the amine of Formula (A) is a compound of Formula (B),

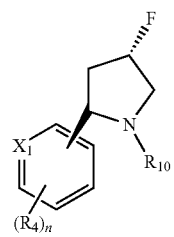

Formula (B)

wherein:
$X_1$ is CH or N;
each $R^4$ is independently selected from H, halo, —OR$^7$, $C_1$-$C_6$alkyl, $C_1$-$C_6$alkyl substituted with 1-3 halo, $C_1$-$C_6$alkoxy substituted with 1-3 halo, —CN and —C(O)N(R$^7$)$_2$;
$R^{10}$ is H, and
n is 0, 1 or 2.

In a certain embodiments of such compounds of Formula (B), the compound of Formula (B) is

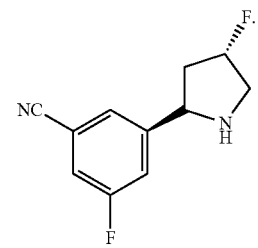

DETAILED DESCRIPTION OF THE INVENTION

Definitions

The term "alkyl," as used herein, refers to a fully saturated branched or unbranched, straight chain hydrocarbon. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. Representative examples of alkyl include, but are not limited to, methyl, ethyl, n-propyl, isopropyl, n-butyl, isobutyl, sec-butyl, tert-butyl, n-pentyl, isopentyl, neopentyl, hexyl, heptyl, octyl, nonyl, decyl and the like.

The term "cycloalkyl," as used herein, refers to a saturated monocyclic ring system or a saturated fused bicyclic ring system. As used herein, the terms "$C_3$-$C_5$ cycloalkyl", "$C_3$-$C_6$ cycloalkyl" and "$C_3$-$C_7$ cycloalkyl" refer to a cycloalkyl group wherein the saturated ring system contains at least 3, and at most 5, 6 or 7 carbon atoms. Non-limiting examples of cycloalkyl groups, as used herein, include cyclopropyl, cyclobutyl, cyclopentyl, cyclohexyl and cycloheptyl.

The term "halogen" or "halo," as used herein, refers to fluoro, chloro, bromo, and iodo.

The term "heteroaryl," as used herein, refers to monocyclic or fused bicyclic ring systems having a total of 5, 6, 9 or 10 ring members, wherein at least one ring member is a heteroatom selected from nitrogen, oxygen and sulfur. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[b]furyl, benzo[b]thienyl, cinnolinyl, furazanyl, furyl, imidazolyl, indolyl, indolizinyl, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, thiazolyl, thiadiazolyl, thienyl, triazinyl, triazolyl and tetrazolyl.

The term "heteroatom," as used herein, refers to an oxygen atom, sulfur atom, or nitrogen atom.

The term "heterocycloalkyl," as used herein, refers to a a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Non-limiting examples of heterocycloalkyl groups, as used herein, include morpholino, pyrrolidinyl, pyrrolidinyl-2-one, piperazinyl, piperazinyl-2-one, piperidinyl, piperidinylone, 1,3-dioxolanyl, imidazolidinyl, pyrazolidinyl, 1,4-dioxanyl, 1,4-dithianyl, thiomorpholinyl, azepanyl, hexahydro-1,4-diazepinyl, tetrahydrofuranyl, tetrahydrothienyl, tetrahydropyranyl, tetrahydrothiopyranyl, thioxanyl, azetidinyl, oxetanyl, thietanyl, oxepanyl, thiepanyl, dioxanyl, 1,3-dioxolanyl, dithianyl, dithiolanyl, imidazolidinyl, 3-azabicyclo[3.1.0]hexanyl, 2,5-diazabicyclo[2.2.1]heptane and 3-azabicyclo[4.1.0]heptanyl.

The term "hydroxyl," as used herein, refers to the group —OH.

The term "hydroxyalkyl," as used herein refers to an alkyl group as defined herein substituted with one or more hydroxyl group. Non-limiting examples of branched or straight chained "$C_1$-$C_6$ hydroxyalkyl groups as used herein include methyl, ethyl, propyl, isopropyl, isobutyl and n-butyl groups substituted with one or more hydroxyl groups.

The term "acceptable" with respect to a formulation, composition or ingredient, as used herein, means having no persistent detrimental effect on the general health of the subject being treated.

The term "administration" or "administering" of the subject compound means providing a compound of the invention and thereof to a subject in need of treatment.

As used herein, the term "a," "an," "the" and similar terms used in the context of the present invention (especially in the context of the claims) are to be construed to cover both the singular and plural unless otherwise indicated herein or clearly contradicted by the context.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to chemical compounds or agents that facilitate the incorporation of a compound described herein into cells or tissues.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "dermatological disorder," as used herein refers to a skin disorder. Such dermatological disorders include, but are not limited to, proliferative or inflammatory disorders of the skin such as, atopic dermatitis, dermatitis, bullous disorders, collagenoses, contact dermatitis, eczema, Kawasaki Disease, rosacea, Sjogren-Larsso Syndrome, and urticaria.

The term "diluent" as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "inhibit", "inhibition" or "inhibiting", as used herein, refers to the reduction or suppression of a given condition, symptom, or disorder, or disease, or a significant decrease in the baseline activity of a biological activity or process.

The term "inflammatory disorders", as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporarl arteritis); joints (arthritis: crystalline, osteo-, psoriatic, reactive, rheumatoid, Reiter's); gastrointestinal tract (Disease,); skin (dermatitis); or multiple organs and tissues (systemic lupus erythematosus).

The term "in need thereof, as used herein, refers to a treatment of a subject and whether such a subject would benefit biologically, medically or in quality of life from such treatment.

The term "isomers", as used herein, refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn- Ingold- Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The terms "neurogenerative disease" or "nervous system disorder," as used herein, refers to conditions that alter the structure or function of the brain, spinal cord or peripheral nervous system, including but not limited to Alzheimer's Disease, cerebral edema, cerebral ischemia, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica. The acronym "CNS" refers to disorders of the central nervous system (brain and spinal cord).

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable carrier", as used herein, includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "pharmaceutically acceptable salt", as used herein, refers to a salts that retain the biological effectiveness and properties of the compounds of this invention but do not cause significant irritation to an organism to which it is administered.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a coagent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The term "pharmaceutical composition", as used herein, refers to a mixture of a compound described herein with other chemical components, such as carriers, stabilizers, diluents, dispersing agents, suspending agents, thickening agents, and/or excipients.

The term "respiratory disease," as used herein, refers to diseases affecting the organs that are involved in breathing, such as the nose, throat, larynx, trachea, bronchi, and lungs.

Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

As used herein, the terms "salt" or "salts" refers to an acid addition or base addition salt of a compound of the invention. "Salts" include in particular "pharmaceutical acceptable salts". In many cases, the compounds of the present invention are capable of forming acid and/or base salts by virtue of the presence of amino and/or carboxyl groups or groups similar thereto.

The term "solvate," as used herein, refers to a molecular complex of variable stoichiometry formed by a compound of Formula (I) of the present invention (including pharmaceutically acceptable salts thereof) and one or more solvent molecules. Such solvent molecules are those commonly used in the pharmaceutical art, which are known to be innocuous to the recipient, e.g., water, ethanol, and the like. Non-limiting examples of a solvent are water, acetone, methanol, ethanol and acetic acid. The term "hydrate" refers to the complex where the solvent molecule is water.

The term "subject" or "patient", as used herein, encompasses mammals and non-mammals. Examples of mammals include, but are not limited to, primates, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like. In certain embodiments, the subject is a primate. In yet other embodiments, the subject is a human.

The term "therapeutically effective amount", as used herein, refers to an amount of a compound provided herein which, as compared to a corresponding subject who has not received such amount, will elicit the biological or medical response of a subject, for example, reduction or inhibition of an enzyme or a protein activity, or ameliorate symptoms, alleviate conditions, slow or delay disease progression, or prevent a disease. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by TRKA, TRKB and/or TRKC, or (ii) associated with TRKA, TRKB and/or TRKC activity, or (iii) characterized by activity (normal or abnormal) of TRKA, TRKB and/or TRKC; or (2) reducing or inhibiting the activity of TRKA, TRKB and/or TRKC; or (3) reducing or inhibiting the expression of TRKA, TRKB and/or TRKC. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of TRKA, TRKB and/or TRKC; or at least partially reducing or inhibiting the expression of TRKA, TRKB and/or TRKC.

The terms "treat", "treating" or "treatment," of any disease or disorder, as used herein, refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The terms "use" or "used," as used herein, are intended to include a compound of Formula (I) provided herein for use in the prophylactic and/or therapeutic treatment of one or more diseases provided herein, a method of use or a method of treatment comprising administering a compound of the Formula (I) to a person in need of such treatment in an effective amount for the prophylactic and/or therapeutic treat-ment of one or more diseases provided herein, the preparation or a method or preparation of a pharmaceutical formulation/preparation for use in the prophylactic and therapeutic treatment of one or more diseases provided herein, especially involving mixing a compound of the Formula (I) (as therapeutically active ingredient) with at least one pharmaceutically acceptable carrier material, including making it ready for use in such treatment (e.g. adding an instruction insert (e.g. package leaflet or the like), formulation, appropriate preparation, adaptation for specific uses, customizing and the like), and the use of a compound of the Formula (I) for such preparation, and/or all other prophylactic or therapeutic uses mentioned herein.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Other objects, features and advantages of the methods and compositions described herein will become apparent from the following detailed description. It should be understood, however, that the detailed description and the specific examples, while indicating specific embodiments, are given by way of illustration only.

The compound names provided herein were obtained using Chem Draw Ultra 12.0 (CambridgeSoft®) or JChem version 5.0.3 (ChemAxon).

Compounds

Provided herein are compounds, pharmaceutically acceptable salts, solvates, N-oxides and isomers thereof, which are inhibitrs of TRKA, TRKB and TRKC kinase activity. Also provided herein are compounds, pharmaceutically acceptable salts, solvates, N-oxides and isomers thereof, pharmaceutical compositions, pharmaceutical combinations for the treatment diseases or conditions/disorders associated with TRKA, TRKB and TRKC kinase activity. Also provided herein are methods of treaing diseases or conditions/disorders associated with TRKA, TRKB and TRKC kinase activity, wherein the method includes administration of a therapeutically effective amount of a compound provided herein, pharmaceutically acceptable salts, solvates, N-oxides and isomers thereof, and pharmaceutical compositions containing such pharmaceutically acceptable salts, solvates, N-oxides and isomers thereof.

In certain embodiments, such diseases and/or disorders include, but are not limited to, cancer, proliferative diseases, pain, dermatological diseases and/or disorders, metabolic diseases and/or disorders, muscle diseases and/or disorders, neurodegenerative diseases and/or disorders, neurological diseases and/or disorders, inflammatory diseases, fibrosis, infectious diseases, respiratory diseases and/or disorders, pulmonary diseases and/or disorders and hyperplasia.

Such cancer and proliferative diseases include, but are not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gastrointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome.

Such hematopoietic disorders include, but are not limited to, myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes.

Such hematological malignancies include, but are not limited to, leukemias, myeloid leukemias, hairy cell leukemia, lymphomas (non-Hodgkin's lymphoma), Hodgkin's disease (also called Hodgkin's lymphoma), and myeloma, including, but are not limited to, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma and acute promyelocytic leukemia (APL).

Such pain disorders include, but are not limited to, cancer-related pain, skeletal pain caused by tumor metastasis, osteoarthritis, visceral pain, inflammatory pain and neurogenic pain.

Such dermatological diseases and/or disorders include, but are not limited to, inflammatory or allergic conditions of the skin, dermatitis, eczema, psoriasis, atopic dermatitis, seborrhoeic dermatitis (Dandruff, Cradle cap), diaper rash, urushiol-induced contact dermatitis, contact dermatitis, erythroderma, lichen simplex chronicus, prurigo nodularis, itch, pruritus ani, nummular dermatitis, dyshidrosis, pityriasis alba, alopecia greata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, peritoneal and sub dermal adhesion and photoaging of the skin.

Such metabolic diseases and/or disorders and eating disorder include, but are not limited to, obesity and diabetes.

Such muscle diseases and/or disorders include, but are not limited to, muscular atrophies (e.g. disuse), muscular dystrophies (e.g. Duchenne's muscle dystrophy, Beckers muscle dystrophy, Limb-Girdle muscle dystrophy), sarcopenia, cachexia, wasting and Facioscapulohumeral dystrophy.

Such neurological diseases and/or disorders and neurodegenerative disorders include, but are not limited to, impaired neurological function and Alzheimer's disease.

Such inflammatory diseases and/or disorders include, but are not limited to, uveitis, atherosclerosis, atherogenesis, glomerulonephritis, Kawasaki disease, inflammatory responses, polymyositis, arthritis, neurological inflammation, chronic arthritis inflammation and osteoarthritis.

Such fibrosis diseases and/or disorders include, but are not limited to, extracellular matrix accumulation and fibrosis, scleroderma, fibrosclerosis, radiation-induced fibrosis, kidney fibrosis, lung fibrosis and liver fibrosis, haemochromatosis, primary biliary cirrhosis, restenosis, retroperitoneal fibrosis, mesenteric fibrosis, endometriosis and keloids.

Such ophthalmic/ocular diseases and/or disorders include, but are not limited to, proliferative vitreoretinopathy, ocular scarring, corneal scarring, ocular disorders, corneal wounds, conjunctivitis, keratoconjunctivitis sicca, and vernal conjunctivitis.

Such infectious diseases and/or disorders include, but are not limited to, Chagas disease.

Such respiratory diseases and/or disorders and pulmonary disorders include, but are not limited to, asthma, bronchial asthma, allergic asthma, intrinsic (non-allergic) asthma, extrinsic (allergic) asthma, exercise-induced asthma, drug-induced asthma (including aspirin and NSAID-induced) and dust-induced asthma, chronic obstructive pulmonary disease (COPD); chronic obstructive airways disease (COAD), chronic obstructive lung disease (COLD), bronchitis, chronic bronchitis, acute bronchitis, dyspnea, arachidic bronchitis, catarrhal bronchitis, croupus bronchitis, phthinoid bronchitis, rhinitis, acute rhinitis, chronic rhinitis, rhinitis medicamentosa, vasomotor rhinitis, perennial and seasonal allergic rhinitis, rhinitis nervosa (hay fever), inflammatory or obstructive airways diseases, pulmonary hypertension, acute lung injury, adult/acute respiratory distress syndrome (ARDS), pulmonary fibrosis, idiopathic pulmonary fibrosis, chronic obstructive pulmonary disease, pulmonary disease due to infectious or toxic agents, emphysema, pneumoconiosis, aluminosis, anthracosis, asbestosis, chalicosis, ptilosis, siderosis, silicosis, tabacosis, byssinosis, acute lung injury (ALI), hypereosinophilia, Löther's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, pulmonary hypertension, primary pulmonary hypertension (PPH), secondary pulmonary hypertension (SPH), familial PPH, sporadic PPH, precapillary pulmonary hypertension, pulmonary arterial hypertension (PAH), pulmonary artery hypertension, idiopathic pulmonary hypertension, thrombotic pulmonary arteriopathy (TPA), plexogenic pulmonary arteriopathy, functional classes I to IV pulmonary hypertension, and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, hypoxemia, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

The aforementioned compounds and pharmaceutically acceptable salts, solvates, N-oxides and isomers thereof, are compounds having structures according to Formula (I):

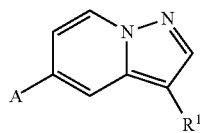

Formula (I)

wherein:
A is

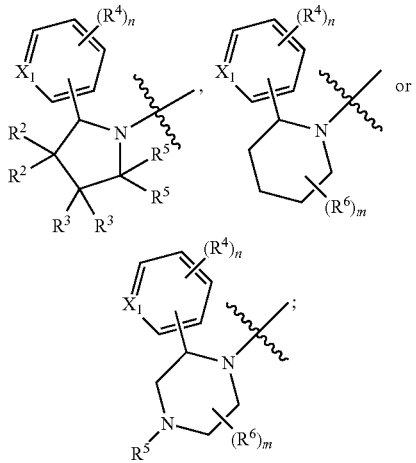

$X_1$ is CH or N;
$R^1$ is —C(O)NH$_2$, —C(O)N(R$^7$)$_2$, —C(O)N(R$^8$)$_2$, —NR$^7$C(O)R$^8$, —NR$^7$C(O)N(R$^7$)$_2$, —NR$^7$C(O)N(R$^8$)$_2$, —NR$^7$C(O)N(R$^9$)$_2$; —C(O)OR$^7$, —NR$^7$C(O)OR$^7$, —NR$^7$C(O)OR$^8$, —C(O)NR$^7$R$^8$, —C(O)NR$^7$C(O)OR$^7$, —C(O)NR$^7$C(O)NH$_2$, —C(O)NR$^7$C(O)N(R$^7$)$_2$ or H;
each $R^2$ is independently selected from H and $C_1$-$C_6$alkyl;
each $R^3$ is independently selected from H, $C_1$-$C_6$alkyl, —CN, —C(O)N(R$^7$)$_2$, —OR$^7$ and halo, or the two R$^3$ together with the C atom they are attached form a cyclopropyl group spiro attached to the pyrrolidine;
or a $R^2$ and a $R^3$ together with the C atom they are attached form a cyclopropyl ring fused to the pyrrolidine;
each $R^4$ is independently selected from H, halo, —OR$^7$, $C_1$-$C_6$alkyl, $C_1$-$C_6$alkyl substituted with 1-3 halo, $C_1$-$C_6$alkoxy substituted with 1-3 halo, —CN and —C(O)N(R$^7$)$_2$;
each $R^5$ is independently selected from H and $C_1$-$C_6$alkyl;
each $R^6$ is independently selected from H, $C_1$-$C_6$alkyl, —CN, —OR$^7$ and halo;
each $R^7$ is independently selected from H, $C_1$-$C_6$alkyl or $C_1$-$C_6$alkyl substituted with 1-3 —OH;

each $R^8$ is independently selected from H, $C_1$-$C_6$alkyl, phenyl, benzyl, phenyl substituted with 1-3 groups independently selected from R$^6$, benzyl substituted with 1-3 groups independently selected from R$^6$, an unsubstituted 5-6 membered heterocycloalkyl having 1 to 2 heteroatoms independently selected from O and N, a 5-6 membered heterocycloalkyl having 1 to 2 heteroatoms independently selected from O and N which is substituted with 1-3 groups independently selected from R$^6$, an unsubstituted $C_3$-$C_6$cycloalkyl, a $C_3$-$C_6$cycloalkyl substituted with 1-3 groups independently selected from R$^6$, an unsubstituted 5-6 membered heteroaryl having 1 to 2 heteroatoms independently selected from O and N, a 5-6 membered heteroaryl having 1 to 2 heteroatoms independently selected from O and N which is substituted with 1-3 groups independently selected from R$^6$;
each $R^9$ is a $C_1$-$C_6$alkyl and together with the N atom they are attached form an unsubstituted 5-6 membered heterocycloalkyl or a 5-6 membered heterocycloalkyl substituted with 1-3 groups independently selected from R$^6$;
m is 0, 1, 2, 3 or 4,
n is 0, 1 or 2.

In certain embodiments of the aforementioned compounds and pharmaceutically acceptable salts, solvates, N-oxides and isomers thereof, having structures according to Formula (I):
A is

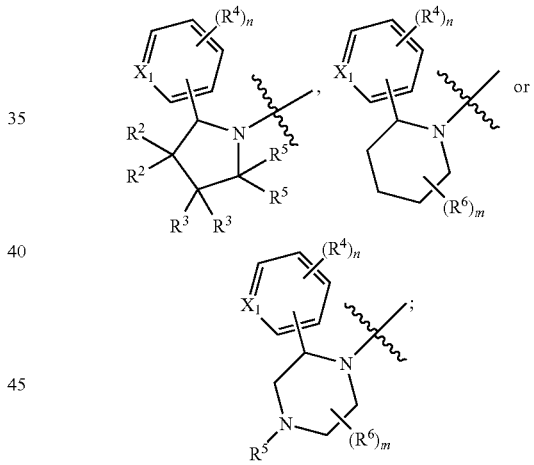

$X_1$ is CH or N;
$R^1$ is —C(O)NH$_2$, —C(O)N(R$^7$)$_2$, —C(O)N(R$^8$)$_2$, —NR$^7$C(O)R$^8$, —NR$^7$C(O)N(R$^7$)$_2$, —NR$^7$C(O)N(R$^8$)$_2$, —NR$^7$C(O)N(R$^9$)$_2$; —C(O)OR$^7$, —NR$^7$C(O)OR$^7$, —C(O)NR$^7$C(O)OR$^7$, —C(O)NR$^7$C(O)NH$_2$, —C(O)NR$^7$C(O)N(R$^7$)$_2$ or H;
each $R^2$ is independently selected from H and $C_1$-$C_6$alkyl;
each $R^3$ is independently selected from H, $C_1$-$C_6$alkyl, —CN, —OR$^7$ and halo, or the two R$^3$ together with the C atom they are attached form a cyclopropyl group spiro attached to the pyrrolidine;
or a $R^2$ and a $R^3$ together with the C atom they are attached form a cyclopropyl ring fused to the pyrrolidine;
each $R^4$ is independently selected from H, halo, —OR$^7$, $C_1$-$C_6$alkyl, $C_1$-$C_6$alkyl substituted with 1-3 halo, $C_1$-$C_6$alkoxy substituted with 1-3 halo, —CN and —C(O)N(R$^7$)$_2$;
each $R^5$ is independently selected from H and $C_1$-$C_6$alkyl;

each $R^6$ is independently selected from H, $C_1$-$C_6$alkyl, —CN, —$OR^7$ and halo;

each $R^7$ is independently selected from H, $C_1$-$C_6$alkyl or $C_1$-$C_6$alkyl substituted with 1-3 —OH;

each $R^8$ is independently selected from H, $C_1$-$C_6$alkyl, phenyl, phenyl substituted with 1-3 groups independently selected from $R^6$, an unsubstituted 5-6 membered heterocycloalkyl having 1 to 2 heteroatoms independently selected from O and N, a 5-6 membered heterocycloalkyl having 1 to 2 heteroatoms independently selected from O and N which is substituted with 1-3 groups independently selected from $R^6$, an unsubstituted $C_3$-$C_6$cycloalkyl, a $C_3$-$C_6$cycloalkyl substituted with 1-3 groups independently selected from $R^6$, an unsubstituted 5-6 membered heteroaryl having 1 to 2 heteroatoms independently selected from O and N, a 5-6 membered heteroaryl having 1 to 2 heteroatoms independently selected from O and N which is substituted with 1-3 groups independently selected from $R^6$;

each $R^9$ is a $C_1$-$C_6$alkyl and together with the N atom they are attached form an unsubstituted 5-6 membered heterocycloalkyl or a 5-6 membered heterocycloalkyl substituted with 1-3 groups independently selected from $R^6$;

m is 0, 1, 2, 3 or 4, n is 0, 1 or 2.

In certain embodiments of the aforementioned compounds and pharmaceutically acceptable salts, solvates, N-oxides and isomers thereof, having structures according to Formula (I) are compounds having the structure of Formula (II), Formula (III) or Formula (IV):

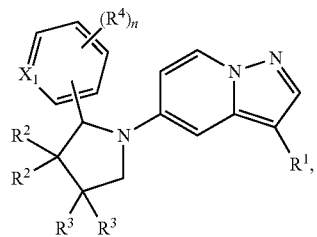

Formula (II)

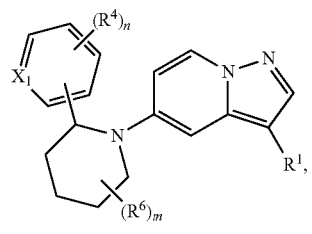

Formula (III)

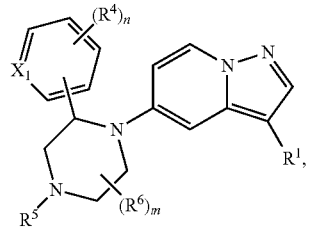

Formula (IV)

wherein n, $R^1$, $R^2$, $R^3$, $R^4$, $R^5$ and $R^6$ are as defined herein.

In certain embodiments of the aforementioned compounds and pharmaceutically acceptable salts, solvates, N-oxides and isomers thereof, having structures according to Formula (I) are compounds having the structure of Formula (II-a) or Formula (II-b):

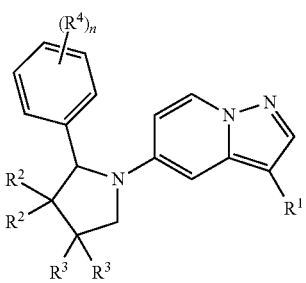

Formula (II-a)

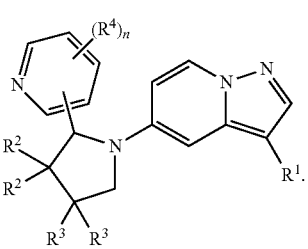

Formula (II-b)

wherein n, $R^1$, $R^2$, $R^3$ and $R^4$ are as defined herein.

In certain embodiments of the aforementioned compounds and pharmaceutically acceptable salts, solvates, N-oxides and isomers thereof, having structures according to Formula (I) are compounds having the structure of Formula (III-a) or Formula (III-b):

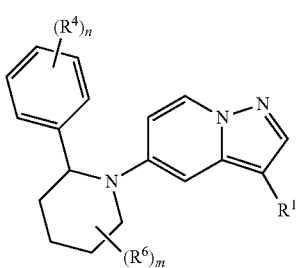

Formula (III-a)

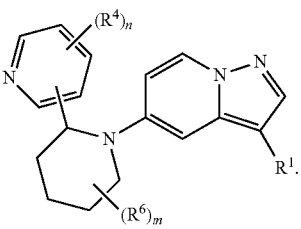

Formula (III-b)

In certain embodiments of the aforementioned compounds and pharmaceutically acceptable salts, solvates, N-oxides and isomers thereof, having structures according to Formula (I) are compounds having the structure of Formula (IV-a) or Formula (IV-b):

Formula (IV-a)

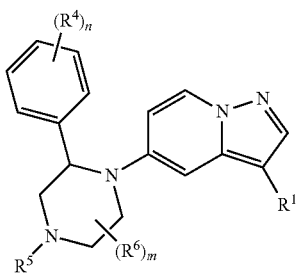

Formula (IV-b)

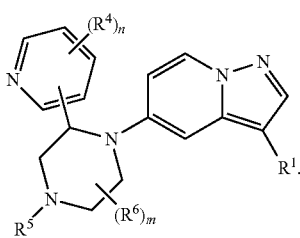

In certain embodiments of the aforementioned compounds and pharmaceutically acceptable salts, solvates, N-oxides and isomers thereof, having structures according to Formula (I) are compounds having the structure of Formula (II-c):

Formula (II-c)

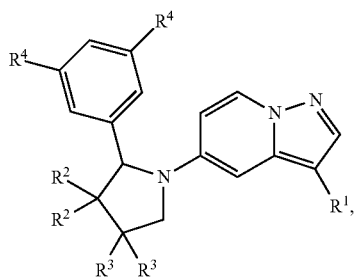

wherein $R^1$, $R^2$, $R^3$ and $R^4$ are as defined herein.

In certain embodiments of the aforementioned compounds and pharmaceutically acceptable salts, solvates, N-oxides and isomers thereof, having structures according to Formula (I) are compounds having the structure of Formula (II-d), Formula (II-e), Formula (II-f), Formula (II-g), Formula (II-h), Formula (II-i), Formula (II-j) or Formula (II-k):

Formula (II-d)

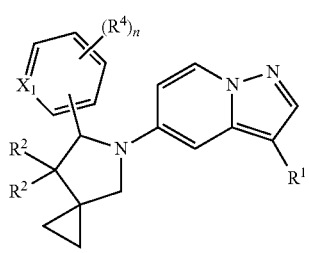

Formula (II-e)

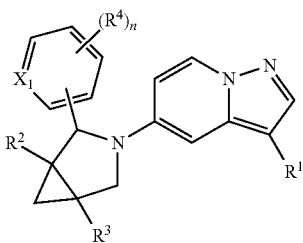

Formula (II-f)

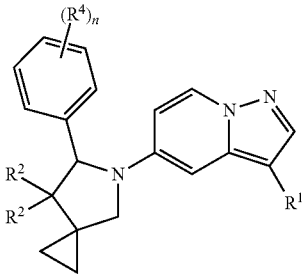

Formula (II-g)

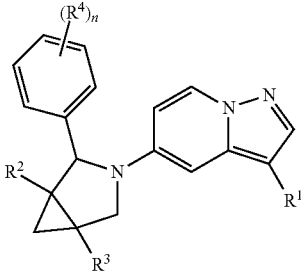

Formula (II-h)

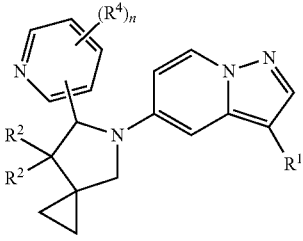

Formula (II-i)

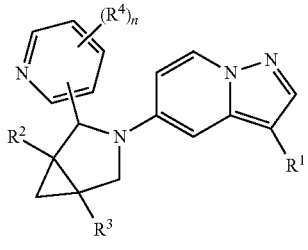

Formula (II-j)

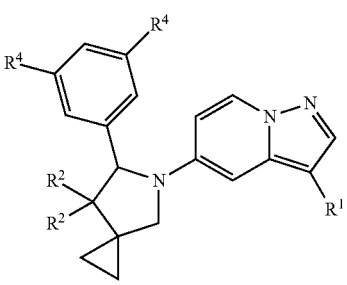

-continued

Formula (II-k)

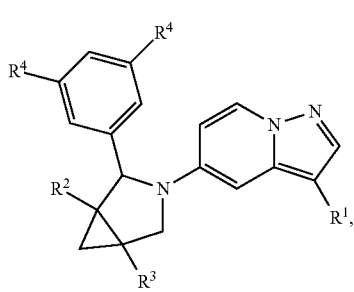

wherein n, $R^1$, $R^2$, $R^3$ and $R^4$ are as defined herein.

Unless specified otherwise, the term "compounds of the present invention" or "compounds provided herein", refers to compounds of Formula (I) and subformulae thereof (for example, compounds of Formula (II), of Formula (III), of Formula (IV), Formula (II-a), Formula (II-b), Formula (II-c), Formula (II-d), Formula (II-e), Formula (II-f), Formula (II-g), Formula (II-h), Formula (II-i), Formula (II-j) and Formula (II-k)), thereof, salts of the compound and/or, hydrates or solvates of the compounds, salts and/or, as well as all stereoisomers (including diastereoisomers and enantiomers), tautomers and isotopically labeled compounds (including deuterium substitutions), as well as inherently formed moieties (e.g., polymorphs, solvates and/or hydrates).

The compounds, pharmaceutically acceptable salts, solvates, N-oxides and isomers thereof, and pharmaceutical compositions provided herein also includes all suitable isotopic variations thereof. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number.

An isotopic variation of a compound of the invention or a pharmaceutically acceptable salt thereof is defined as one in which at least one atom is replaced by an atom having the same atomic number but an atomic mass different from the atomic mass usually found in nature.

Examples of isotopes that may be incorporated into the compounds of the invention include but are not limited to isotopes of hydrogen, carbon, nitrogen, oxygen, phosphorous, sulfur, fluorine, chlorine and iodine, such as $^2H$, $^3H$, $^{11}C$, $^{13}C$, $^{14}C$, $^{15}N$, $^{15}O$, $^{31}P$, $^{32}P$, $^{35}S$, $^{18}F$, $^{36}Cl$, and $^{125}I$, respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies.

Isotopically-labeled compounds of Formula (I) and pharmaceutically acceptable salts, solvates, N-oxides and isomers thereof, and pharmaceutical compositions provided herein are prepared by conventional procedures known to those skilled in the art by processes analogous to those described in the accompanying Examples and Preparations using appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the Formula (I). The concentration of such a heavier isotope, specifically deuterium, may be defined by the isotopic enrichment factor.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of Formula (I), that contain groups capable of acting as donors and/or acceptors for hydrogen bonds may be capable of forming co-crystals with suitable co-crystal formers. These co-crystals may be prepared from compounds of Formula (I) by known co-crystal forming procedures. Such procedures include grinding, heating, co-subliming, co-melting, or contacting in solution compounds of Formula (I) with the co-crystal former under crystallization conditions and isolating co-crystals thereby formed. Suitable co-crystal formers include those described in WO 2004/078163. Hence the invention further provides co-crystals comprising a compound of Formula (I).

Processes for Making Compounds of Formula (I)

General procedures for preparing compounds of Formula (I) are described in the Examples, infra. In the reactions described, reactive functional groups, for example hydroxyl, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry," John Wiley and Sons, 1991).

In certain embodiments, the compounds of Formula (I) described herein are prepared as a pharmaceutically acceptable acid addition salt by reacting the free base form of the compound of Formula (I) with a pharmaceutically acceptable organic acid or inorganic acid. In other embodiments, a pharmaceutically acceptable base addition salt of compounds of Formula (I) described herein is prepared by reacting the free acid form of the compound of Formula (I) with a pharmaceutically acceptable organic base or inorganic base. Alternatively, the salt forms of the compounds of Formula (I) described herein are prepared using salts of the starting materials or intermediates. In certain embodiments, the compounds of Formula (I) described herein are in the form of other salts including, but not limited to, oxalates and trifluoroacetates. In certain embodiments, hemisalts of acids and bases are formed, for example, hemisulphate and hem ical-cium salts.

The pharmaceutically acceptable organic acid or inorganic acids used to form pharmaceutically acceptable acid addition salts of compounds of Formula (I) include, but are not limited to, hydrofluoric acid, hydrochloric acid, hydrobromic acid, hydroiodic acid, nitric acid, sulfuric acid, phosphoric acid, formic acid, acetic acid, trifluoroacetic acid, propionic acid, butyric acid, caprylic acid, dichloroacetic acid, hippuric acid, lactic acid, citric acid, tartaric acid, malic acid, glycolic acid, gluconic acid, mandelic acid, maleic acid, oxalic acid, succinic acid, adipic acid, aspartic acid, fumaric acid, glutamic acid, malonic acid, sebacic acid, salicylic acid, hexanoic acid, benzoic acid, p-chloro-benzoic acid, nicotinic acid, diphenylacetic acid, triphenylacetic acid, o-hydroxybenzoic acid, p-hydroxybenzoic acid, 1-hydroxynaphthalene-2-carboxylic acid or 3-hydroxynaphthalene-2-carboxylic acid, sulfosalicylic acid, sulfonic acids, methanesulfonic acid, benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid and p-toluenesulfonic acid. Pharmaceutically acceptable solvates are generally hydrates.

Such pharmaceutically acceptable acid addition salts of compounds of Formula (I) include, but are not limited to, a hydrobromide, hydrochloride, sulfate, nitrate, succinate, maleate, formate, acetate, adipate, besylatye, camphorsulfonate, bicarbonate/carbonate, propionate, ethandisulfonate, fumarate, chlortheophyllonate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), hexanoate salt, bisulphate/sulphate, borate, camsylate, cyclamate, edisylate, esylate, gluceptate, gluconate, glucuronate, hexafluorophosphate, hibenzate, hydrochloride/chloride, hydrobromide/bromide, hydroiodide/iodide, isethionate, lactate, lactobionate, laurylsulfate, malate, malonate, mandelate, mesylate, methylsulphate, naphthylate, naphthoate, napsylate, nicotinate, octadecanoate, oleate, orotate, oxalate, palmitate, pamoate, phosphate/hydrogen phosphate/dihydrogen phosphate, pyroglutamate, polygalacturonate, propionate, saccharate, stearate, sulfosalicylate, tannate, tosylate, trifluoroacetate and xinofoate salts.

Such pharmaceutically acceptable base addition salt of a compound of Formula (I) include, but are not limited to, aluminium, ammonium, arginine, benzathine, calcium, choline, cholinate, diethanolamine, diethylamine, diolamine, glycine, lysine, magnesium, meglumine, olamine, potassium, sodium, tromethamine, ethanolamines, benzylamines, pyridine, benethamine, diethanolamine, 4-(2-hydroxy-ethyl) morpholine,1-(2-hydroxyethyl)pyrrolidine, N-methyl glutamine, piperazine, triethanol-amine, tromethamine and zinc salts.

In certain embodiments, the free acid or free base forms of the compounds of Formula (I) described herein are prepared from the corresponding base addition salt or acid addition salt from, respectively. For example a compound Formula (I) in an acid addition salt form is converted to the corresponding free base by treating with a stoichiometric amount of a suitable base (by way of example only, ammonium hydroxide, sodium hydroxide, calcium hydroxide, magnesium hydroxide, potassium hydroxide, sodium carbonate, calcium carbonate, magnesium carbonate, potassium carbonate, sodium bicarbonate, calcium bicarbonate, magnesium bicarbonate, potassium bicarbonate, or the like). For example, a compound of Formula (I) in a base addition salt form is converted to the corresponding free acid by treating with a stoichiometric amount of a suitable acid (by way of example only, hydrochloric acid). Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

In certain embodiments, the compounds of Formula (I) described herein in unoxidized form are prepared from N-oxides of compounds Formula (I) by treating with a reducing agent (by way of example only, sulfur, sulfur dioxide, triphenyl phosphine, lithium borohydride, sodium borohydride, phosphorus trichloride, tribromide, or the like) in a suitable inert organic solvent (by way of example only, acetonitrile, ethanol, aqueous dioxane, or the like) at 0 to 80° C.

Furthermore, the compounds of Formula (I) of the present invention, including their salts, can also be obtained in the form of their hydrates, or include other solvents used for their crystallization. The compounds of Formula (I) of the present invention may inherently or by design form solvates with pharmaceutically acceptable solvents (including water); therefore, it is intended that the invention embrace both solvated and unsolvated forms.

In certain embodiments, the compounds of Formula (I) described herein are prepared or formed, as solvates (e.g., hydrates). In certain embodiments, hydrates of compounds of Formula (I) are prepared by recrystallization from an aqueous/organic solvent mixture, using organic solvents such as dioxin, tetrahydrofuran or methanol.

The compounds of the present invention, including salts, hydrates and solvates thereof, may inherently or by design form polymorphs.

Depending on the choice of the starting materials and procedures, the compounds of Formula (I) can be present in the form of one of the possible isomers or as mixtures thereof, for example as pure optical isomers, or as isomer mixtures, such as racemates and diastereoisomer mixtures, depending on the number of asymmetric carbon atoms or geometric (cis or trans) isomers. The present invention is meant to include all such possible isomers, including racemic mixtures, diasteriomeric mixtures and optically pure forms.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any asymmetric atom (e.g., carbon or the like) of the compound(s) of Formula (I) provided herein can be present in racemic or enantiomerically enriched mixtures, for example the (R)-, (S)- or (R,S)-configuration. In certain embodiments, each asymmetric atom has at least 50% enantiomeric excess, at least 60 enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

In certain embodiments, the compounds of Formula (I) provided herein are prepared as a racemic mixture. In certain embodiments, the compounds of Formula (I) described herein are prepared as their individual stereoisomers.

Any resulting mixtures of isomers can be separated on the basis of the physicochemical differences of the constituents, into the pure or substantially pure geometric or optical isomers, diastereomers, racemates, for example, by chromatography and/or fractional crystallization. Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Optically active (R)- and (S)-isomers may be prepared using chiral synthons or chiral reagents, or resolved using conventional techniques. In certain embodiments, the compounds of Formula (I) provided herein are prepared as a racemic mixture and their individual stereoisomers are obtained using chiral chromatography, including, but not limited to, chiral liquid chromatogtaphy. In other embodiments, the compounds of Formula (I) described herein are prepared as their individual stereoisomers by reacting a racemic mixture of the compound with an optically active resolving agent to form a pair of diastereoisomeric compounds, separating the diastereomers and recovering the optically pure enantiomers. In certain embodiments, resolution of enantiomers is carried out using covalent diastereomeric derivatives of the compounds of Formula (I), or by using dissociable complexes (e.g., crystalline diastereomeric salts).

Diastereomers have distinct physical properties (e.g., melting points, boiling points, solubility, reactivity, etc.) and are readily separated by taking advantage of these dissimilarities. In certain embodiments, the diastereomers are separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

Compounds of Formula (I) are provided in substantially pure form. In certain embodiments compounds of Formula (I) are at least 60% pure. In certain embodiments compounds of Formula (I) are at least 75% pure. In certain embodiments compounds of Formula (I) are at 85% pure. In certain embodiments compounds of Formula (I) are at least 98% pure (% are on a weight for weight basis).

Substituents at atoms with unsaturated double bonds may, if possible, be present in cis- (Z)- or trans- (E)- form.

In certain embodiments, the compounds of Formula (I) described herein are prepared as protected derivatives using methods known to those of ordinary skill in the art. Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage). A detailed description of the techniques applicable to the creation of protecting groups and their removal can be found in T. W. Greene, "Protecting Groups in Organic Chemistry," $3^{rd}$ edition, John Wiley and Sons, Inc., 1999.

In certain embodimenst, salts of compounds of Formula (I) of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Compounds of Formula (I) of the present invention can made by processes described herein and as illustrated in the Examples. Non-limiting examples of synthetic schemes used to make compounds of Formula (I) described herein, or intermediates used to make compounds of Formula (I), are illustrated in reaction schemes (I)(XVI), wherein m, n, A, $X_1$, $R^1$, $R^2$, $R^3$, $R^4$, $R^5$, $R^6$, $R^7$, $R^8$ and $R^9$ are as defined herein.

Reaction scheme (I) illustrates the synthesis of certain compounds of Formula (I) by the coupling an amine intermediate with a halide containing intermediate in the presence of a base, a palladium catalyst and a ligand in a suitable solvent. By way of example only the palladium catalyst is tris(dibenzylideneacetone)dipalladium(0) (Pd$_2$(dba)$_3$), the ligand is xantphos, the base is Cs$_2$CO$_3$ and the solvent is 1,4-dioxane.

Reaction Scheme (I)

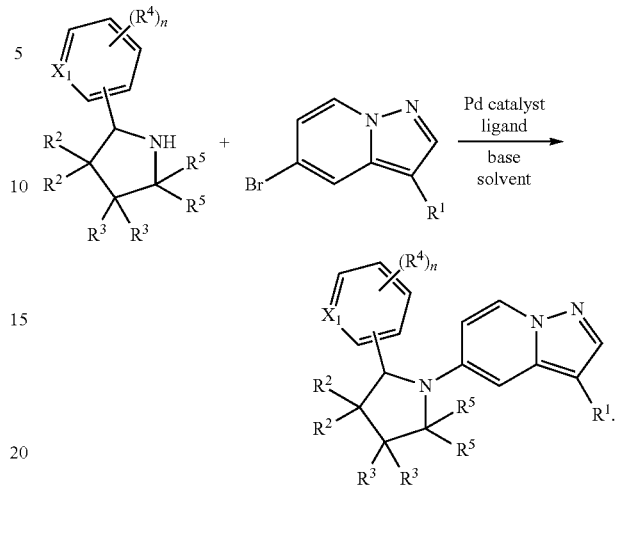

Reaction scheme (II) illustrates the synthesis of certain compounds of Formula (I) by the coupling an amine intermediate with a halide containing intermediate in the presence of a base, a palladium catalyst and a ligand in a suitable solvent. By way of example only the palladium catalyst is tris(dibenzylideneacetone)dipalladium(0) (Pd$_2$(dba)$_3$), the ligand is xantphos, the base is Cs$_2$CO$_3$ and the solvent is 1,4-dioxane.

Reaction Scheme (II)

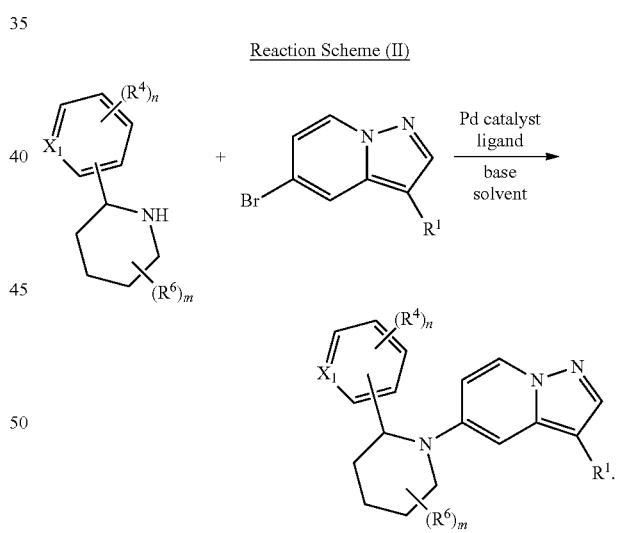

Reaction scheme (III) illustrates the synthesis of certain compounds of Formula (I) by the coupling an amine intermediate with a halide containing intermediate wherein R$_1$ is a protected amide. Again the coupling is in the presence of a base, a palladium catalyst and a ligand in a suitable solvent. By way of example only the palladium catalyst is tris(dibenzylideneacetone)dipalladium(0) (Pd$_2$(dba)$_3$), the ligand is xantphos, the base is Cs$_2$CO$_3$ and the solvent is 1,4-dioxane.

Reaction Scheme (III)

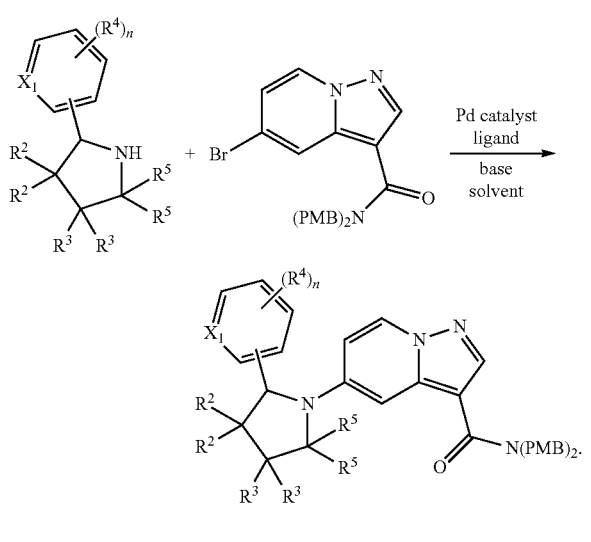

Reaction scheme (IV) illustrates the synthesis of certain compounds of Formula (I) by the coupling an amine intermediate with a halide containing intermediate wherein $R_1$ is a protected amide. Again the coupling is in the presence of a base, a palladium catalyst and a ligand in a suitable solvent. By way of example only the palladium catalyst is tris(dibenzylideneacetone)dipalladium(0) ($Pd_2(dba)_3$), the ligand is xantphos, the base is $Cs_2CO_3$ and the solvent is 1,4-dioxane.

Reaction Scheme (IV)

Reaction scheme (V) illustrates the deprotection of a protected amide to yield compounds of Formula (I) wherein $R_1$ is an amide. By way of example only, deprotection occurs in the presence of trifluoracetic acid and dichloromethane.

Reaction Scheme (V)

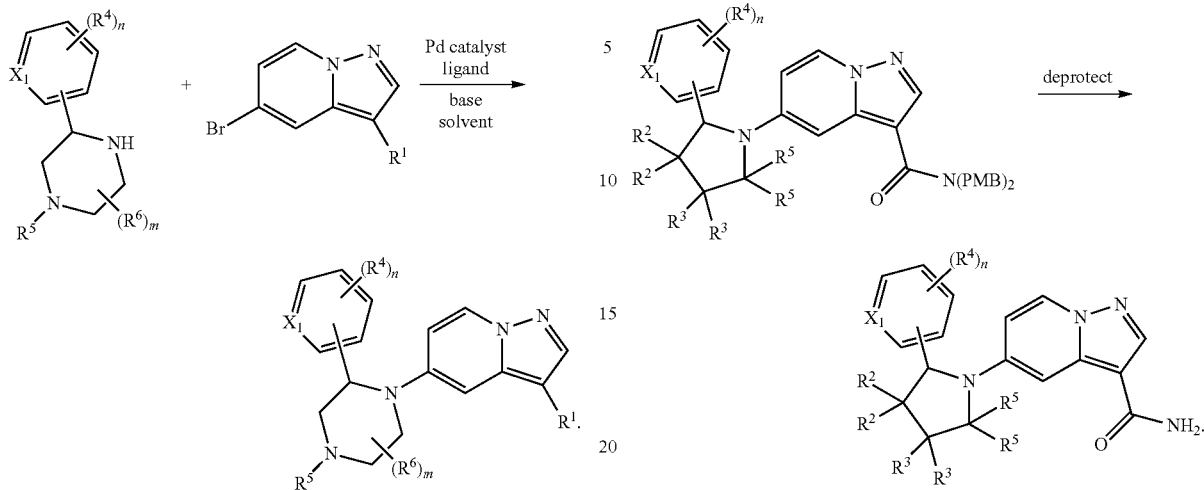

Reaction scheme (VI) illustrates the synthesis of certain compounds of Formula (I) by the interconversion of compounds of Formula (I) wherein $R_1$ is an ester moiety to a carboxylic acid moiety and subsequent conversion of the carboxylic acid to an amide. By way of example only, the carboxylic acid is formed by hydrolysis of the ester in the presence of a base and a sutable solvent. By way of example only thebase is LiOH and the solvent is a mixture of THF, methanol and water. By way of example only, the amide is formed from the carboxylic acid in the presence of ammonium hydroxide, HATU, DIEA and DMF.

Reaction Scheme (VI)

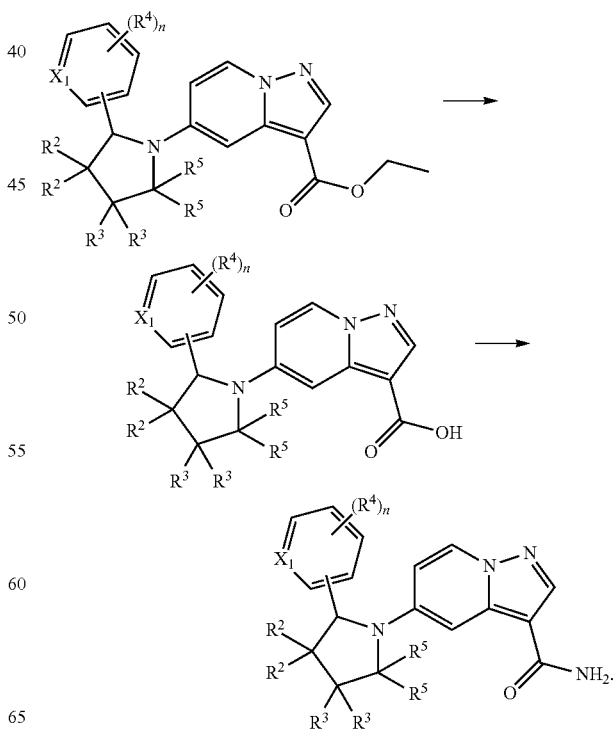

Compounds of the invention and intermediates can also be converted into each other according to methods generally known to those skilled in the art.

Reaction scheme (VII) illustrates the synthesis of certain amine intermediates used to obtain certain compounds of Formula (I) wherein each $R_2$ is H, each $R_5$ is H and each $R_3$ is independently H or F. Non-limiting examples of the reagents used are shown in Reaction scheme (VII).

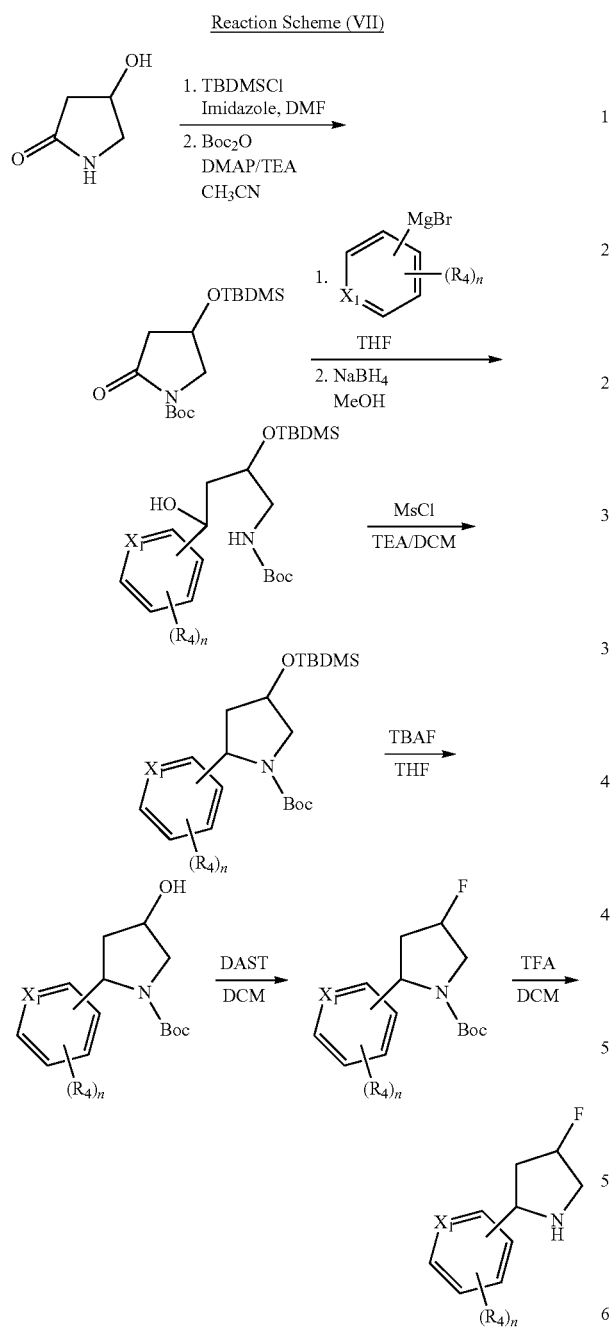

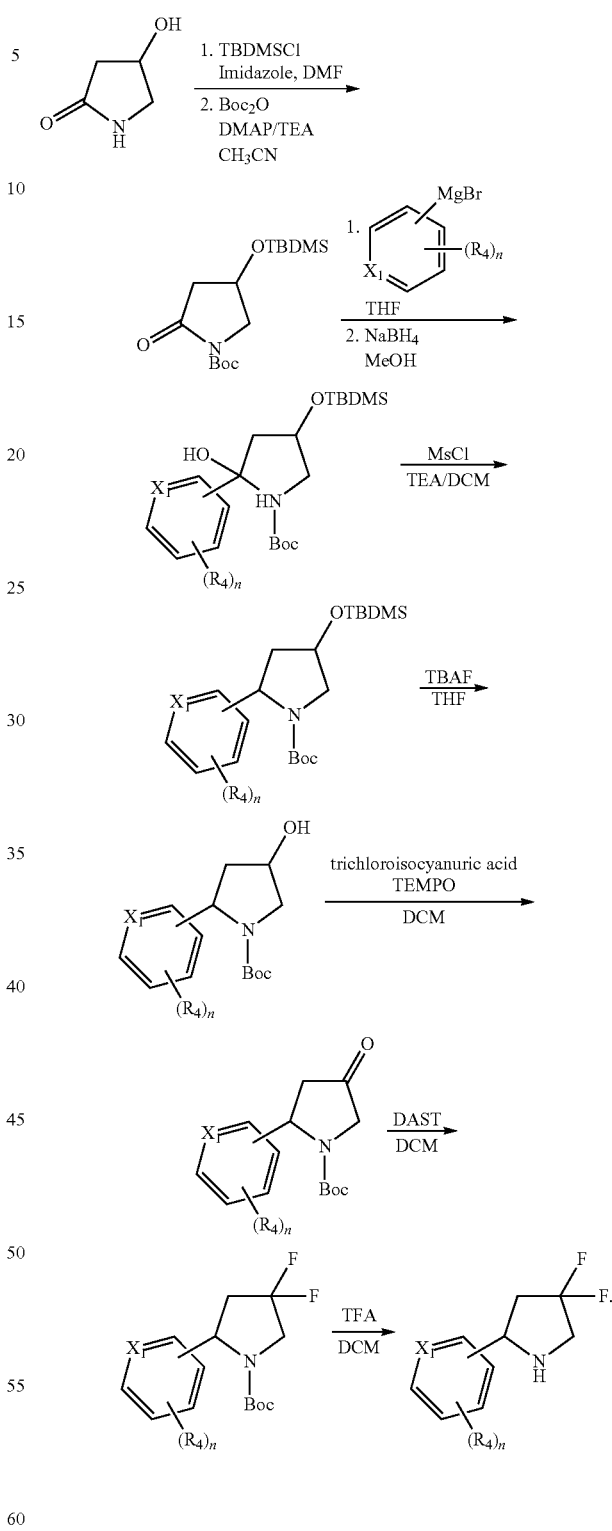

Reaction scheme (VIII) illustrates the synthesis of amine intermediates used to obtain compounds of Formula (I) wherein each $R_2$ is H, each $R_5$ is H and each $R_3$ is F. Non-limiting examples of the reagents used are shown in Reaction scheme (VIII).

Reaction scheme (IX) illustrates the synthesis of amine intermediates used to obtain compounds of Formula (I) wherein each $R_2$ is H, each $R_5$ is H and each $R_3$ is independently H or F. Non-limiting examples of the reagents used are shown in Reaction scheme (IX).

Reaction Scheme (IX)
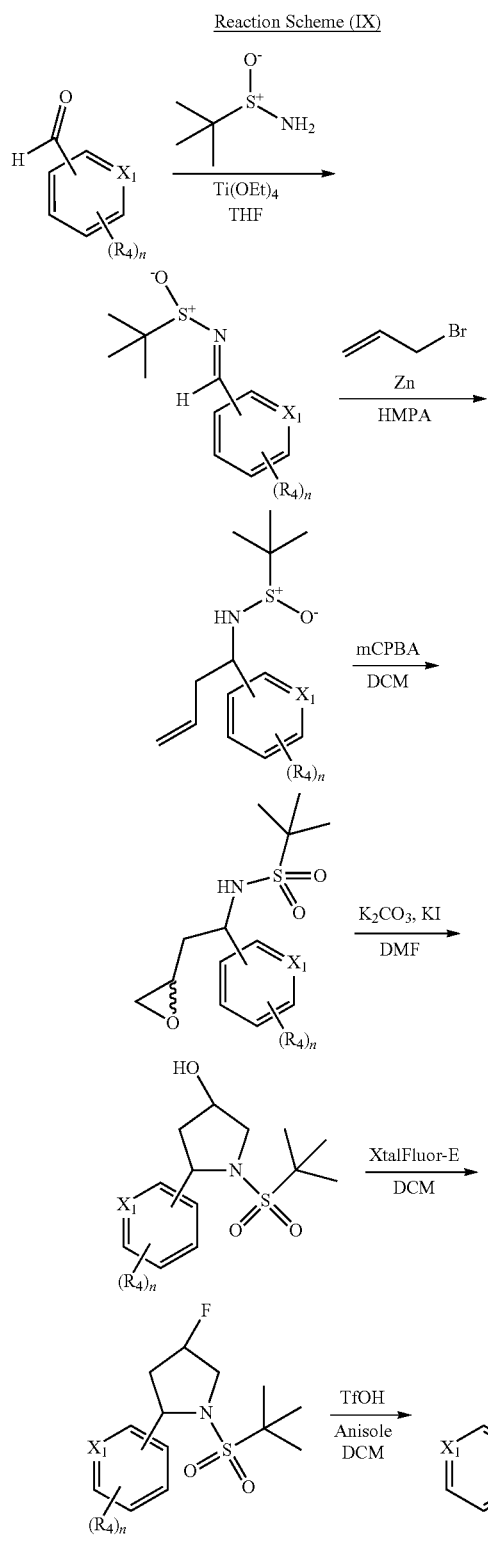
Reaction Scheme (X)
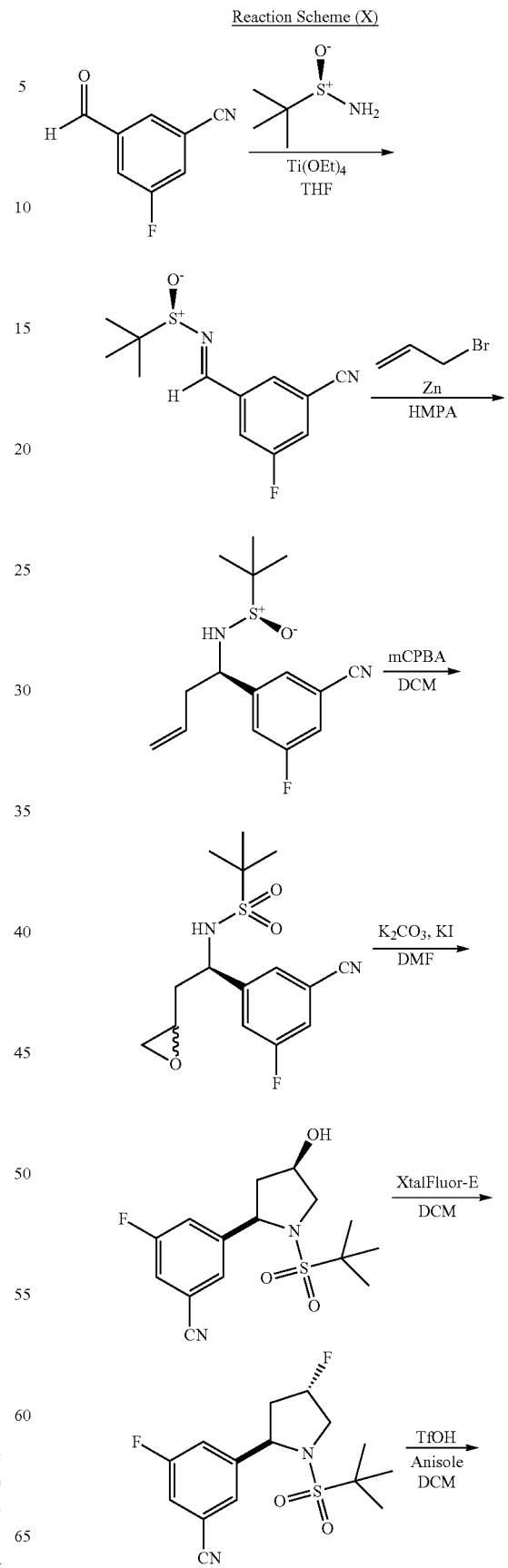
Reaction scheme (X) illustrates the synthesis of a specific amine intermediate used to obtain compounds of Formula (I) wherein each $R_2$ is H, each $R_5$ is H, n is 2 and each $R_4$ is independently CN or F and each $R_3$ is independently H or F. Non-limiting examples of the reagents used are shown in Reaction scheme (X).

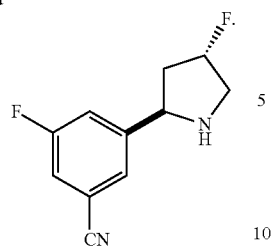
Reaction scheme (XI) illustrates an alternative synthesis of a specific amine intermediate used to obtain compounds of Formula (I) wherein each $R_2$ is H, each $R_5$ is H, n is 2 and each $R_4$ is independently CN or F and each $R_3$ is independently H or F. Non-limiting examples of the reagents used are shown in Reaction scheme (XI).
Reaction Scheme (XI)
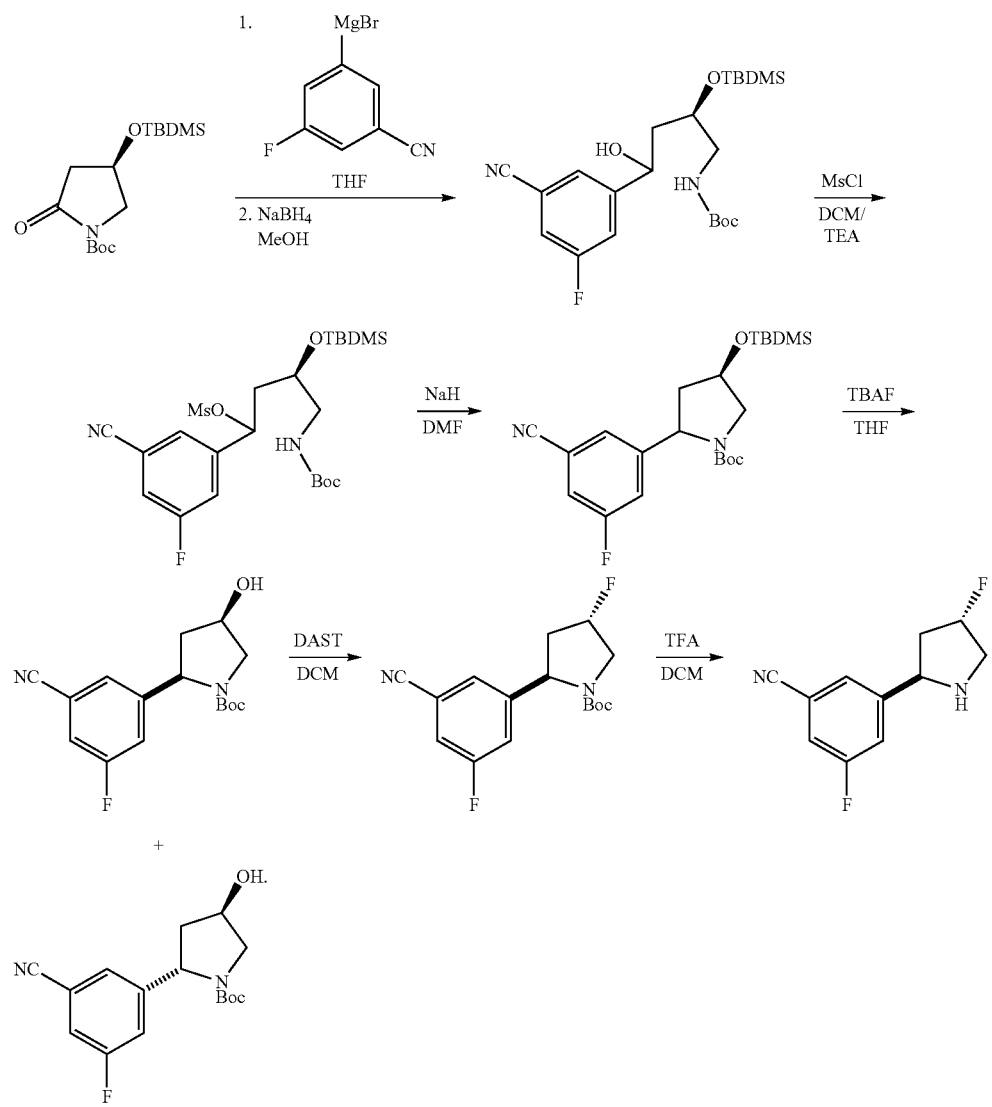

Reaction scheme (XII) illustrates the synthesis of certain amine intermediates used to obtain certain compounds of Formula (I) wherein each $R_2$ is H, each $R_5$ is H and each $R_3$ is independently H or F. Non-limiting examples of the reagents used are shown in Reaction scheme (XII).
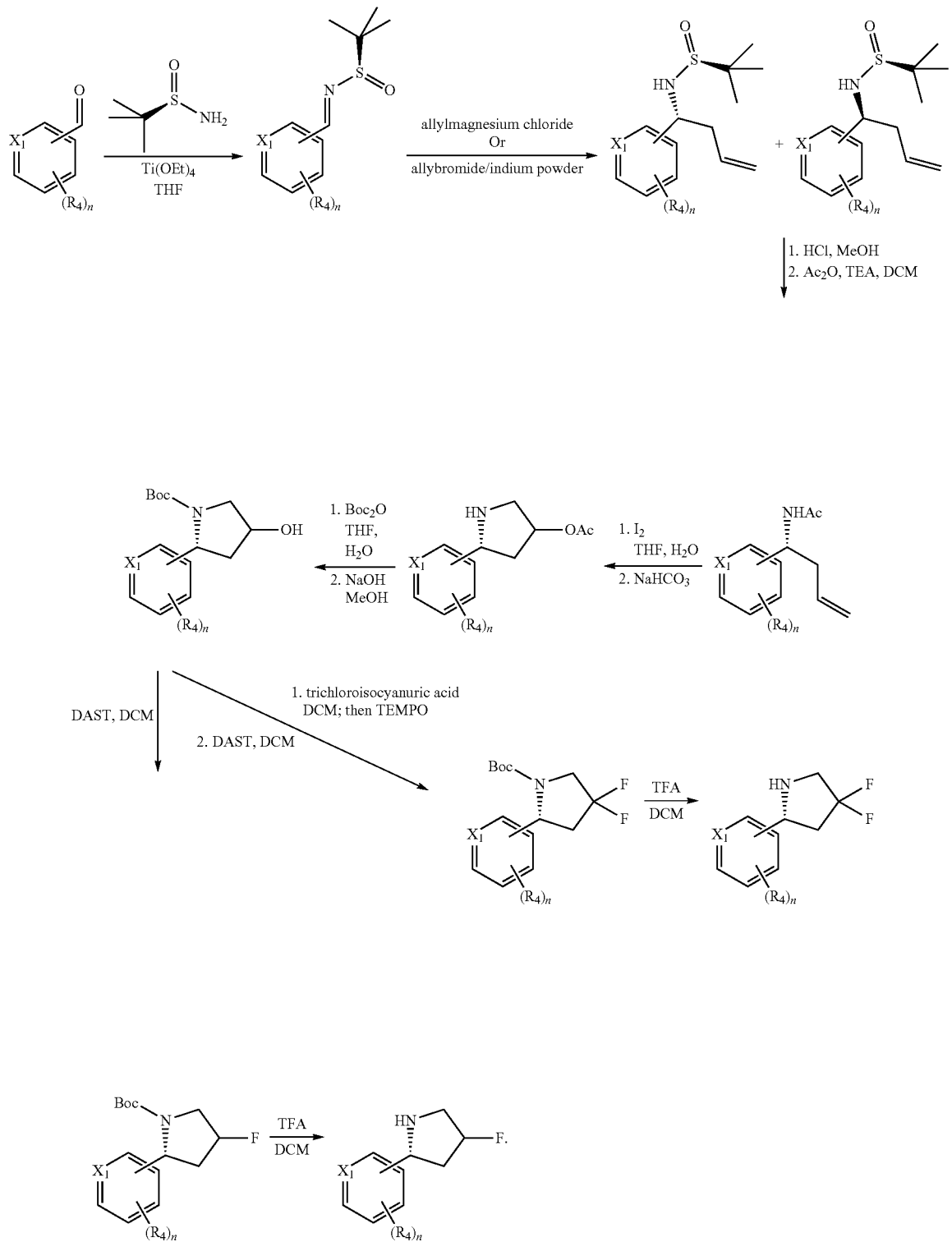
Reaction Scheme (XII)

Reaction scheme (XIII) illustrates the synthesis of halo substituted pyrazolopyridine intermediates used to obtain compounds of Formula (I). Non-limiting examples of the reagents used are shown in Reaction scheme (XIII).

Reaction Scheme (XIII)

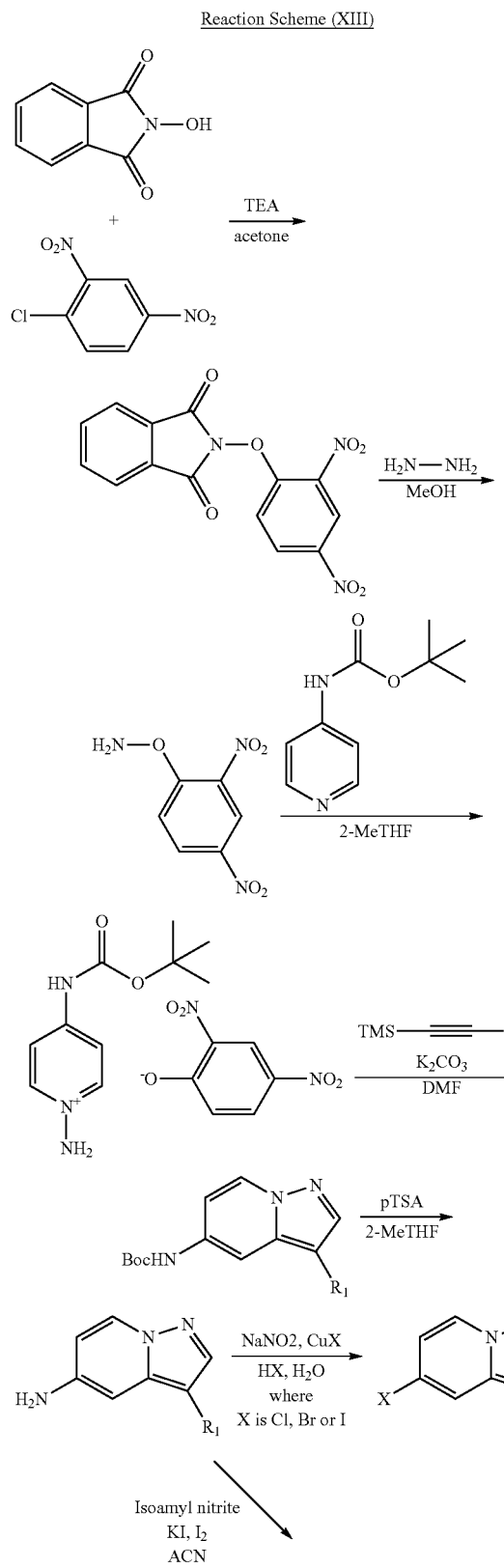

Reaction scheme (XIV) illustrates the synthesis of certain compounds of Formula (I) by the coupling an amine intermediate with a halide containing pyrazolopyridine intermediate in the presence of a base, a palladium catalyst and a ligand in a suitable solvent. By way of example only the palladium catalyst is tris(dibenzylideneacetone)dipalladium(0) ($Pd_2(dba)_3$), the ligand is xantphos, the base is $Cs_2CO_3$ and the solvent is 1,4-dioxane.

Reaction Scheme (XIV)

where X is Cl, Br or I

Reaction scheme (XV) illustrates the synthesis of certain compounds of Formula (I) by the coupling an amine intermediate with a halide containing intermediate in the presence of a base, a palladium catalyst and a ligand in a suitable solvent. By way of example only the palladium catalyst is tris(dibenzylideneacetone)dipalladium(0) ($Pd_2(dba)_3$), the ligand is xantphos, the base is $Cs_2CO_3$ and the solvent is 1,4-dioxane.

Reaction Scheme (XV)

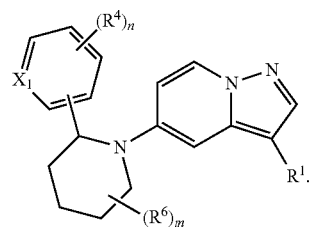

where X is Cl, Br or I

Reaction scheme (XVI) illustrates the synthesis of certain compounds of Formula (I) by the coupling an amine intermediate with a halide containing intermediate wherein $R_1$ is a protected amide. Again the coupling is in the presence of a base, a palladium catalyst and a ligand in a suitable solvent. By way of example only the palladium catalyst is tris(dibenzylideneacetone)dipalladium(0) $(Pd_2(dba)_3)$, the ligand is xantphos, the base is $Cs_2CO_3$ and the solvent is 1,4-dioxane.

Reaction Scheme (XVI)

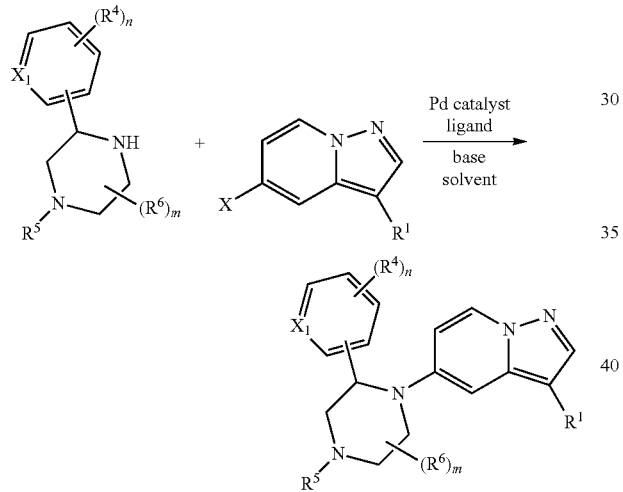

where X is Cl, Br or I

In certain embodiments of compounds of Formula (I) the compounds of Formula (II), or pharmaceutically acceptable salt thereof:

Formula (II)

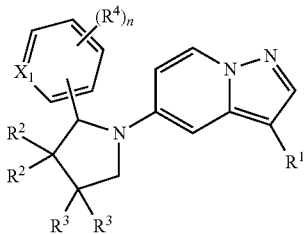

are made or prepared by a process comprising coupling in the presence of a catalyst an amine of Formula A (Formula A)

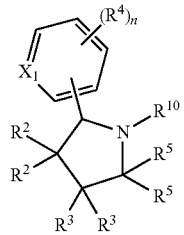

with a compound of Formula C (Formula C)

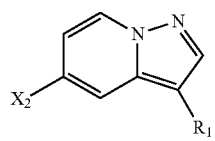

wherein:
$X_1$ is CH or N;
$X_2$ is I, Br or Cl;
$R^1$ is —C(O)NH$_2$, —C(O)N(R$^7$)$_2$, —C(O)N(R$^8$)$_2$, —NR$^7$C(O)R$^8$, —NR$^7$C(O)N(R$^7$)$_2$, —NR$^7$C(O)N(R$^8$)$_2$, —NR$^7$C(O)N(R$^9$)$_2$; —C(O)OR$^7$, —NR$^7$C(O)OR$^7$, —NR$^7$C(O)OR$^8$, —C(O)NR$^7$R$^8$, —C(O)NR$^7$C(O)OR$^7$, —C(O)NR$^7$C(O)NH$_2$, —C(O)NR$^7$C(O)N(R$^7$)$_2$ or H;
each $R^2$ is independently selected from H and $C_1$-$C_6$alkyl;
each $R^3$ is independently selected from H, $C_1$-$C_6$alkyl, —CN, —C(O)N(R$^7$)$_2$, —OR$^7$ and halo, or the two $R^3$ together with the C atom they are attached form a cyclopropyl group spiro attached to the pyrrolidine;
or a $R^2$ and a $R^3$ together with the C atom they are attached form a cyclopropyl ring fused to the pyrrolidine;
each $R^4$ is independently selected from H, halo, —OR$^7$, $C_1$-$C_6$alkyl, $C_1$-$C_6$alkyl substituted with 1-3 halo, $C_1$-$C_6$alkoxy substituted with 1-3 halo, —CN and —C(O)N(R$^7$)$_2$;
each $R^5$ is independently selected from H;
each $R^6$ is independently selected from H, $C_1$-$C_6$alkyl, —CN, —OR$^7$ and halo;
each $R^7$ is independently selected from H, $C_1$-$C_6$alkyl or $C_1$-$C_6$alkyl substituted with 1-3 —OH;
each $R^8$ is independently selected from H, $C_1$-$C_6$alkyl, phenyl, benzyl, phenyl substituted with 1-3 groups independently selected from $R^6$, benzyl substituted with 1-3 groups independently selected from $R^6$, an unsubstituted 5-6 membered heterocycloalkyl having 1 to 2 heteroatoms independently selected from O and N, a 5-6 membered heterocycloalkyl having 1 to 2 heteroatoms independently selected from O and N which is substituted with 1-3 groups independently selected from $R^6$, an unsubstituted $C_3$-$C_6$cycloalkyl, a $C_3$-$C_6$cycloalkyl substituted with 1-3 groups independently selected from $R^6$, an unsubstituted 5-6 membered heteroaryl having 1 to 2 heteroatoms independently selected from O and N, a 5-6 membered heteroaryl having 1 to 2 heteroatoms independently selected from O and N which is substituted with 1-3 groups independently selected from $R^6$;
each $R^9$ is a $C_1$-$C_6$alkyl and together with the N atom they are attached form an unsubstituted 5-6 membered heterocycloalkyl or a 5-6 membered heterocycloalkyl substituted with 1-3 groups independently selected from $R^6$;
$R^{10}$ is H, and
m is 0, 1, 2, 3 or 4, and
n is 0, 1 or 2.

In certain embodiments the amine of Formula (A) used to make or prepare compounds of Formula (II) are compounds of Formula (B),

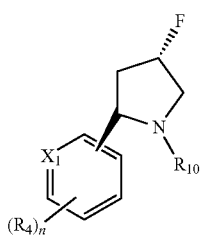

Formula (B)

wherein:
$X_1$ is CH or N;
each $R^4$ is independently selected from H, halo, —$OR^7$, $C_1$-$C_6$alkyl, $C_1$-$C_6$alkyl substituted with 1-3 halo, $C_1$-$C_6$alkoxy substituted with 1-3 halo, —CN and —$C(O)N(R^7)_2$;
$R^{10}$ is H, and
n is 0, 1 or 2.

In a certain embodiments of the compounds of Formula (B) is

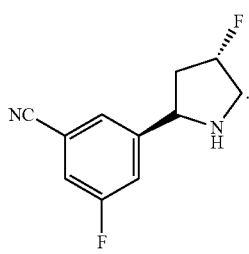

Also provided herein are compounds of Formula (A), or pharmaceutically acceptable salt thereof:

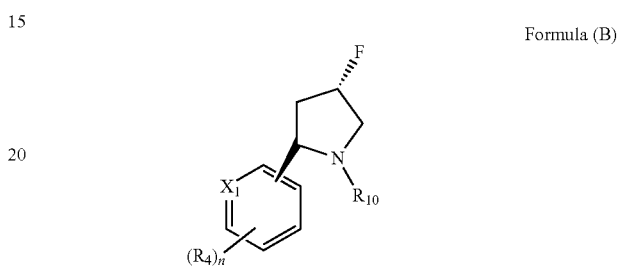

(Formula A)

wherein:
$X_1$ is CH or N;
each $R^2$ is independently selected from H and $C_1$-$C_6$alkyl;
each $R^3$ is independently selected from H, $C_1$-$C_6$alkyl, —CN, —$C(O)N(R^7)_2$, —$OR^7$ and halo, or the two $R^3$ together with the C atom they are attached form a cyclopropyl group spiro attached to the pyrrolidine;
or a $R^2$ and a $R^3$ together with the C atom they are attached form a cyclopropyl ring fused to the pyrrolidine;
each $R^4$ is independently selected from H, halo, —$OR^7$, $C_1$-$C_6$alkyl, $C_1$-$C_6$alkyl substituted with 1-3 halo, $C_1$-$C_6$alkoxy substituted with 1-3 halo, —CN and —$C(O)N(R^7)_2$;
each $R^5$ is independently selected from H;
$R^{10}$ is H or an amine protecting group, and
n is 0, 1 or 2.

In certain embodiments of such compounds of Formula (A), the compound of Formula (A) is a compound of Formula (B),

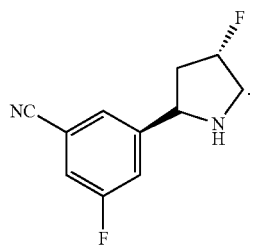

Formula (B)

wherein:
$X_1$ is CH or N;
each $R^4$ is independently selected from H, halo, —$OR^7$, $C_1$-$C_6$alkyl, $C_1$-$C_6$alkyl substituted with 1-3 halo, $C_1$-$C_6$alkoxy substituted with 1-3 halo, —CN and —$C(O)N(R^7)_2$;
$R^{10}$ is H or an amine protecting group, and
n is 0, 1 or 2.

In a certain embodiment of such compounds of Formula (B), the compound of Formula (B) is

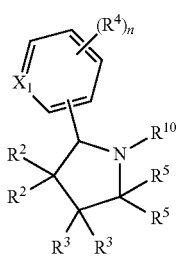

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Pharmacology and Utility

Protein kinases (PTK) play a central role in the regulation of a wide variety of cellular processes and maintaining control over cellular function. Protein kinases catalyze and regulate the process of phosphorylation, whereby the kinases covalently attach phosphate groups to proteins or lipid targets in response to a variety of extracellular signals. Examples of such stimuli include hormones, neurotransmitters, growth and differentiation factors, cell cycle events, environmental stresses and nutritional stresses. An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include, but are not limited to, autoimmune diseases, inflammatory diseases, bone diseases, metabolic diseases, neurological and neurodegenerative diseases, cancer, cardiovascular diseases, respiratory diseases, allergies and asthma, Alzheimer's disease, and hormone-related diseases.

Examples of protein-tyrosine kinases include, but are not limited to,
- (a) tyrosine kinases such as Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-I or c-MET), PDGFR (α and β), Tie-1, Tie-2 (also Tek-1 or Tek), VEGFR1 (also FLT-1), c-FMS, VEGFR2 (also KDR), FLT-3, FLT-4, c-KIT, JAK1, JAK2, JAK3, TYK2, LOK, RET, Ros, TRKA, TRKB, TRKC, PYK2, ALK (Anaplastic Lymphoma Kinase), EPHA (1-8), EPHB (1-6), RON, Fes, Fer or EPHB4 (also EPHB4-1), and
- (b) and serine/threonine kinases such as Aurora, c-RAF, SGK, MAP kinases (e.g., MKK4, MKK6, etc.), SAPK2α, SAPK2β, Ark, ATM (1-3), CamK (1-IV), CamKK, Chk1 and 2 (Checkpoint kinases), CK1, CK2, Erk, IKK-I (also IKK-α or CHUK), IKK-2 (also IKK-β), Ilk, Jnk (1-3), LimK (1 and 2), MLK3Raf (A, B and C), CDK (1-10), PKC (including all PKC subtypes), PIk (1-3), NIK, Pak (1-3), PDK1, PKR, RhoK, RIP, RIP-2, GSK3 (α and β), PKA, P38, Erk (1-3), PKB (including all PKB subtypes) (also AKT-1, AKT-2, AKT-3 or AKT3-1), IRAK1, FRK, SGK, TAK1 and Tp1-2 (also COT).

Phosphorylation modulates or regulates a variety of cellular processes such as proliferation, growth, differentiation, metabolism, apoptosis, motility, transcription, translation and other signaling processes. Aberrant or excessive PTK activity has been observed in many disease states including, but not limited to, benign and malignant proliferative disorders, diseases resulting from inappropriate activation of the immune system and diseases resulting from inappropriate activation of the nervous systems. Specific diseases and disease conditions include, but are not limited to, autoimmune disorders, allograft rejection, graft vs. host disease, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, obesity, diabetes mellitus, diabetic angiopathy, retinopathy of prematurity, infantile hemangiomas, non-small cell lung, bladder and head and neck cancers, prostate cancer, breast cancer, ovarian cancer, gastric and pancreatic cancer, psoriasis, fibrosis, rheumatoid arthritis, atherosclerosis, restenosis, auto-immune disease, allergy, respiratory diseases, asthma, transplantation rejection, inflammation, thrombosis, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases and bronchitis.

Tyrosine kinases can be broadly classified as receptor-type (having extracellular, transmembrane and intracellular domains) or the non-receptor type (being wholly intracellular) protein tyrosine kinases. Inappropriate or uncontrolled activation of many of these kinase (aberrant protein tyrosine kinase activity), for example by over-expression or mutation, results in uncontrolled cell growth. Many of the protein tyrosine kinases, whether a receptor or non-receptor tyrosine kinase have been found to be involved in cellular signaling pathways involved in numerous pathogenic conditions, including, but not limited to, immunomodulation, inflammation, or proliferative disorders such as cancer.

Compounds of the invention are inhibitors TrkA, TrkB and/or TrkC, and as such the compounds and pharmaceutical compositions provided herein are useful for treating diseases or disorders in which such kinases contribute to the pathology and/or symptomology of a disease or disorder associated with such kinases. Such diseases or disorders include, but are not limited to, cancer, pain, cachexia, a proliferative diseases, a pain disorder, a dermatological disease, a metabolic disease, a muscle disease, neurodegenerative diseases and/or disorders, neurological diseases and/or disorders, an inflammatory disease, fibrosis, an infectious disease, a respiratory disease, a pulmonary disease and hyperplasiaan inflammatory disease and wherein the compound is a compound of Formula (I). In certain embodiments the disease is asthma, chronic obstructive pulmonary disease (COPD), adult respiratory distress syndrome (ARDS), bronchitis, dermatitis, allergic rhinitis, psoriasis, scleroderma, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, colon cancer or papillary thyroid carcinoma.

Receptor Tyrosine Kinases (RTKs).

The Receptor Tyrosine Kinases (RTKs) comprise a large family of transmembrane receptors with diverse biological activities. A number of distinct RTK subfamilies have been identified including, but not limited to, ALK receptor family, EGF receptor family, the Insulin receptor family, the PDGF receptor family, the FGF receptor family, the VEGF receptor family, the HGF receptor family, the Trk receptor family, the EPH receptor family, the AXL receptor family, the LTK receptor family, the TIE receptor family, the ROR receptor family, the DDR receptor family, the RET receptor family, the KLG receptor family, the RYK receptor family and the MuSK receptor family.

Receptor tyrosine kinases have been shown to be not only key regulators of normal cellular processes but also to have a critical role in the development and progression of many types of cancer. The receptor tyrosine kinase (RTK) family includes receptors that are crucial for the growth and differentiation of a variety of cell types. The intrinsic function of RTK mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response such as, by way of example only, cell division, differentiation, metabolic effects, and changes in the extracellular microenvironment.

Tropomyosin-Receptor-Kinase (Trk) Family

The Trk family receptor tyrosine kinases (NTRK genes), TrkA (NTRK1), TrkB (NTRK2), and TrkC(NTRK3), are the signaling receptors that mediate the biological actions of the peptide hormones of the neurotrophin family. Trk receptors are membrane-bound receptors that, through several signal cascades, control neuronal growth and survival, and differentiation, migration and metastasis of tumor cells. The neurotrophin family of growth factors includes nerve growth factor (NGF), brain-derived neurotrophic factor (BDNF), and two neurotrophins (NT), NT-3, and NT-4. Neurotrophins are critical to the functioning of the nervous system, and the activation of Trk receptors by neurotrophin binding leads to activation of signal cascades resulting in promoting survival and other functional regulation of cells. Each type of neurotrophin has a different binding affinity toward its corresponding Trk receptor, and upon neurotrophin binding, the Trk receptors phosphorylates themselves and members of the MAPK pathway. The differences in the signaling initiated by these distinct types of receptors are important for generating diverse biological responses.

The Trk family kinase receptors promote tumorigenesis and are able to control tumor cell growth and survival as well as differentiation, migration and metastasis. The Trk receptors are implicated in the development and progression of cancer, through upregulation of either, the receptor, their ligand (NGF, BDNF, NT-3, and NT-4), or both. In many cases high Trk expression is associated with aggressive tumor behavior, poor prognosis and metastasis. Thus, diseases and disorders related to Trk receptors result from 1) expression of a Trk receptor(s) in cells which normally do not express such a receptor(s); 2) expression of a Trk receptor(s) by cells which normally do not express such a receptor(s); 3) increased expression of Trk receptor(s) leading to unwanted cell proliferation; 4) increased expression of Trk receptor(s) leading to adhesion independent cell survival; 5) mutations leading to constitutive activation of Trk receptor(s); 6) over stimulation of Trk receptor(s) due to abnormally high amount of, or mutations in, Trk receptor(s), and/or 7) abnormally high amount of Trk receptor(s) activity due to abnormally high amount of, or mutations in, Trk receptor(s).

Genetic abnormalities, i.e. point mutations and chromosomal rearrangements involving both the genes expressing TrkB and TrkC have been found in a variety of cancer types. In a kinome-wide approach to identify point mutants in tyrosine kinases, mutations in the genes expressing TrkB and TrkC were found in cell lines and primary samples from patients with colorectal cancer. In addition, chromosomal translocations involving the genes expressing TrkA and TrkB have been found in several different types of tumors. Gene rearrangements involving the genes expressing TrkA and a set of different fusion partners (TPM3, TPR, TFG) are a hallmark of a subset of papillary thyroid cancers. Moreover, secretary breast cancer, infant fibrosarcoma and congenital mesoblastic nephroma have been shown to be associated with a chromosomal rearrangement t(12;15) generating a ETV6-NTRK3 fusion gene that was shown to have constitutive kinase activity and transforming potential in several different cell lines including fibroblasts, hematopoietic cells and breast epithelial cells.

TrkA has the highest affinity to the binding nerve growth factor (NGF). NGF is important in both local and nuclear actions, regulating growth cones, motility, and expression of genes encoding the biosynthesis enzymes for neurotransmitters. Nocireceptive sensory neurons express mostly TrkA and not TrkB or TrkC.

TrkB serves as a receptor for both BDNF and NT-4, and is expressed in neuroendocrine-type cells in the small intestine and the colon, in the alpha cells of the pancreas, in the monocytes and macrophages of the lymph nodes and of the spleen, and in the granular layers of the epidermis. TrkB is also expressed in cancerous prostate cells but not in normal cells. The binding of BDNF to TrkB receptor causes activation of intercellular cascades which regulate neuronal development and plasticity, long-term potentiation, and apoptosis. BDNF promotes the proliferation, differentiation and growth and survival of normal neural components such as retinal cells and glial cells. In addition, TrkB activation is a potent and specific suppressor of anchorage independent cell death (anoikis), which is apoptosis induced by loss of attachment of a cell to its matrix. By way of example, activation of the Phosphatidylinositol-3-kinase/Protein Kinase B signaling axis by TrkB promotes the survival of non-transformed epithelial cells in 3-dimensional cultures and induces tumor formation and metastasis of those cells in immunocompromised mice. Anchorage independent cell survival is a metastatic process allowing tumor cells to migrate through the systemic circulation and grow at distant organs. Agonism of TrkB results in the failure of induced cell death by cancer treatments. Thus, TrkB modulation is a target for treatment of benign and malignant proliferative diseases, especially tumor diseases.

Diseases and disorders related to the TrkB receptor include, but are not limited to, cancers, such as, by way of example only, neuroblastoma progression, Wilm's tumor progression, breast cancer, pancreatic cancer, colon cancer, prostate cancer, and lung cancer. The TrkB receptor has been shown to be associated with Alzheimer's disease.

Additional research has discovered mutations in TrkB in humans that result in a partial loss of enzymatic activity of the receptor. This genetic legion results in an increase in apetite and obesity (hyperphagic obesity). Similar results have been obtained in mouse models, thus strengthening the hypothesis that lowering TrkB activity could serve to modulate feeding behavior, and would be useful in the treatment of disorders such as anorexia.

Other non-oncology indications for a Trk inhibitor include atopic dermatitis and psoriasis.

TrkC is activated by binding with NT-3 and is expressed by proprioceptive sensory neurons. The axons of these proprioceptive sensory neurons are much thicker than those of nocireceptive sensory neurons, which express TrkA. Signalling through TrkC leads to cell differentiation and development of proprioceptive neurons that sense body position. Mutations in this gene expressing TrkC is associated with medulloblastomas, secretory breast carcinomas and other cancers. In addition, high expression of TrkC is a hallmark of melanoma, especially in cases with brain metastasis.

Trk family members, especially NTRK1 and NTRK2, play a role in pancreatic cancer wherein: i) high expression of various members of the Trk family and their cognate ligands have been shown in tissue samples from patients with pancreatic cancer; ii) NTRK2 overexpression has been linked to a malignant, highly metastatic phenotype of pancreatic cancer; iii) high expression of NTRK1/NGF, has been correlated with enhanced proliferation, invasive behavior and pain in PC patients; and iv) nerve growth factor has been shown to increase the invasive potential of pancreatic cancer cell lines.

Overexpression of TrkA in pancreatic cancer might be caused by methylation of negative regulatory AP-1 sites in the promoter region of TrkA.

Gene rearrangements involving NTRK1 are a hallmark of a subset of papillary thyroid cancers. Thyroid-specific TRKoncogenes are generated by rearrangements of the NTRK1 gene with three different activating genes, namely TPR, TPM3, and TFG.

Several loss of function mutations in thr TrkA are responsible for congenital insensitivity to pain with anhidrosis (CIPA), a disorder characterized by a lack of pain sensation and anhidrosis. More recently, an antagonistic TrkA antibody has been shown to be efficacious in inflammatory and neupathic pain animal models. In addition, TrkA and NGF have been implicated in eliciting cancer related pain. It was shown that NGF secreted by tumor cell and tumor invading macrophages secret NGF which directly stimulates TrkA located on peripheral pain fibers. Using various tumor models in both mouse and rats it was demonstrated that neutralizing NGF with a monoclonal antibody inhibits cancer related pain to a degree similar or superior to the highest tolerated dose of morphine. Therefore, a selective inhibitor of TrkA can be used in the treatment of pain associated with cancer.

High expression of Trk's are found in Wilm's tumor, prostate carcinoma and pancreatic cancers. High expression of TrkC is a hallmark of carcinoma. In neuroblastoma, high TRKB expression is correlated with an aggressive untreatable tumors and resistance to standard cytotoxic therapies. In mouse models of cancer metastasis, the NTRK2 gene (TrkB protein) can induce metastasis and removal of the gene reverses this metastatic potential. The bulk of evidence suggests that inhibition of Trk enzymes would block the growth and spread of various cancers where Trk is involved. Furthermore, activating mutations in Trk's are present in 7% of cancers.

Certain compounds, pharmaceutical compositions and pharmaceutical combination provided herein are inhibitors of Trk receptor tyrosine kinases (TrkA, TrkB, and TrkC), thus such compounds, pharmaceutical compositions and pharmaceutical combination are useful for the treatment of diseases and/or disorders that respond to inhibition of Trk receptor tyrosine kinases (TrkA, TrkB, and TrkC). In certain embodiments, such compounds, pharmaceutical compositions and pharmaceutical combination are useful in the treatment of cancer by inhibiting the development and/or progression of the cancer. In certain embodiments, such compounds, pharmaceutical compositions and pharmaceutical combination are useful in the treatment of diseases and/or disorders including, but are not limited to, neuroblastoma, Wilm's tumor, breast cancer, pancreatic cancer, colon cancer, prostate cancer, lung cancer, melanoma, atopic dermatitis, psoriasis and Alzheimer's disease.

In accordance with the foregoing, the present invention further provides a method for preventing or treating any of the diseases or disorders described above in a subject in need of such treatment, which method comprises administering to said subject a therapeutically effective amount (See, "Routes of Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Routes of Administration and Pharmaceutical Compositions

For the therapeutic uses of compounds of Formula (I), or pharmaceutically acceptable salts, solvates, N-oxides and isomers thereof, described herein, such compounds are administered in therapeutically effective amounts either alone or as part of a pharmaceutical composition. Accordingly, provided herein are pharmaceutical compositions, which comprise at least one compound of Formulas (I) described herein, pharmaceutically acceptable salts and/or solvates thereof, and one or more pharmaceutically acceptable carriers, diluents, or excipients. In addition, such compounds and compositions are administered singly or in combination with one or more additional therapeutic agents. The routes of administration of compounds of Formula (I) and pharmaceutical compositions include, but are not limited to, oral administration, intravitreal administration, rectal administration, parenteral, intravenous administration, intraperitoneal administration, intramuscular administration, inhalation, transmucosal administration, pulmonary administration, intestinal administration, subcutaneous administration, intramedullary administration, intrathecal administration, direct intraventricular, intranasal administration, topical administration, ophthalmic administration or otic administration.

In certain embodiments, compounds of Formula (I) or pharmaceutical compositions described herein are administered locally, while in other embodiments compounds of Formula (I) or pharmaceutical composite described herein are administered systemically. Local administration includes, but is not limited to, injection into an organ, optionally in a depot or sustained release formulation. Systemic administration includes, but is not limited to, oral administration or intravenous administration. In other embodiments, compounds of Formula (I) or pharmaceutical compositions described herein are administered in a targeted drug delivery system, such as, by way of example only, in a liposome coated with organ-specific antibody. The liposome is targeted to and taken up selectively by the organ. In other embodiments, compounds of Formula (I) or pharmaceutical compositions described herein are administered in the form of a rapid release formulation, while in other embodiments, compounds of Formula (I) or pharmaceutical compositions described herein are administered in the form of an extended release formulation. In other embodiments, compounds of Formula (I) or pharmaceutical compositions described herein are administered in the form of an intermediate release formulation.

The therapeutically effective amount will vary depending on, among others, the disease indicated, the severity of the disease, the age and relative health of the subject, the potency of the compound administered, the route of administration and the treatment desired.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

Other aspects provided herein are processes for the preparation of pharmaceutical composition which comprise at least one compound of Formula (I) described herein. In certain embodiments, such processes include admixing a compound of Formula (I) described herein with one or more pharmaceutically acceptable carriers, diluents or excipients. In certain embodiments, the pharmaceutical compositions comprise a compound of Formula (I) in free form or in a pharmaceutically acceptable salt or solvate form. In certain embodiments, the pharmaceutical compositions comprising a compound of Formula (I) in free form or in a pharmaceutically acceptable salt or solvate form, in association with at least one pharmaceutically acceptable carrier, diluent or excipient are manufactured by mixing, dissolving, granulating dragee-making, levigating, emulsifying, encapsulating, entrapping or compression processes and/or coating methods. In other embodiments, such compositions are optionally contain excipients, such as preserving, stabilizing, wetting or emulsifying agents, solution promoters, salts for regulating the osmotic pressure and/or buffers. In other embodiments, pharmaceutical compositions comprising a compound of Formula (I) are sterilized.

Oral Dosage Forms

In certain embodiments, the pharmaceutical compositions containing at least one compound of Formula (I) are administered orally as discrete dosage forms, wherein such dosage forms include, but are not limited to, capsules, gelatin capsules, caplets, tablets, chewable tablets, powders, pills, dragees, granules, liquids, gels, syrups, flavored syrups, elixirs, slurries, solutions or suspensions in aqueous or non-aqueous liquids, edible foams or whips, and oil-in-water liquid emulsions or water-in-oil liquid emulsions. The capsules, gelatin capsules, caplets, tablets, lozenges, chewable tablets, powders or granules, used for the oral administration of at least one compound of Formula (I) are prepared by admixing at least one compound of Formula (I) (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing at least one compound of Formula (I) (active ingredients) with liquid carriers, finely divided solid carriers, or both, and then shaping the product into the desired presentation if necessary. In certain embodiments, tablets are prepared by compression. In other embodiments, tablets are prepared by molding.

In certain embodiments, at least one compound of Formula (I) is orally administered as a controlled release dosage form. Such oral dosage forms may be either film coated or enteric coated according to methods known in the art. Such dosage forms are used to provide slow or controlled-release of one or more compounds of Formula (I). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I), reduce dosage frequency, and increase patient compliance.

Administration of compound of Formula (I) as oral fluids such as solution, syrups and elixirs are prepared in unit dosage forms such that a given quantity of solution, syrups or elixirs contains a predetermined amount of a compound of Formula (I). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing at least one compound of Formula (I) are administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, physiological saline buffer, Ringers Injection solution, Dextrose Injection, Dextrose and Sodium Chloride Injection, and Lactated Ringer's Injection solution; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In certain embodiments, a compound of Formula (I) or composition containing one or more compounds of Formula (I) is parenteral administration by bolus injection. In other embodiments, a compound of Formula (I) or composition containing one or more compounds of Formula (I) is parenteral administration by continuous infusion. Formulations for injection are presented in unit dosage form, by way of example only, in ampoules or formulations for injection are presented in multi-dose containers, with an added preservative. The compositions may take such forms as suspensions, solutions or emulsions in oily or aqueous vehicles, and may contain formulatory agents such as suspending, stabilizing and/or dispersing agents.

Transdermal Administration

In certain embodiments pharmaceutical compositions containing at least one compound of Formula (I) are administered transdermally. Such transdermal dosage forms include "reservoir type" or "matrix type" patches, which are applied to the skin and worn for a specific period of time to permit the penetration of a desired amount of a compound of Formula (I). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used. In certain embodiments transdermal administration is used to provide continuous, while in other embodiments transdermal administration is used to provide discontinuous infusion of a compound of Formula (I) in controlled amounts.

In certain embodiments, the rate of absorption is slowed by using rate-controlling membranes or by trapping the compound within a polymer matrix or gel. In certain embodiments, transdermal delivery is via a transdermal patch.

Formulations for transdermal delivery of a compound of Formula (I) include an effective amount of a compound of Formula (I), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compound of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I). In other embodiments, the polarity of a solvent carrier, the ionic strength, or tonicity are adjusted to improve delivery. In other embodiments, compounds such as stearates are added to advantageously alter the hydrophilicity or lipophilicity of one or more compound of Formula (I) so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of the compound of Formula (I) are used to further adjust the properties of the resulting composition.

In other embodiments, transdermal delivery of the compound of Formula (I) is accomplished by means of iontophoretic patches and the like Topical Dosage Forms In certain embodiments at least one compound of Formula (I) is administered by topical application of pharmaceutical composition containing at least one compound of Formula (I) in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compound of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Pulmonary Administration

In certain embodiments pharmaceutical compositions containing at least one compound of Formula (I) are administered by inhalation. Dosage forms for inhaled administration are formulated as aerosols or dry powders. Aerosol formulations for inhalation administration comprise a solution or fine suspension of at least one compound of Formula (I) in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain embodiments, compound of Formula (I) are be administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I) and a powder base such as lactose or starch. In certain embodiments, compound of Formula (I) are delivered to the lung using a liquid spray device, wherein such devices use extremely small nozzle holes to aerosolize liquid drug formulations that can then be directly inhaled into the lung. In other embodiments, compound of Formula (I) are delivered to the lung using a nebulizer device, wherein a nebulizers creates an aerosols of liquid drug formulations by using ultrasonic energy to form fine particles that can be readily inhaled. In other embodiments, compound of Formula (I) are delivered to the lung using an electrohydrodynamic ("EHD") aerosol device wherein such EHD aerosol devices use electrical energy to aerosolize liquid drug solutions or suspensions.

In certain embodiments, the pharmaceutical composition containing at least one compound of Formula (I), or pharmaceutically acceptable salts and solvates thereof, described herein, also contain one or more absorption enhancers. In certain embodiments, such absorption enhancers include, but are not limited to, sodium glycocholate, sodium caprate, N-lauryl-β-D-maltopyranoside, EDTA, and mixed micelles.

In certain embodiments pharmaceutical compositions containing at least one compound of Formula (I) are administered nasally. The dosage forms for nasal administration are formulated as aerosols, solutions, drops, gels or dry powders.

Rectal Administration

In certain embodiments pharmaceutical compositions containing at least one compound of Formula (I) are administered rectally in the form of suppositories, enemas, retention enemas ointment, creams rectal foams or rectal gels. In certain embodiments such suppositories are prepared from fatty emulsions or suspensions, cocoa butter or other glycerides.

Depot Administration

In certain embodiments pharmaceutical compositions containing at least one compound of Formula (I) are formulated as a depot preparation. Such long acting formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

In certain embodiments injectable depot forms are made by forming microencapsulated matrices of the compound of Formula (I) in biodegradable polymers. The rate of compound of Formula (I) release is controlled by varying the ratio of compound of Formula (I) to polymer and the nature of the particular polymer employed. In other embodiments, depot injectable formulations are prepared by entrapping the compound of Formula (I) in liposomes or microemulsions.

Ophthalmic Administration

In certain embodiments, a compound of Formula (I) or pharmaceutical composition described herein are ophthalmically administered to the eye. Administration to the eye generally results in direct contact of the agents with the cornea, through which at least a portion of the administered agents pass. In certain embodiments, such compounds of Formula (I) or pharmaceutical compositions have an effective residence time in the eye of about 2 to about 24 hours. In certain embodiments, such compounds of Formula (I) or pharmaceutical compositions have an effective residence time in the eye of about 4 to about 24 hours. In certain embodiments, such compounds of Formula (I) or pharmaceutical compositions have an effective residence time in the eye of about 6 to about 24 hours.

Ophthalmic administration, as used herein, includes, but is not limited to, topical administration, intraocular injection, subretinal injection, intravitreal injection, periocular administration, subconjuctival injections, retrobulbar injections, intracameral injections (including into the anterior or vitreous chamber), sub-Tenon's injections or implants, ophthalmic solutions, ophthalmic suspensions, ophthalmic ointments, ocular implants and ocular inserts, intraocular solutions, use of iontophoresis, incorporation in surgical irrigating solutions, and packs (by way of example only, a saturated cotton pledget inserted in the formix). In certain embodiments, the compounds of Formula (I) or pharmaceutical composition described herein are formulated as an ophthalmic composition and are administered topically to the eye. Such topically administered ophthalmic compositions include, but are not limited to, solutions, suspensions, gels or ointments.

In certain embodiments the pharmaceutical compositions, comprising at least one compound of Formula (I) described herein, used for ophthalmic administration take the form of a liquid where the compositions are present in solution, in suspension or both. In some embodiments, a liquid composition includes a gel formulation. In other embodiments, the liquid composition is aqueous. In other embodiments, such liquid compositions take the form of an ointment. In certain embodiments pharmaceutical compositions containing at least one compound of Formula (I) are administered ophthamically as eye drops formulated as aqueous solutions that optionally contain solubilizers, stabilizers, tonicity enhancing agents, buffers and preservatives. A desired dosage is administered via a known number of drops into the eye. By way of example only, for a drop volume of 25 I, administration of 1-6 drops delivers 25-150 l of the composition. In certain embodiments, the aqueous compositions contain from about 0.01% to about 50% weight/volume of a compound of Formula (I). In other embodiments, the aqueous compositions contain from about 0.1% to about 20% weight/volume of a compound of Formula (I). In still other embodiments, the aqueous compositions contain from about 0.2% to about 10% weight/volume of a compound of Formula (I). In certain embodiments, the aqueous compositions contain from about 0.5% to about 5%, weight/volume of a compound of Formula (I).

In certain embodiments the aqueous compositions have an ophthalmically acceptable pH and osmolality. In certain embodiments the aqueous compositions include one or more ophthalmically acceptable pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

In certain embodiments the compositions also include also include one or more ophthalmically acceptable salts in an amount required to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In certain embodiments the aqueous compositions also contain one or more polymers as suspending agents. Such polymers include, but are not limited to, water-soluble polymers such as cellulosic polymers described herein, (for example only, hydroxypropyl methylcellulose), and water-insoluble polymers described herein (for example only, cross-linked carboxyl-containing polymers). In certain embodiments, the aqueous compositions also include an ophthalmically acceptable mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

In certain embodiments the compositions also include ophthalmically acceptable solubilizing agents to aid in the solubility of a compound of Formula (I). The term "solubilizing agent" generally includes agents that result in formation of a micellar solution or a true solution of the agent. In certain embodiments, ophthalmically acceptable nonionic surfactants including, but not limited to, polysorbate 80 are used as solubilizing agents. In other embodiments, ophthalmically acceptable glycols including, but not limited to, polyglycols, polyethylene glycol 400, and glycol ethers are used as solubilizing agents.

In certain embodiments the compositions also include one or more ophthalmically acceptable surfactants to enhance physical stability or for other purposes. Such nonionic surfactants include, but are not limited to, polyoxyethylene fatty acid glycerides and vegetable oils (by way of example only, polyoxyethylene (60) hydrogenated castor oil) and polyoxyethylene alkylethers and alkylphenyl ethers (by way of example only, octoxynol 10 and octoxynol 40).

In certain embodiments the compositions also include one or more ophthalmically acceptable preservatives to inhibit microbial activity. Such preservatives include, but are not limited to mercury-containing substances such as merfen and thiomersal; stabilized chlorine dioxide; and quaternary ammonium compounds such as benzalkonium chloride, cetyltrimethylammonium bromide and cetylpyridinium chloride.

In certain embodiments the compositions also include one or more antioxidants to enhance chemical stability where required. Such antioxidants include, but are not limited to, ascorbic acid and sodium metabisulfite.

In certain embodiments, the aqueous compositions provided herein are packaged in single-dose non-reclosable containers, while in other embodiments the aqueous compositions provided herein are packaged in multiple-dose reclosable containers wherein a preservative is included in the composition.

Otic Administration

In certain embodiments pharmaceutical compositions containing at least one compound of Formula (I) are administered otically as ear drops. Such formulations are aqueous solutions that optionally contain solubilizers, stabilizers, tonicity enhancing agents, buffers and preservatives.

Combination Therapies

In certain embodiments, a compound of Formula (I) provided herein, or a pharmaceutically acceptable salt or solvate thereof, or a pharmaceutical composition containing at least one compound of Formula (I), is administered alone (without an additional therapeutic agent) for the treatment of one or more of the disease and/or disorders associated TrkA, TrkB, and TrkC kinase activity.

In other embodiments, a compound of Formula (I) provided herein, or a pharmaceutically acceptable salt or solvate thereof, or a pharmaceutical composition containing at least one compound of Formula (I) provided herein, is administered in combination with one or more additional therapeutic agents, for the treatment of one or more of the disease and/or disorders associated with TrkA, TrkB, and TrkC kinase activity.

In other embodiments, a compound of Formula (I) provided herein, or a pharmaceutically acceptable salt or solvate thereof, or a pharmaceutical composition containing at least one compound of Formula (I) provided herein, is formulated in combination with one or more additional therapeutic agents and administered for the treatment of one or more of the disease and/or disorders associated with TrkA, TrkB, and TrkC kinase activity.

In another embodiment, a compound of Formula (I) provided herein, or a pharmaceutically acceptable salt or solvate thereof, or a pharmaceutical composition containing at least one compound of Formula (I) provided herein, is administered sequentially with one or more additional therapeutic agents, for the treatment of one or more of the disease and/or disorders associated with TrkA, TrkB, and TrkC kinase activity.

In other embodiments, the combination treatments provided herein include administration of a compound of Formula (I) provided herein, or a pharmaceutically acceptable salt or solvate thereof, or a pharmaceutical composition containing a compound of Formula (I) prior to administration of one or more additional therapeutic agents, for the treatment of one or more of the disease and/or disorders associated with TrkA, TrkB, and TrkC kinase activity.

In other embodiments, the combination treatments provided herein include administration of a compound of Formula (I) provided herein, or a pharmaceutically acceptable salt or solvate thereof, or a pharmaceutical composition containing a compound of Formula (I), subsequent to administration of one or more additional therapeutic agents, for the treatment of one or more of the disease and/or disorders associated with TrkA, TrkB, and TrkC kinase activity.

In other embodiments, the combination treatments provided herein include administration of a compound of Formula (I) provided herein, or a pharmaceutically acceptable salt or solvate thereof, or a pharmaceutical composition containing a compound of Formula (I), concurrently with administration of one or more additional therapeutic agents, for the treatment of one or more of the disease and/or disorders associated with TrkA, TrkB, and TrkC kinase activity.

In the combination treatments provided herein the compound of Formula (I) may be administered separately, by the same or different route of administration, or together in the same pharmaceutical composition as the other agents.

In certain embodiments of the combination therapies described herein, the compounds of Formula (I) provided herein, or a pharmaceutically acceptable salts or solvates thereof, and the additional therapeutics agent(s) act additively. In certain embodiments of the combination therapies described herein, the compounds of Formula (I) provided herein, or a pharmaceutically acceptable salts or solvates thereof, and the additional therapeutics agent(s) act synergistically.

In other embodiments, a compound of Formula (I) provided herein, or a pharmaceutically acceptable salts or solvates thereof, or a pharmaceutical composition containing a compound of Formula (I), is administered to a patient who has not previously undergone or is not currently undergoing treatment with another therapeutic agent.

The additional therapeutic agents used in combination with at least one compound of Formula (I) provided herein, or a pharmaceutically acceptable salt or solvate thereof, include, but are not limited to chemotherapeutic agents, anti-inflammatory agents, bronchodilatory agents, antihistamine agents, decongestant agents, anti-tussive agents, antiproliferative agents, cytostatic agents, cytotoxic agents, inhibitors of polyamine biosynthesis, inhibitors of a protein kinase, inhibitors of a serine/threonine protein kinase, inhibitors of protein kinase C, inhibitors of a tyrosine protein kinase, inhibitors of EGF receptor tyrosine kinase, (e.g. Iressa®, inhibitors of VEGF receptor tyrosine kinase, (e.g. PTK787 or Avastin®), inhibitors of PDGF receptor tyrosine kinase, (e.g. STI571 (Glivec®)), a cytokine, a negative growth regulator, such as TGF-$\beta$ or IFN-$\beta$, an aromatase inhibitor (e.g. letrozole (Femara®) or anastrozole), an inhibitor of the interaction of an SH2 domain with a phosphorylated protein, antiestrogens, bisphosphonates (e.g. AREDIA® or ZOMETA®) and monoclonal antibodies (e.g. against HER2, such as trastuzumab).

The anti-inflammatory agents used in combination with at least one compound of Formula (I) described herein, or a pharmaceutically acceptable salt or solvate thereof, include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide, leukotriene antagonists including, but not limited to, zileuton, aurothioglucose, gold sodium thiomalate and auranofin, steroids including, but not limited to, alclometasone dipropionate, amcinonide, beclomethasone dipropionate, betametasone, betamethasone benzoate, betamethasone diproprionate, betamethasone sodium phosphate, betamethasone valerate, budesonide, ciclesonide, clobetasol proprionate, clocortolone pivalate, hydrocortisone, hydrocortisone derivatives, desonide, desoximatasone, dexamethasone, flunisolide, flucoxinolide, flurandrenolide, fluticasone propionate, glucocorticosteroids, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide and other anti-inflammatory agents including, but not limited to, methotrexate, colchicine, allopurinol, probenecid, thalidomide or a derivative thereof, 5-aminosalicylic acid, retinoid, dithranol or calcipotriol, sulfinpyrazone and benzbromarone.

Other anti-inflammatory agents used in combination with at least one compound of Formula (I) described herein, or a pharmaceutically acceptable salt or solvate thereof, include, but are not limited to, steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935, WO 04/26248 and WO 05/05452; LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700 and WO 04/108720; LTD4 antagonists such as montelukast, pranlukast, zafirlukast, accolate, SR2640, Wy-48,252, ICI-198615, MK-571, LY-171883, Ro 24-5913 and L-648051; dopamine receptor agonists such as cabergoline, bromocriptine, ropinirole and 4-hydroxy-7-[2-[[2-[[3-(2-phenylethoxy)-propyl]sulfonyl]ethyl]amino]ethyl]-2(3H)-benzothiazolone and pharmaceutically acceptable salts thereof (the hydrochloride being Viozan®-AstraZeneca); PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), GRC 3886 (Oglemilast, Glenmark), WO 92/19594, WO 93/19749, WO 93/19750, WO 93/19751, WO 99/16766, WO 01/13953, WO 03/104204, WO 03/104205, WO 04/000814, WO 04/000839 and WO 04/005258 (Merck), WO 04018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607, WO 04/037805, WO 04/063197, WO 04/103998, WO 04/111044, WO 05012252, WO 05012253, WO 05/013995, WO 05/030212, WO 05/030725, WO 05/087744, WO 05/087745, WO 05/087749 and WO 05/090345 as well as those described in WO 98/18796 and WO 03/39544; A2a agonists such as those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; and A2b antagonists such as those described in WO 02/42298 and WO 03/042214.

The bronchodilatory agents used in combination with at least one compound of Formula (I) described herein, or a pharmaceutically acceptable salt or solvate thereof, include, but are not limited to, beta-2 adrenoceptor agonists, anticholinergic agents, antimuscarinic agents, ipratropium bromide, oxitropium bromide, tiotropium salts, glycopyrrolate, CHF 4226 (Chiesi), SVT-40776, albuterol (salbutamol), metaproterenol, terbutaline, salmeterol, fenoterol, procaterol, formoterol, carmoterol, and GSK159797 and pharmaceutically acceptable salts thereof.

Other bronchodilatory agents used in combination with at least one compound of Formula (I) described herein, or a pharmaceutically acceptable salt or solvate thereof, include, but are not limited to, compounds (in free or salt or solvate form) of formula I of WO 0075114, preferably compounds of the Examples thereof, compounds (in free or salt or solvate form) of formula I of WO 04/16601 or of formula I of WO 04/087142, compounds, such as those described in EP 147719, EP 1440966, EP 1460064, EP 1477167, EP 1574501, JP 05025045, JP 2005187357, US 2002/0055651, US 2004/0242622, US 2004/0229904, US 2005/0133417, US 2005/5159448, US 2005/5159448, US 2005/171147, US 2005/182091, US 2005/182092, US 2005/209227, US 2005/256115, US 2005/277632, US 2005/272769, US 2005/239778, US 2005/215542, US 2005/215590, US 2006/19991, US 2006/58530, WO 93/18007, WO 99/64035, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/89892, WO 04/108675, WO 04/108676, WO 05/33121, WO 05/40103, WO 05/44787, WO 05/58867, WO 05/65650, WO 05/66140, WO 05/70908, WO 05/74924, WO 05/77361, WO 05/90288, WO 05/92860, WO 05/92887, WO 05/90287, WO 05/95328, WO 05/102350, WO 06/56471, WO 06/74897, WO 06/8173, EP 424021, U.S. Pat. Nos. 3,714,357, 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/18422, WO 04/05285, WO 04/96800, WO 05/77361 and WO 06/48225.

Dual anti-inflammatory and bronchodilatory agents used in combination with at least one compound of Formula (I) described herein, or a pharmaceutically acceptable salt or solvate thereof, include, but are not limited to, dual beta-2 adrenoceptor agonist/muscarinic antagonists such as those disclosed in US 2004/0167167, US 2004/0242622, US 2005/182092, US 2005/256114, US 2006/35933, WO 04/74246, WO 04/74812, WO 04/89892 and WO 06/23475.

The antihistamine drug substances agents used in combination with at least one compound of Formula (I) described herein, or a pharmaceutically acceptable salt or solvate thereof, include, but are not limited to, cetirizine hydrochloride, levocetirizine, acetaminophen, clemastine fumarate, promethazine, loratidine, desloratidine, diphenhydramine and fexofenadine hydrochloride, activastine, astemizole, azelastine, dimetinden, ebastine, epinastine, levocabastine, mizolastine and tefenadine as well as those disclosed in WO 03/099807, WO 04/026841 and JP 2004107299.

In certain embodiments, the additional therapeutic agent(s) used in the combination therapies described herein include, but are not limited to, non-selective cyclo-oxygenase COX-I/COX-2 inhibitors (by way of example only, piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (by way of example only, meloxicam, celecoxib, rofecoxib, valdecoxib, lumarocoxib, parecoxib and etoricoxib); glucocorticosteroids; methotrexate, lefunomide; hydroxychloroquine, d-penicillamine, auranofin or other parenteral or oral gold preparations.

Chemotherapeutic agents or other anti-proliferative agents used in combination with the compounds provided herein to treat proliferative diseases and cancer include, but are not limited to, surgery, radiotherapy (-radiation, neutron beam radiotherapy, electron beam radiotherapy, proton therapy, brachytherapy, and systemic radioactive isotopes), endocrine therapy, biologic response modifiers (interferons, interleukins, and tumor necrosis factor (TNF)), hyperthermia and cryotherapy, agents to attenuate any adverse effects (e.g., antiemetics), and other chemotherapeutic drugs, including, but not limited to, anthracyclines, alkyl sulfonates, aziridines, ethylenimines, methylmelamines, nitrogen mustards, nitrosoureas, folic acid analogs, dihydrofolate reductase inhibitor, purine analogs, pyrimidine analogs, podophyllotoxins, platinum-containing agents, interferons, interleukins, alkylating agents (mechlorethamine, chlorambucil, Cyclophosphamide, Melphalan, Ifosfamide), antimetabolites (Methotrexate, gemcitabine or capecitabine), purine antagonists and pyrimidine antagonists (6-Mercaptopurine, 5-Fluorouracil, Cytarabile, Gemcitabine), spindle poisons/microtubule active agents (Vinblastine, Vincristine, Vinorelbine, Paclitaxel, epothilone), topoisomerase I inhibitors, topoisomerase II inhibitors, podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), GLEEVEC™, adriamycin, dexamethasone, cyclophosphamide, busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elformithine, elliptinium acetate, etoglucid, etoposide, flutamide, gallium nitrate, hydroxyurea, interferon-alpha, interferon-beta, interferon-gamma, interleukin-2, lentinan, lonidamine, methotrexate, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone or combinations thereof.

Other agents used in combination with the compounds provided herein include, but are not limited to: treatments for asthma such as albuterol and SINGULAIR™; anti-inflammatory agents such as corticosteroids, TNF blockers, IL-1 RA, azathioprine, cyclophosphamide, and sulfasalazine; agents for treating blood disorders such as corticosteroids and anti-leukemic agents.

In one embodiment, the invention provides a product comprising a compound of Formula (I) and at least one other therapeutic agent as a combined preparation for simultaneous, separate or sequential use in therapy. In one embodiment, the therapy is the treatment of a disease or condition mediated by TRKA, TRKB and/or TRKC provided herein. Products provided as a combined preparation include a composition comprising the compound of Formula (I) and the other therapeutic agent(s) together in the same pharmaceutical composition, or the compound of Formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier/excipient, as described herein.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Treatment of Diseases Mediated by Kinase Activity

Compounds of Formula (I), pharmaceutically acceptable salts, solvates, N-oxides and isomers thereof, pharmaceutical compositions, and combination therapies provided herein are inhibitors of TrkA, TrkB, and TrkC kinase activity, and are useful in the treatment and/or prevention of diseases and/or disorders in which aberrant, abnormal or deregulated activity of TrkA, TrkB, and TrkC kinase contributes to the pathology and/or symptomology of such diseases and/or disorders. Such diseases and/or disorders mediated by TrkA, TrkB, and TrkC kinases are provided herein.

In certain embodiments, such diseases and/or disorders associated with TrkA, TrkB, and TrkC, kinases include, but are not limited to, cancer, proliferative diseases, pain, dermatological diseases and/or disorders, metabolic diseases and/or disorders, muscle diseases and/or disorders, neurodegenerative diseases and/or disorders, neurological diseases and/or disorders, inflammatory diseases, fibrosis, infectious diseases, respiratory diseases and/or disorders, pulmonary diseases and/or disorders and hyperplasia.

Such cancer and proliferative diseases include, but are not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gastrointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome.

Such hematopoietic disorders include, but are not limited to, myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes.

Such hematological malignancies include, but are not limited to, leukemias, myeloid leukemias, hairy cell leukemia, lymphomas (non-Hodgkin's lymphoma), Hodgkin's disease (also called Hodgkin's lymphoma), and myeloma, including, but are not limited to, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma and acute promyelocytic leukemia (APL).

Such pain disorders include, but are not limited to, cancer-related pain, skeletal pain caused by tumor metastasis, osteoarthritis, visceral pain, inflammatory pain and neurogenic pain.

Such dermatological diseases and/or disorders include, but are not limited to, inflammatory or allergic conditions of the skin, dermatitis, eczema, psoriasis, atopic dermatitis, seborrhoeic dermatitis (Dandruff, Cradle cap), diaper rash, urushiol-induced contact dermatitis, contact dermatitis, erythroderma, lichen simplex chronicus, prurigo nodularis, itch, pruritus ani, nummular dermatitis, dyshidrosis, pityriasis alba, alopecia greata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, peritoneal and sub dermal adhesion and photoaging of the skin.

Such metabolic diseases and/or disorders and eating disorder include, but are not limited to, obesity and diabetes.

Such muscle diseases and/or disorders include, but are not limited to, muscular atrophies (e.g. disuse), muscular dystrophies (e.g. Duchenne's muscle dystrophy, Beckers muscle dystrophy, Limb-Girdle muscle dystrophy), sarcopenia, cachexia, wasting and Facioscapulohumeral dystrophy.

Such neurological diseases and/or disorders and neurodegenerative disorders include, but are not limited to, impaired neurological function and Alzheimer's disease.

Such neurological diseases and/or disorders also include, but are not limited to, epilepsy.

Such inflammatory diseases and/or disorders include, but are not limited to, uveitis, atherosclerosis, atherogenesis, glomerulonephritis, Kawasaki disease, inflammatory responses, polymyositis, arthritis, neurological inflammation, chronic arthritis inflammation and osteoarthritis.

Such fibrosis diseases and/or disorders include, but are not limited to, extracellular matrix accumulation and fibrosis, scleroderma, fibrosclerosis, radiation-induced fibrosis, kidney fibrosis, lung fibrosis and liver fibrosis, haemochromatosis, primary biliary cirrhosis, restenosis, retroperitoneal fibrosis, mesenteric fibrosis, endometriosis and keloids.

Such infectious diseases and/or disorders include, but are not limited to, Chagas disease.

Such respiratory diseases and/or disorders and pulmonary disorders include, but are not limited to, asthma, bronchial asthma, allergic asthma, intrinsic (non-allergic) asthma, extrinsic (allergic) asthma, exercise-induced asthma, drug-induced asthma (including aspirin and NSAID-induced) and dust-induced asthma, chronic obstructive pulmonary disease (COPD); chronic obstructive airways disease (COAD), chronic obstructive lung disease (COLD), bronchitis, chronic bronchitis, acute bronchitis, dyspnea, arachidic bronchitis, catarrhal bronchitis, croupus bronchitis, phthinoid bronchitis, rhinitis, acute rhinitis, chronic rhinitis, rhinitis medicamentosa, vasomotor rhinitis, perennial and seasonal allergic rhinitis, rhinitis nervosa (hay fever), inflammatory or obstructive airways diseases, pulmonary hypertension, acute lung injury, adult/acute respiratory distress syndrome (ARDS), pulmonary fibrosis, idiopathic pulmonary fibrosis, chronic obstructive pulmonary disease, pulmonary disease due to infectious or toxic agents, emphysema, pneumoconiosis, aluminosis, anthracosis, asbestosis, chalicosis, ptilosis, siderosis, silicosis, tabacosis, byssinosis, acute lung injury (ALI), hypereosinophilia, LOffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, pulmonary hypertension, primary pulmonary hypertension (PPH), secondary pulmonary hypertension (SPH), familial PPH, sporadic PPH, precapillary pulmonary hypertension, pulmonary arterial hypertension (PAH), pulmonary artery hypertension, idiopathic pulmonary hypertension, thrombotic pulmonary arteriopathy (TPA), plexogenic pulmonary arteriopathy, functional classes I to IV pulmonary hypertension, and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, hypoxemia, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

In certain embodiments, the compounds of Formula (I), pharmaceutically acceptable salts, solvates, N-oxides and isomers thereof, pharmaceutical compositions, and/or combinations provided herein are used in the treatment and/or prevention of respiratory diseases and/or disorders including, but not limited to, asthma, bronchial asthma, allergic asthma, intrinsic asthma, extrinsic asthma, exercise-induced asthma, drug-induced asthma (including aspirin and NSAID-induced) and dust-induced asthma, chronic obstructive pulmonary disease (COPD); bronchitis, acute and chronic rhinitis including rhinitis medicamentosa, and vasomotor rhinitis; perennial and seasonal allergic rhinitis including rhinitis nervosa (hay fever).

In certain embodiments, the compounds of Formula (I), pharmaceutically acceptable salts, solvates, N-oxides and isomers thereof, pharmaceutical compositions, and/or combinations provided herein are used in the treatment and/or prevention of dermatological disorders including, but not limited to, psoriasis, dermatitis, eczema, atopic dermatitis, contact dermatitis, urushiol-induced contact dermatitis, eczematous dermatoses, and delayed-type hypersensitivity reactions; phyto- and photodermatitis; seborrhoeic dermatitis, dermatitis herpetiformis, lichen simplex chronicus, lichen planus, lichen sclerosus et atrophica, discoid lupus erythematosus, diaper rash, erythroderma, prurigo nodularis, itch, pruritus ani, nummular dermatitis, dyshidrosis and pityriasis alba.

In certain embodiments, the compounds of Formula (I), pharmaceutically acceptable salts, solvates, N-oxides and isomers thereof, pharmaceutical compositions, and/or combinations provided herein are used in the treatment and/or prevention of cancer including, but not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gastrointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome.

In certain embodiments, the compounds of Formula (I), pharmaceutically acceptable salts, solvates, N-oxides and isomers thereof, pharmaceutical compositions, and/or combinations provided herein are used in the treatment and/or prevention of gliomas, including but not limited to brain gliomas.

In certain embodiments, the compounds of Formula (I), pharmaceutically acceptable salts, solvates, N-oxides and isomers thereof, pharmaceutical compositions, and/or combinations provided herein are used in the treatment and/or prevention of cancer including, but not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gastrointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome. Such hematopoietic disorders include, but are not limited to, myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes. Such hematological malignancies include, but are not limited to, leukemias, myeloid leukemias, hairy cell leukemia, lymphomas (non-Hodgkin's lymphoma), Hodgkin's disease (also called Hodgkin's lymphoma), and myeloma, including, but are not limited to, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma and acute promyelocytic leukemia (APL).

Compounds of Formula (I), pharmaceutically acceptable salts, solvates, N-oxides and isomers thereof, pharmaceutical compositions, and combination therapies provided herein are used in methods for inhibiting TrkA, TrkB, and TrkC kinase activity in a subject (human or other mammal) for the treatment and/or prevention of diseases and/or disorders associated with or mediated by TrkA, TrkB, and TrkC kinase activity. In certain embodiments, such methods include administering to a subject an effective amount of a compound of Formula (I), or a pharmaceutical composition containing a compound of Formula (I).

In certain embodiments, the methods for the treatment of a subject suffering from a disease and/or disorder associated with TrkA, TrkB, and TrkC kinase activity include administering to the subject an effective amount of a compound of Formula (I), or a pharmaceutically acceptable salt, solvate thereof, either alone or as part of a pharmaceutical composition as described herein.

In certain embodiments, a compound of Formula (I), or a pharmaceutically acceptable salt or solvate thereof, is used in the preparation of a medicament for the treatment of a disease or disorder associated with TrkA, TrkB, and/or TrkC kinase activity.

In accordance with the foregoing, provided herein are methods for preventing, treating and/or ameliorating the condition of any of the diseases or disorders described above in a subject in need of such treatment, which method comprises administering to said subject a therapeutically effective amount of a compound of Formula (I), or a pharmaceutically acceptable salt thereof. For any of the methods and uses provided herein, the required dosage will vary depending on the mode of administration, the particular condition to be treated and the effect desired.

Additionally, the invention provides the use of a compound of Formula (I) in the preparation of a medicament for treating a disease or condition mediated by TrkA, TrkB, and/or TrkC kinase activity, wherein the medicament is prepared for administration with another therapeutic agent. The invention also provides the use of another therapeutic agent in the preparation of a medicament for treating a disease or condition mediated TrkA, TrkB, and/or TrkC kinase activity, wherein the medicament is administered with a compound of Formula (I).

The invention also provides a compound of Formula (I) for use in a method of treating a disease or condition mediated by TrkA, TrkB, and/or TrkC kinase activity, wherein the compound of Formula (I) is prepared for administration with another therapeutic agent. The invention also provides another therapeutic agent for use in a method of treating a disease or condition mediated by TrkA, TrkB, and/or TrkC kinase activity, wherein the other therapeutic agent is prepared for administration with a compound of Formula (I). The invention also provides a compound of Formula (I) for use in a method of treating a disease or condition mediated by TrkA, TrkB, and/or TrkC kinase activity, wherein the compound of Formula (I) is administered with another therapeutic agent. The invention also provides another therapeutic agent for use in a method of treating a disease or condition mediated by TrkA, TrkB, and/or TrkC kinase activity, wherein the other therapeutic agent is administered with a compound of Formula (I).

The invention also provides the use of a compound of Formula (I) for treating a disease or condition mediated by TrkA, TrkB, and/or TrkC kinase activity, wherein the patient has previously (e.g. within 24 hours) been treated with another therapeutic agent. The invention also provides the use of another therapeutic agent for treating a disease or condition mediated by TrkA, TrkB, and/or TrkC kinase activity, wherein the patient has previously (e.g. within 24 hours) been treated with a compound of Formula (I).

Kits

In one embodiment, the invention provides a kit comprising two or more separate pharmaceutical compositions, at least one of which contains a compound of Formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

EXAMPLES

The following examples are offered to illustrate, but not to limit, synthetic methods of compounds of Formula (I). Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art, including:
BOC tertiary butyl carboxy
br broad
d doublet
dd doublet of doublets
DCM dichloromethane
DIEA diethylisopropylamine
DMF N,N-dimethylformamide
DMSO dimethylsulfoxide
DTT dithiothreitol
ESI electrospray ionization
EtOAc ethyl acetate
HATU 2-(1H-7-Azabenzotriazol-1-yl)-1,1,3,3-tetramethyl uronium hexafluorophosphate Methanaminium
HPLC high pressure liquid chromatography
LCMS liquid chromatography and mass spectrometry
MeOH methanol
MS mass spectrometry
m multiplet
mL milliliter(s)
m/z mass to charge ratio
NMR nuclear magnetic resonance ppm parts per million rac racemic s singlet t triplet TFA trifluoroacetic acid THF tetrahydrofuran All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Synthesis of Intermediates

Synthesis of (2R,4S)-4-fluoro-2-(3-fluorophenyl) pyrrolidine (I-6)

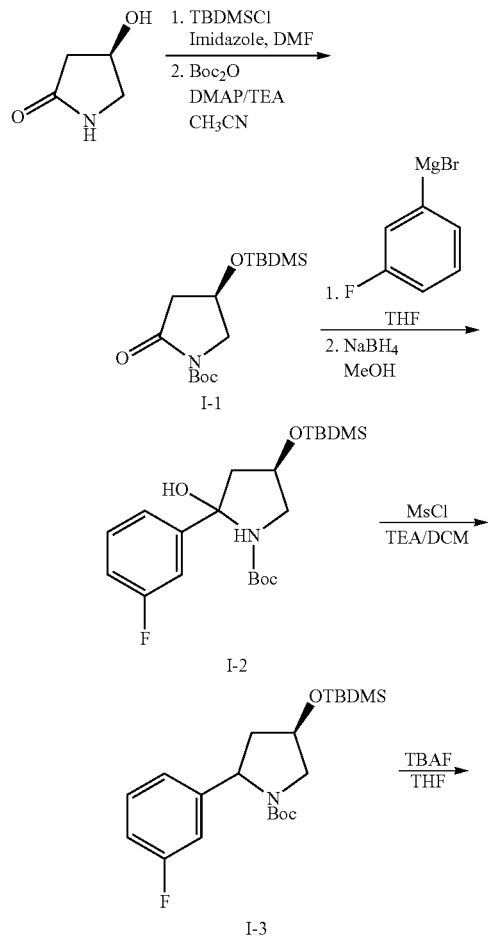

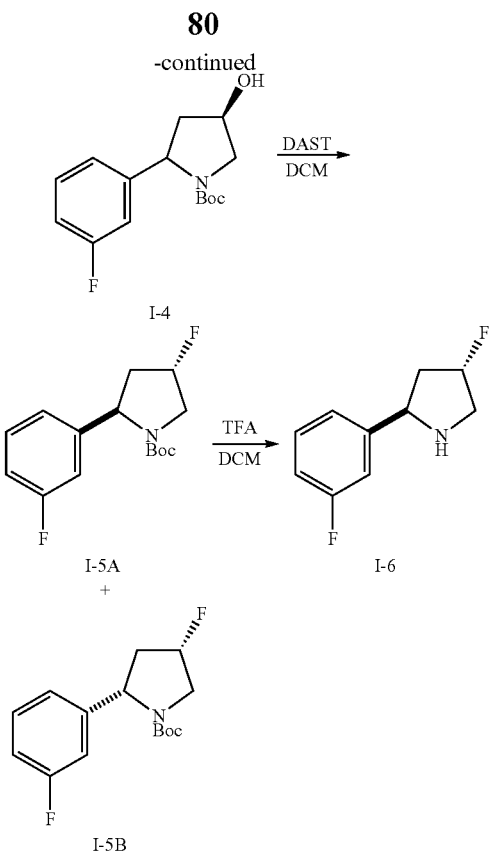

To a solution of (R)-4-hydroxypyrrolidin-2-one (5.0 g, 49.5 mmol) in DMF (25 mL) at 0° C. was added TBDMSCI (7.8 g, 52 mmol) and imidazole (5.1 g, 74.3 mmol). The reaction was warmed to room temperature and stirred for 3 hours. The mixture was poured into water and the resulting precipitate was filtered and dried under vacuum overnight to yield (R)-tert-butyl 4-((tert-butyldimethylsilyl)oxy)-2-oxopyrrolidine-1-carboxylate. $^1$H NMR (400 MHz, CDCl$_3$) δ 5.80 (bs, 1 H), 4.56 (m, 1 H), 3.60 (dd, J=4.0, 6.6 Hz, 1 H), 3.24 (dd, J=3.3, 10.0 Hz, 1 H), 2.55 (dd, J=6.6, 16.0 Hz, 1 H), 2.57 (dd, J=4.2, 16.0 Hz, 1 H), 0.89 (s, 9 H), 0.07 (s, 6H). MS m/z 238.1 (M+23)$^+$.

To a solution of (R)-tert-butyl 4-((tert-butyldimethylsilyl)oxy)-2-oxopyrrolidine-1-carboxylate (10.9 g, 50.7 mmol) in CH$_3$CN (100 mL) at 0° C. under N$_2$ was added TEA (8.5 mL, 61 mmol), DMAP (3.1 g, 25.45 mmol) and di-tert-butyl dicarbonate (14.4 g, 66.2 mmol). The mixture was warmed to room temperature and stirred overnight. The mixture was poured into water and extracted with EtOAc. The organic layer was separated, washed with 1 N HCl, 1 N NaOH and brine, dried over sodium sulfate, filtered and concentrated to yield (R)-tert-butyl 4-(tert-butyldimethylsilyloxy)-2-oxopyrrolidine-1-carboxylate (I-1). $^1$H NMR (400 MHz, CDCl$_3$) δ 4.40 (m, 1 H), 3.88 (dd, J=4.0, 6.5 Hz, 1 H), 3.64 (dd, J=4.0, 10.0 Hz, 1 H), 2.73 (dd, J=6.0, 16.0 Hz, 1 H), 2.48 (dd, J=4.0, 16.0 Hz, 1 H), 1.57 (s, 9 H), 0.89 (s, 9 H), 0.09 (s, 6 H). MS m/z 338.1 (M+23)$^+$.

To a solution of (R)-tert-butyl 4-(tert-butyldimethylsilyloxy)-2-oxopyrrolidine-1-carboxylate (I-1) (13.6 g, 43.2 mmol) in THF (100 mL) at 0° C. under N$_2$ was added (3-fluorophenyl)magnesium bromide (52 mL of 1 M solution in THF, 51.84 mmol) over 1 hour. The reaction mixture was stirred at 0° C. for 1 hour. Methanol (80 mL) was added to the mixture followed by NaBH$_4$ (2.45 g, 64.8 mmol) at 0° C. The mixture was stirred at 0° C. for 1 hour then poured into 10% aqueous NH₄Cl. The mixture was extracted with EtOAc, washed with brine, dried over sodium sulfate, filtered and concentrated. The crude product was purified by column chromatography on silica gel with EtOAc/hexanes gradient as eluant to yield tert-butyl (2R)-2-(tert-butyldimethylsilyloxy)-4-(3-fluorophenyl)-4-hydroxybutylcarbamate (I-2). ¹H NMR (400 MHz, CDCl₃) δ 7.33-7.28 (m, 1 H), 7.13-7.09 (m, 2 H), 6.98-6.92 (m, 1 H), 4.97-4.90 (m, 1 H), 4.82 (bs, 1 H), 4.12-4.06 (m, 1 H), 3.42-3.33 (m, 1 H), 3.22-3.17 (m, 1 H), 1.88-1.84 (m, 2 H), 1.47 (s, 9 H), 0.93 (s, 9 H), 0.11 (s, 6 H). MS m/z 436.1 (M+23)⁺.

To a solution of tert-butyl (2R)-2-(tert-butyldimethylsilyloxy)-4-(3-fluorophenyl)-4-hydroxybutylcarbamate (I-2) (15.8 g, 38.2 mmol) in DCM (120 mL) at −60° C. under N₂ was added TEA (16 mL, 114.6 mmol) and MsCl (3.3 mL, 42.0 mmol). The resulting mixture was stirred at −60° C. for 1 hour. The reaction was poured into water, washed with brine, dried over sodium sulfate, filtered and concentrated to yield (4R)-tert-butyl 4-(tert-butyldimethylsilyloxy)-2-(3-fluorophenyl)pyrrolidine-1-carboxylate (I-3). MS m/z 418.1 (M+23)⁺.

To a solution of (4R)-tert-butyl 4-(tert-butyldimethylsilyloxy)-2-(3-fluorophenyl)pyrrolidine-1-carboxylate (I-3) (18.1 g, 38.2 mmol) in THF (76 mL) at room temperature was added TBAF (50 mL of a 1.0 M solution in THF, 49.7 mmol). The mixture was stirred at room temperature for 2 hours then poured into water. The mixture was extracted with EtOAc, washed with water and brine, dried over sodium sulfate, filtered and concentrated. The mixture was purified by column chromatography on silica gel with EtOAc/hexanes gradient as eluant to yield (4R)-tert-butyl 2-(3-fluorophenyl)-4-hydroxypyrrolidine-1-carboxylate (1-4). ¹H NMR (400 MHz, CDCl₃) δ 7.32-7.26 (m, 1 H), 7.07 (bd, J=7.6 Hz, 1 H), 7.01 (bd, J=7.5 Hz, 1 H), 6.92 (dt, J=8.4 Hz, 1 H), 4.83 (bs, 1 H), 4.50 (q, J=5.2 Hz, 1 H), 3.89 (bs, 1 H), 3.58 (ddd, J=1.2, 3.6, 12.0 Hz, 1 H), 2.62 (bs, 1 H), 2.0 (dt, J=4.4, 17.6 Hz, 1 H), 1.23 (s, 6 H). MS m/z 304.1 (M+23)⁺.

NOTE: In some instinces the two diasteromers were separated by column chromatography on silica gel with EtOAc/hexanes gradient as eluant to yield (2R,4R)-tert-butyl 2-(3-fluorophenyl)-4-hydroxypyrrolidine-1-carboxylate (I-4A) and (2S,4R)-tert-butyl 2-(3-fluorophenyl)-4-hydroxypyrrolidine-1-carboxylate (I-4B). However, better resolution was achieved in the subsequent step.

To a solution of (4R)-tert-butyl 2-(3-fluorophenyl)-4-hydroxypyrrolidine-1-carboxylate (I-4) (2.7 g, 9.6 mmol) in DCM (25 mL) in a plastic bottle at −78° C. was added DAST (2.5 mL, 19.2 mmol). The mixture was stirred at −78° C. for 2 hours and then was warmed slowly to room temperature overnight. The mixture was added drop wise to aqueous NaHCO₃ at 0° C. and was extracted with DCM. The organic layers were combined, washed with brine, dried over sodium sulfate, filtered and concentrated. The two diasteromers were separated by column chromatography on silica gel with EtOAc/hexanes gradient as eluant to yield (2R,4S)-tert-butyl 4-fluoro-2-(3-fluorophenyl)pyrrolidine-1-carboxylate (I-5A) (first eluting compound) and (2S,4S)-tert-butyl 4-fluoro-2-(3-fluorophenyl)pyrrolidine-1-carboxylate (I-5B). ¹H NMR (400 MHz, CDCl₃) δ 7.21 (dd, J=6.0, 6.0 Hz, 1 H), 6.92 (bd, J=8.0 Hz, 1 H), 6.88-6.82 (m, 2 H), 5.20 (bd, J=52.0 Hz, 1 H), 4.80 (bs, 1 H), 4.02 (dd, J=13.6, 22.8 Hz, 1 H), 3.65 (dd, J=12.8, 38.4 Hz, 1 H), 2.67-2.56 (m, 1 H), 1.89 (dt, J=11.2, 42 Hz, 1 H), 1.09 (s, 6 H). MS m/z 284.1 (M+1)⁺.

To a solution of (2R,4S)-tert-butyl 4-fluoro-2-(3-fluorophenyl)pyrrolidine-1-carboxylate (I-5A) (890 mg, 3.14 mmol) in DCM (5 mL) at room temperature was added TFA (5 mL). The mixture was stirred at room temperature for 2 hours. All the solvents were removed under reduced pressure. The crude was extracted with EtOAc, washed with aqueous NaHCO₃ and brine, dried over sodium sulfate, filtered and concentrated to yield (2R,4S)-4-fluoro-2-(3-fluorophenyl) pyrrolidine (I-6). ¹H NMR (400 MHz, CDCl₃) δ 7.31-7.25 (m, 1 H), 7.15-7.10 (m, 2 H), 6.96-6.90 (m, 1 H), 5.29 (d, J=53.6 Hz 1 H), 4.50 (dd, J=9.6, 6.4 Hz, 1 H), 3.43-3.33 (m, 1 H), 3.31-3.28 (m, 1 H), 2.51 (ddd, J=21.2, 14.0, 6.4 Hz, 1 H), 2.23 (bs, 1 H), 1.79 (dddd, J=39.6, 14.4, 10.0, 4.4 Hz, 1 H). MS m/z 184.1 (M+1)⁺.

Synthesis of (R)-4,4-difluoro-2-(3-fluorophenyl) pyrrolidine (I-9)

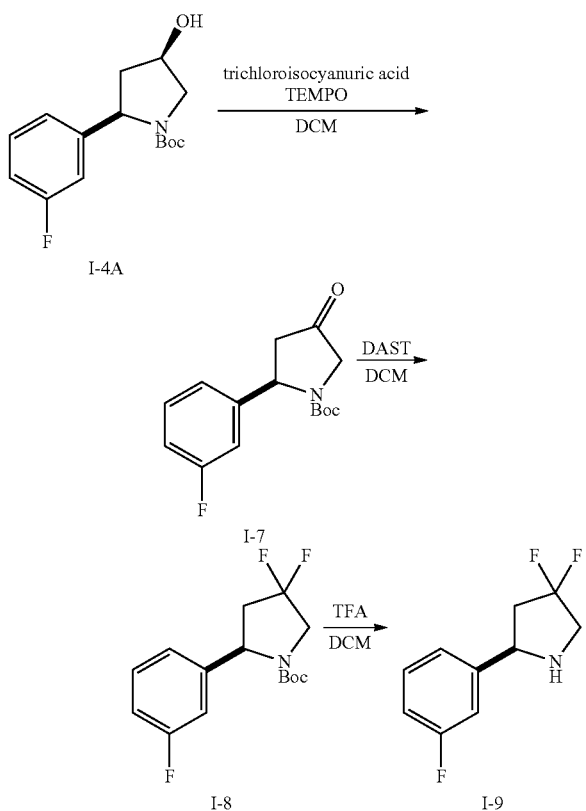

To a solution of (2R,4R)-tert-butyl 2-(3-fluorophenyl)-4-hydroxypyrrolidine-1-carboxylate (I-4A) (1.4 g, 5.0 mmol) and trichloroisocyanuric acid (1.2 g, 5.0 mmol) in DCM (70 mL) at −10° C. was added 2,2,6,6-tetramethylpiperidine-1-oxyl (TEMPO) (0.08 g, 0.5 mmol). The mixture was stirred at −10° C. for 15 minutes, then to room temperature over 1 hour and subsequently poured into cold aqueous NaHCO₃ containing ice while stirring. The organic layer was separated, washed with brine, dried over sodium sulfate, filtered and reduced to dryness to yield (R)-tert-butyl 2-(3-fluorophenyl)-4-oxopyrrolidine-1-carboxylate (I-7) as a light yellow oil. ¹H NMR (400 MHz, CD₃OD) δ 7.40 (q, J=7.6 Hz, 1 H), 7.01 (d, J=7.6 Hz, 1 H), 7.03-6.99 (m, 2 H), 5.34 (bs, 1 H), 4.07-3.91 (m, 2 H), 3.30 (dd, J=18.8, 10.0 Hz, 1 H), 2.50 (dd, J=18.8, 3.2 Hz, 1 H), 1.31 (bs, 9 H). MS m/z 224.1 (M−56)⁺.

To a solution of (R)-tert-butyl 2-(3-fluorophenyl)-4-oxopyrrolidine-1-carboxylate (I-7) (1.3 g, 4.8 mmol) in DCM (15 mL) in a plastic bottle at −78° C. was added DAST (1.9 mL, 14.4 mmol) drop wise. The resulting orange homogeneous solution was stirred at −78° C. for 30 minutes. The solution was warmed to room temperature and continued to stir for an additional 2 hours. The resulting solution was poured into stirring ice water (100 mL) and agitated for 15 minutes then extracted with DCM (3×50 mL). The combined organic extracts were dried over sodium sulfate, filtered and reduced to dryness. The crude product was purified by flash column chromatography on silica gel with hexanes/EtOAc gradient as eluant to yield (R)-tert-butyl 4,4-difluoro-2-(3-fluorophenyl)pyrrolidine-1-carboxylate (I-8) as a light yellow oil. $^1$H NMR (400 MHz, CD$_3$OD) δ 7.39 (q, J=7.6 Hz, 1 H), 7.11 (d, J=7.6 Hz, 1 H), 7.04-6.99 (m, 2 H), 5.03 (bs, 1 H), 4.02-3.89 (m, 2 H), 2.99-2.86 (m, 1 H), 2.39-2.28 (m, 1 H), 1.20 (bs, 9 H). MS m/z 246.1 (M−56)$^+$.

C. and aqueous NaHCO$_3$ was added while rapidly stirring. The organic phase was separated and washed with aqueous NaHCO$_3$, dried over anhydrous sodium sulfate, filtered and reduced to dryness to yield (R)-4,4-difluoro-2-(3-fluorophenyl)pyrrolidine (I-9) as a light yellow oil that crystallizes on standing. $^1$H NMR (400 MHz, CD$_3$OD) δ 7.40 (q, J=8.0 Hz, 1 H), 7.23 (d, J=8.8 Hz, 1 H), 7.20 (d, J=10.0 Hz, 1 H), 7.05 (dt, J=8.8, 2.4 Hz, 1 H), 4.41 (dd, J=10.4, 7.2 Hz, 1 H), 3.48 (q, J=12.0 Hz, 1 H), 3.30 (q, J=15.2 Hz, 1 H), 2.74-2.63 (m, 1 H), 2.29-2.14 (m, 1 H). MS m/z 202.1 (M+1)$^+$.

Synthesis of 3-fluoro-5-((2R,4S)-4-fluoropyrrolidin-2-yl)benzonitrile (I-15)

Method A

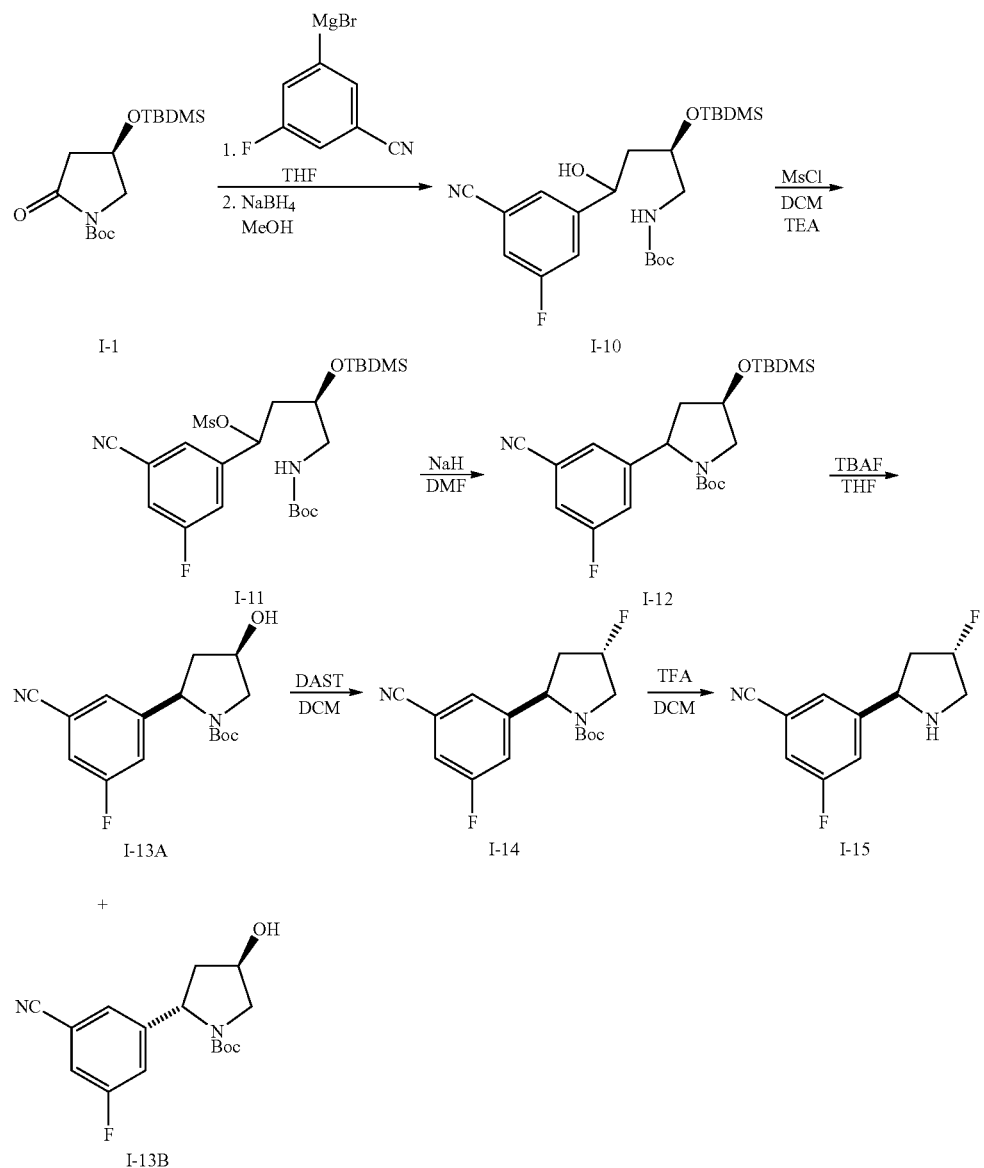

To a solution of (R)-tert-butyl-4,4-difluoro-2-(3-fluorophenyl)pyrrolidine-1-carboxylate (I-8) (0.9 g, 3.0 mmol) in DCM (20 mL) was added TFA (2 mL, 27 mmol) and stirred at room temperature for 2 hours. The reaction was cooled to 0°

To a solution of 3-bromo-5-fluorobenzonitrile (5.2 g, 0.26 mmol) in THF (26 mL) at −78° C. was slowly added isopropylmagnesium chloride (13.6 mL of a 2.0 M solution in diethyl ether, 0.27 mmol). The mixture was warmed and stirred at −30° C. for 1 hour then cooled to −78° C. The resulting aryl Grignard was added to a solution of (R)-tert-butyl 4-(tert-butyldimethylsilyloxy)-2-oxopyrrolidine-1-carboxylate (I-1) (7.8 g, 25 mmol) in THF (25 mL) at −78° C. The reaction mixture was stirred at 0° C. for 30 minutes. Methanol (20 mL) was added to the reaction mixture followed by NaBH$_4$ (1.4 g, 37 mmol). The mixture was stirred to room temperature for 12 hours then poured into 10% aqueous NH$_4$Cl. The mixture was extracted with EtOAc, washed with brine, dried over sodium sulfate, filtered and concentrated. The crude product was purified by column chromatography on silica gel with EtOAc/hexanes gradient as eluant to yield tert-butyl ((2R)-2-((tert-butyldimethylsilyl)oxy)-4-(3-cyano-5-fluorophenyl)-4-hydroxybutyl)carbamate (I-10). $^1$H NMR (400 MHz, CDCl$_3$) δ 7.47 (s, 1 H), 7.38-7.33 (m, 1 H), 7.25-7.20 (m, 1 H), 4.95 (d, J=9.2 Hz, 1 H), 4.81 (bs, 1 H), 4.12-4.05 (m, 1 H), 3.76 (bs, 1 H), 3.45-3.35 (m, 1 H), 3.23-3.12 (m, 1 H), 1.87-1.71 (m, 2 H), 1.45 (s, 9 H), 0.91 (s, 9 H), 0.12 (s, 6 H). MS m/z 461.2 (M+23)$^+$.

To a solution of tert-butyl ((2R)-2-((tert-butyldimethylsilyl)oxy)-4-(3-cyano-5-fluorophenyl)-4-hydroxybutyl)carbamate (I-10) (5.3 g, 12.1 mmol) in DCM (50 mL) at −60° C. was added TEA (5.1 mL, 36.3 mmol) and MsCl (0.98 mL, 12.2 mmol). The resulting mixture was stirred at −60° C. for 2 hours. The reaction was poured into water, diluted with DCM and washed with brine, dried over sodium sulfate, filtered and concentrated. The crude product was purified by column chromatography on silica gel with EtOAc/hexanes gradient as eluant to yield (3R)-4-((tert-butoxycarbonyl)amino)-3-((tert-butyldimethylsilyl)oxy)-1-(3-cyano-5-fluorophenyl)butyl methanesulfonate (I-11). MS m/z 539.1 (M+23)$^+$. Compound decomposed on standing. Used immediately in next reaction without delay.

To a solution of (3R)-4-((tert-butoxycarbonyl)amino)-3-((tert-butyldimethylsilyl)oxy)-1-(3-cyano-5-fluorophenyl)butyl methanesulfonate (I-11) (5.3 g, 10.3 mmol) in DMF (30 mL) at 0° C. was added NaH (0.43 mg of a 60% mineral oil dispersion, 10.8 mmol). The reaction was stirred at room temperature for 12 hours. The reaction was quenched with water and extracted with EtOAc, washed with brine, dried over sodium sulfate, filtered and concentrated. The crude product was purified by column chromatography on silica gel with EtOAc/hexanes gradient as eluant to yield (4R)-tert-butyl 4-((tert-butyldimethylsilyl)oxy)-2-(3-cyano-5-fluorophenyl)pyrrolidine-1-carboxylate (I-12). $^1$H NMR (400 MHz, CDCl$_3$) δ 7.38 (s, 1 H), 7.33-7.20 (m, 1 H), 7.20-7.12 (m, 1 H), 4.90 (dd, J=7.6, 56.2 Hz, 1 H), 4.45-4.39 (m, 1 H), 3.78-3.65 (m, 1 H), 3.52 (dd, J=11.2, 36.8 Hz, 1 H), 2.56-2.41 (m, 1 H), 1.89 (t, J=13.2 Hz, 1 H), 1.47 (s, 4 H), 1.23 (s, 5 H), 0.75 (d, J=7.6 Hz, 9 H), 0.03 (s, 3 H), −0.08 (d, J=10.8 Hz, 3 H). MS m/z 443.2 (M+23)$^+$.

To a solution of (4R)-tert-butyl 4-((tert-butyldimethylsilyl)oxy)-2-(3-cyano-5-fluorophenyl)pyrrolidine-1-carboxylate (I-12) (2.7 g, 6.4 mmol) in THF (25 mL) at room temperature was added TBAF (7.1 mL of a 1.0 M solution in THF, 7.0 mmol). The mixture was stirred at room temperature for 1 hour then concentrated. The mixture was purified by column chromatography on silica gel with EtOAc/hexanes gradient as eluant to yield the desired isomer (2R,4R)-tert-butyl 2-(3-cyano-5-fluorophenyl)-4-hydroxypyrrolidine-1-carboxylate (I-13A) and (2S,4R)-tert-butyl 2-(3-cyano-5-fluorophenyl)-4-hydroxypyrrolidine-1-carboxylate (I-13B). $^1$H NMR (400 MHz, CDCl$_3$) δ 7.41 (s, 1 H), 7.35-7.26 (m, 1 H), 7.24-7.16 (m, 1 H), 4.89 (d, J=48.8 Hz, 1 H), 4.56-4.50 (m, 1 H), 3.85-3.70 (m, 1 H), 3.66-3.55 (m, 1 H), 2.59 (bs, 1 H), 2.00-1.90 (m, 1 H), 1.45 (bs, 3 H), 1.22 (bs, 6 H). MS m/z 304.1 (M+23)$^+$.

To a solution of (2R,4R)-tert-butyl 2-(3-cyano-5-fluorophenyl)-4-hydroxypyrrolidine-1-carboxylate (I-13A) (0.7 g, 2.3 mmol) in DCM (4 mL) in a plastic bottle at −78° C. was added DAST (0.6 mL, 4.6 mmol). The reaction was stirred at −78° C. for 2 hours and then loaded directly onto silica gel and purified by column chromatography with EtOAc/hexanes gradient as eluant to yield (2R,4S)-tert-butyl 2-(3-cyano-5-fluorophenyl)-4-fluoropyrrolidine-1-carboxylate (I-14). $^1$H NMR (400 MHz, CDCl$_3$) δ 7.35 (s, 1 H), 7.30-7.16 (m, 2 H), 5.25 (d, J=52.0 Hz, 1 H), 5.06-4.86 (m, 1 H), 4.20-3.98 (m, 1 H), 3.72 (dd, J=11.6, 38.8 Hz, 1 H), 2.80-2.66 (m, 1 H), 2.06-1.78 (m, 1 H), 1.45 (bs, 3 H), 1.19 (bs, 6 H). MS m/z 331.1 (M+23)$^+$.

To a solution of (2R,4S)-tert-butyl 2-(3-cyano-5-fluorophenyl)-4-fluoropyrrolidine-1-carboxylate (I-14) (0.6 g, 1.95 mmol) in DCM (2 mL) at room temperature was added TFA (2 mL). The mixture was stirred at room temperature for 2 hours. All the solvents were removed under reduced pressure. The crude was diluted with EtOAc, washed with aqueous NaHCO$_3$ and brine, dried over sodium sulfate, filtered and concentrated to yield 3-fluoro-5-((2R,4S)-4-fluoropyrrolidin-2-yl)benzonitrile (I-15). $^1$H NMR (400 MHz, CDCl$_3$) δ 7.52 (s, 1 H), 7.43-7.37 (m, 1 H), 7.24-7.20 (m, 1 H), 5.28 (dt, J=3.6, 53.6 Hz, 1 H), 4.57 (dd, J=6.4, 9.6 Hz, 1 H), 3.44-3.18 (m, 2 H), 2.63-2.50 (m, 1 H), 1.72 (dddd, J=4.4, 10.0, 14.4, 39.6 Hz, 1H). MS m/z 209.1 (M+1)$^+$.

Method B

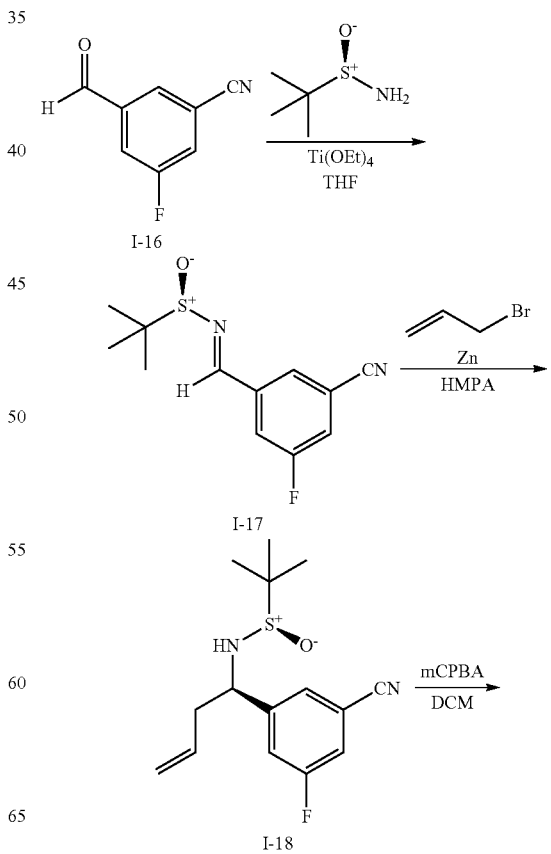

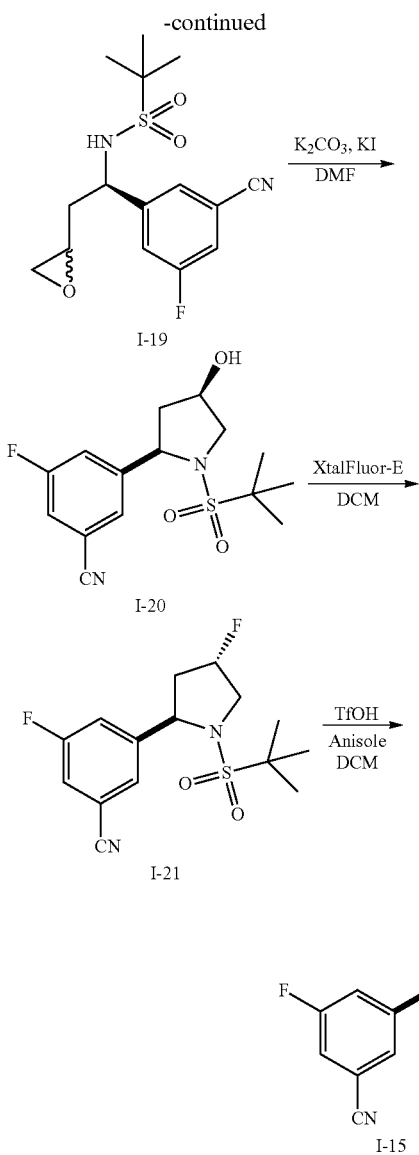

bromide (242.5 g, 2.0 mol). The mixture was stirred at room temperature over 40 minutes. A slow exotherm started from 22.5° C. to 27° C. while stirring at room temperature over this 40 minute period. (Note: The batch temperature was controlled with a water bath). When the mixture reached 27° C. it was cooled back to 24.5° C. Over the next 30 minutes the batch temperature exothermed to 25.2° C. HPLC analysis was used to monitor the reaction. Additional zinc (53 g, 0.81 mol) and allyl bromide (97 g, 0.80 mol) were added at 22.5° C. Immediately after the reagents were charged the batch temperature dropped to 22.3° C. and approximately 20 minutes after the reagents were charged a slow exotherm to 28° C. began. This exotherm reached 28° C. 1 hour after the reagents were added. The batch temperature was readjusted to 26.5° C. using a water bath (bath temperature 18° C.). The mixture was stirred 1 hour at 26.5° C. $H_2O$ (4.2 L) was added over 15 minutes to give an exotherm from 18 to 23° C. using an ice water bath (bath temperature 4° C.). (Note: The water addition caused a significant evolution of propylene gas). TBME (4 L) was added to the mixture followed by 10% citric acid (~2.1 L) to obtain a clear biphasic mixture (aqueous layer pH~3). The mixture was stirred 20 minutes at 23° C. and the aqueous layer was removed. The organic layer was washed with brine (900 mL, containing 45 mL 10% citric acid) and water (2×900 mL). The organic layer was concentrated under vacuum (150 to 5 torr) at a bath temperature of 30° C. to give an orange waxy solid. The waxy solids were triturated at 23° C. using 4 volumes of heptane to yield (R)-N-((R)-1-(3-cyano-5-fluorophenyl)but-3-en-1-yl)-2-methylpropane-2-sulfinamide (I-18). Melting point: 38-40° C. $^1$H NMR (400 MHz, $CDCl_3$) δ 7.43 (S, 1 H), 7.27-7.34 (m, 2 H), 5.56-5.62 (m, 1 H), 5.04-5.12 (m, 2 H), 4.46-4.51 (m, 1 H), 3.61-3.62 (m, 1 H), 2.69-2.73 (m, 1 H), 2.52-2.55 (m, 1 H), 1.23 (s, 9 H).

A 22 L 4 neck round bottom flask was charged with (R)-N-((R)-1-(3-cyano-5-fluorophenyl)but-3-enyl)-2-methylpropane-2-sulfinamide (I-18) (441 g, 1.5 mol) and DCM (6 L). The solution was cooled to <0° C. and mCPBA (737 g, 3.0 mol) was added in portions over 60 minutes at a batch temperature <10° C. (Note: a mild exotherm and gas evolution were observed. A white suspension was obtained after the addition). The reaction mixture was stirred at 0-10° C. over 20 minutes and warmed to room temperature and stirred at room temperature for 3 hours. Additional mCPBA (387.5 g, 1.54 mol) was added and the mixture was stirred at room temperature for an additional 18 hours. The reaction was monitored by HPLC until deemed complete. The mixture was cooled to <10° C. and water (7.3 L) was added to the reaction mixture. (Note: exotherm from 5° C. to 12° C.) A saturated $K_2CO_3$ solution (1.94 L) was added until pH~9.0 was reached. (Note: A suspension was initially obtained and a biphasic solution was obtained after stirring). The DCM layer was separated and to it was added 10% sodium bisulfite solution (2.9 L) over 15 minutes at 4 to 9° C. (aqueous layer pH 3-4). The mixture was stirred 30 minutes at 9 to 12° C. and the DCM layer was then washed with a mixture of brine (3 L) and aqueous saturated $NaHCO_3$ (2 L) (aqueous layer pH=7). Aqueous saturated $K_2CO_3$ (150 mL) was added until pH=8.5 at 10 to 16° C. The DCM solution was concentrated under vacuum (250 to 50 torr) at 25° C. to give N-((1R)-1-(3-cyano-5-fluorophenyl)-2-(oxiran-2-yl)ethyl)-2-methylpropane-2-sulfonamide (I-19) as an oil (as a mixture of diastereoisomers). $^1$H NMR (400 MHz, $CDCl_3$) δ 748-7.50 (m, 1 H), 7.30-7.40 (m, 1 H), 7.28-7.29 (m, 1 H), 5.28-5.37 (m, 1 H), 4.77-4.88 (m, 1 H), 2.89-3.00 (m, 1 H), 2.79-2.85 (m, 1 H), 2.48-2.62 (m, 1 H), 2.21-2.31 (m, 1 H), 1.86-1.84 (m, 1 H), 1.36 (s, 9 H).

A 22 L 4 neck round bottom flask was charged with N-((1R)-1-(3-cyano-5-fluorophenyl)-2-(oxiran-2-yl)ethyl)-

A 22 L round bottom flask was charged with (R)-2-methylpropane-2-sulfinamide (400 g, 3.3 mol) and 3-fluorobenzaldehyde (I-16) (447 g, 3.0 mol) in THF (1877 mL). $Ti(OEt)_4$ (890 g, 3.9 mol) was added over 40 minutes at 9-15° C. cooling with an ice bath as required. The mixture was stirred at room temperature over 19 hours. HPLC analysis was used to monitor the reaction. The mixture was cooled to 0 to 10° C. EtOAc (7.5 L) was added to the mixture followed by brine (2.0 L) and the resulting slurry was allowed to stir at 10 to 20° C. for 20 minutes. The slurry was filtered through a pad of celite. The top organic layer was concentrated under vacuum (100 to 10 torr) at a bath temperature of 35° C. to give an orange solid which was placed in trays and dried in a vacuum oven (5 torr) at 25° C. for 20 hours to give (R,E)-N-(3-cyano-5-fluorobenzylidene)-2-methylpropane-2-sulfinamide (I-17). Melting point: 93-99° C. $^1$H NMR (400 MHz, $CDCl_3$) δ 8.56 (S, 1 H), 7.94 (S, 1 H), 7.79 (dd, 1 H), 7.50 (dd, 1 H).

A 22 L round bottom flask was charged with (R,E)-N-(3-cyano-5-fluorobenzylidene)-2-methylpropane-2-sulfinamide (I-17) (337.5 g, 1.33 mol), anhydrous HMPA (4200 mL), $H_2O$ (25.5 g, 1.4 mol), zinc (132.8 g, 2.04 mol), and allyl 2-methylpropane-2-sulfonamide (I-19) (440.6 g, 1.35 mol), DMF (3200 mL), KI (224.1 g, 1.35 mol) and K$_2$CO$_3$ (558.9 g, 4.04 mol). The mixture was stirred for 16 hours at 20° C. then heated to 86.6° C. and held at this temperature for 1 hour. HPLC analysis of the reaction mixture showed all of (I-19) was consumed. The reaction was cooled to <20° C. and water (6.4 L) was slowly added at 11 to 19° C. followed by i-PrOAc (4.5 L). The i-PrOAc layer was separated and washed with water (3 L) and brine (3 L). The i-PrOAc layer was concentrated to dryness at a bath temperature of 30° C. under vacuum (150 to 10 torr) to give 441 g of a brown solid. The brown solid (220.5 g) was taken up in DCM and purified using a Biotage Flash 150 unit. The Flash 150 was fitted with a 150 L (5 kg) cartridge which was equilibrated with a 1:1 (v/v) mixture of EtOAc/heptane. The crude sample was loaded onto the column with N$_2$ pressure and rinsed with DCM (500 mL). The column was eluted with EtOAc/heptane (1:1) and the desired product eluted in fractions 14 to 20 (1.5 L fractions). These fractions were combined and evaporated under vacuum at a bath temperature of 35° C. to give 3-((2R,4R)-1-(tert-butylsulfonyl)-4-hydroxypyrrolidin-2-yl)-5-fluorobenzonitrile (I-20) as a white solid. Melting point: 93-96° C. $^1$H NMR (400 MHz, CDCl$_3$) δ 7.64 (s, 1 H), 7.51 (d, 1 H), 7.27 (d, 1 H), 5.20-5.23 (m, 1 H), 4.62-4.64 (m, 1 H), 4.06-4.08 (m, 1 H), 3.38-3.41 (m, 1 H), 2.69-2.71 (m, 1 H), 2.15 (brs, 1 H), 1.98 (s, 9 H).

A 22 L flask was charged with 3-((2R,4R)-1-(tert-butylsulfonyl)-4-hydroxypyrrolidin-2-yl)-5-fluorobenzonitrile (I-20) (232 g, 0.71 mol) and DCM (4600 mL). The mixture was cooled to −50° C. and Et$_3$N.3HF (232 g, 1.4 mol) was added and stirred for 10 minutes XtalFluor-E (247 g, 1.0 mol) was then added in one portion.
(Note: exotherm from −52.1 to −48.5° C. observed.) The reaction mixture was allowed to warm to 0° C. over ~2 hours. The reaction was monitored by HPLC until (I-20) was consumed. The reaction was cooled to −10° C. and DCM (2350 mL) was added followed by slow addition of aqueous 5% NaHCO$_3$ solution (5870 mL). The aqueous layer was separated and extracted with DCM (1170 mL) and the combined organic layers were concentrated to dryness under vacuum at 35° C. to give a tan solid (224 g). The crude solid was triturated at 20° C. with EtOAc (605 mL) and the resulting white solid was filtered and air dried to give a first crop of 3-((2R,4S)-1-(tert-butylsulfonyl)-4-fluoropyrrolidin-2-yl)-5-fluorobenzonitrile (I-21). The EtOAc trituant was concentrated and triturated a 2nd time with fresh EtOAc to give a 2nd crop of (I-21). The process was repeated to give 3rd crop of (I-21). Melting point: 182-184° C. $^1$H NMR (400 MHz, CDCl$_3$) δ 7.43 (s, 1 H), 7.26-7.30 (m, 2 H), 5.22-5.36 (m, 2 H), 4.21-4.30 (m, 1 H), 3.55-3.68 (m 1 H), 2.79-2.85 (m, 1 H), 2.00-2.13 (m, 1 H), 1.24 (s, 9 H).

A 12 L flask was charged with DCM (3350 mL) and TfOH (433.3 g, 2.9 mol). The mixture was cooled to −30° C. and anisole (156 g, 1.4 mol) was added followed by slow addition of a solution of 3-((2R,4S)-1-(tert-butylsulfonyl)-4-fluoropyrrolidin-2-yl)-5-fluorobenzonitrile (I-21) (316 g, 0.96 mol) in DCM (1610 mL) while maintaining the temperature between −16° C. and −12° C. The addition required ~35 minutes. The mixture was warmed to −2° C. and a sample analysis by HPLC showed consumption of (I-21). The reaction was cooled to −10° C. and DCM (2.4 L) was added followed by an aqueous saturated K$_2$CO$_3$ (1.0 L) at −3 to 3° C. Water (1.5 L) was added and stirred for 30 minutes to dissolve the insoluble material. The aqueous layer was separated and extracted with i-PrOAc (3×1 L). The DCM layer was concentrated under vacuum (250 TO 220 torr) at 25° C. to give yellow oil (330 g). The i-PrOAc extracts were concentrated under vacuum at 35° C. to give 31.7 g of white solid. The 330 g of yellow oil and the 31.7 g of white solid were combined and dissolved TBME (2.0 L) and acidified with 2N HCl (600 mL) while maintaining the temperature between 17 and 23° C. to give pH=1. The TBME layer containing anisole and its derivatives was separated. The aqueous layer was adjusted to pH to 9-10 by adding aqueous saturated K$_2$CO$_3$ (500 mL) and stirring for 30 minutes. A white milky solution formed during the addition. i-PrOAc (2.5 L) was added to the aqueous layer and stirred for 30 minutes. The organic layer was separated and washed with brine (300 mL). The organic layer was concentrated to dryness to give a yellow oil, and the aqueous layer was re-extracted with i-PrOAc (2×1 L) and the i-PrOAc layer was concentrated to dryness to give a cloudy liquid that solidified on standing. The i-PrOAc extracts yielded 3-fluoro-5-((2R,4S)-4-fluoropyrrolidin-2-yl)benzonitrile (I-15). Melting point: 45-50° C. $^1$H NMR (400 MHz, CDCl$_3$) δ 7.48 (s, 1 H), 7.43-7.37 (m, 1 H), 7.24-7.20 (m, 1 H), 5.28 (dt, J=3.6, 53.6 Hz, 1 H), 4.57 (dd, J=6.4, 9.6 Hz, 1 H), 3.44-3.18 (m, 2 H), 2.63-2.50 (m, 1 H), 1.78-1.61 (m, 1 H).

Synthesis of (R)-3-(4,4-difluoropyrrolidin-2-yl)-5-fluorobenzonitrile (I-24)

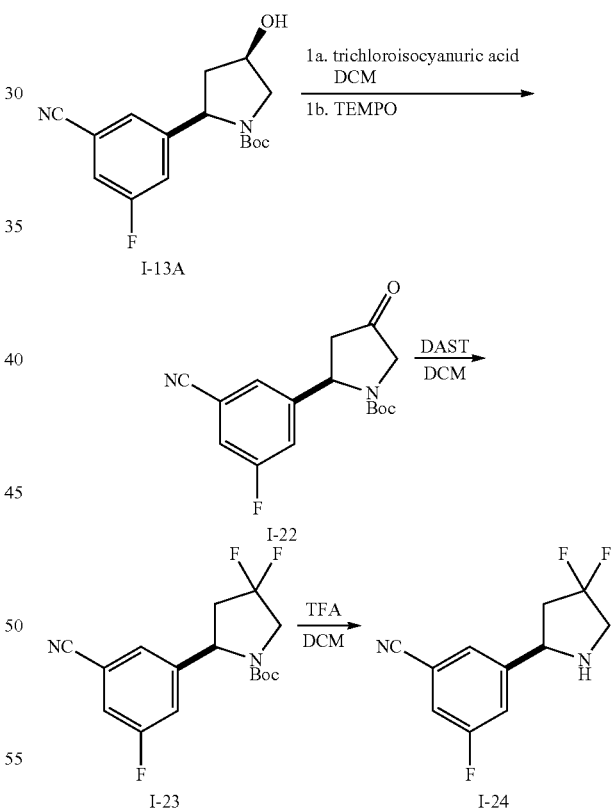

To a solution of (2R,4R)-tert-butyl 2-(3-cyano-5-fluorophenyl)-4-hydroxypyrrolidine-1-carboxylate (I-13A) (0.52 g, 1.7 mmol) and trichloroisocyanuric acid (0.4 g, 1.7 mmol) in DCM (20 mL) at −10° C. was added 2,2,6,6-tetramethylpiperidine-1-oxyl (TEMPO) (27 mg, 0.17 mmol). The mixture was stirred at −10° C. for 15 minutes, then to room temperature over 1 hour and subsequently poured into cold aqueous NaHCO$_3$ containing ice while stirring. The organic layer was separated, washed with brine, dried over sodium sulfate, filtered and reduced to dryness to yield (R)-tert-butyl 2-(3-cyano-5-fluorophenyl)-4-oxopyrrolidine-1-carboxylate (I-16). $^1$H NMR (400 MHz, CDCl$_3$) δ 7.27-7.22 (m, 2 H), 7.12 (td, J=2.0, 8.8 Hz, 1 H), 5.33 (bs, 1 H), 4.06 (d, J=19.6 Hz, 1 H), 3.86 (d, J=19.6 Hz, 1 H), 3.15 (dd, J=10.0, 18.8 Hz, 1 H), 2.47 (dd, J=3.2, 18.8 Hz, 1 H), 1.35 (bs, 9 H). MS m/z 249.1 (M–56)$^+$.

To a solution of (R)-tert-butyl 2-(3-cyano-5-fluorophenyl)-4-oxopyrrolidine-1-carboxylate (I-22) (0.54 g, 1.8 mmol) in DCM (15 mL) in a plastic bottle at −78° C. was added DAST (1.9 mL, 14.4 mmol). The resulting orange homogeneous solution was stirred at −78° C. for 30 minutes then room temperature for 12 hours. The reaction was diluted with DCM and washed with water, brine, dried over sodium sulfate, filtered and reduced to dryness. The crude product was purified by flash column chromatography on silica with hexanes/EtOAc gradient as eluant to yield (R)-tert-butyl 2-(3-cyano-5-fluorophenyl)-4,4-difluoropyrrolidine-1-carboxylate (I-23) as a clear oil that crystallizes on standing. $^1$H NMR (400 MHz, CDCl$_3$) δ 7.33 (s, 1 H), 7.30-7.26 (m, 1 H), 7.23-7.17 (m, 1 H), 5.15-4.90 (m, 1 H), 4.02-3.84 (m, 2 H), 2.94-2.78 (m, 1 H), 2.36-2.22 (m, 1 H), 1.15-1.10 (m, 9 H). MS m/z 249.1 (M–56)$^+$.

To a solution of (R)-tert-butyl 2-(3-cyano-5-fluorophenyl)-4,4-difluoropyrrolidine-1-carboxylate (I-23) (0.45 g, 1.4 mmol) in DCM (3 mL) was added TFA (3 mL) and stirred at room temperature for 1 hour. All the solvents were removed under reduced pressure. The crude was diluted with EtOAc, washed with aqueous NaHCO$_3$ and brine, dried over sodium sulfate, filtered and concentrated to yield (R)-3-(4,4-difluoropyrrolidin-2-yl)-5-fluorobenzonitrile (I-24) as a light yellow oil. $^1$H NMR (400 MHz, CDCl$_3$) δ 7.52 (s, 1 H), 7.42 (d, J=9.2 Hz, 1 H), 7.29-7.26 (m, 1 H), 4.46 (t, J=8.8 Hz, 1 H), 3.52-3.30 (m, 2 H), 2.74-2.60 (m, 1 H), 2.20-2.04 (m, 1 H), 1.90 (bs, 1 H). MS m/z 227.1 (M+1)$^+$.

Synthesis of 5-bromo-N,N-bis(4-methoxybenzyl)pyrazolo[1,5-a]pyridine-3-carboxamide added 6 N KOH (0.3 uL, 2.0 mmol). The reaction was heated to reflux for 3 hours then cooled to room temperature and neutralized to pH 6 with 1M HCl. The resulting solid was filtered and dried under vacuum to yield 5-bromopyrazolo[1,5-a]pyridine-3-carboxylic acid (I-25) as a white solid. $^1$H NMR (400 MHz, DMSO-d$_6$) δ 8.83 (d, J=7.6 Hz, 1 H), 8.42 (s, 1 H), 8.21 (d, J=2.4 Hz, 1 H), 7.30 (dd, J=2.0, 7.6 Hz, 1 H). MS m/z 240.9, 242.9 (M+1)$^+$.

To a solution of 5-bromopyrazolo[1,5-a]pyridine-3-carboxylic acid (I-25) (66 mg, 0.27 mmol) in DMF (3 mL) was added DIEA (0.14 mL) and HATU (0.10 g, 0.27 mmol). The reaction was stirred for 30 minutes at room temperature then bis(4-methoxybenzyl)amine (70 mg, 0.27 mmol) was added. Stirring was continued at room temperature for 12 hours. The reaction was diluted with EtOAc, washed with brine, dried over magnesium sulfate, filtered and reduced to dryness. The crude product was purified by flash column chromatography on silica with hexanes/EtOAc gradient as eluant to yield 5-bromo-N,N-bis(4-methoxybenzyl)pyrazolo[1,5-a]pyridine-3-carboxamide (I-26). $^1$H NMR (400 MHz, CDCl$_3$) δ 8.50 (d, J=2.4 Hz, 1 H), 8.26 (dd, J=0.4, 7.2 Hz, 1 H), 7.88 (s, 1 H), 7.22 (d, J=8.0 Hz, 4 H), 7.00 (dd, J=2.0, 7.2 Hz, 1 H), 6.91 (d, J=8.4 Hz, 4 H), 4.67 (s, 4 H), 3.82 (s, 6 H). MS m/z 480.1, 482.1 (M+1)$^+$.

Synthesis of 2-(2-(trifluoromethyl)phenyl)pyrrolidine (I-28)

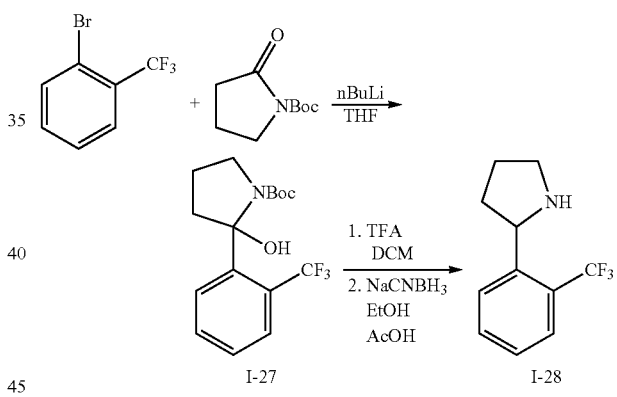

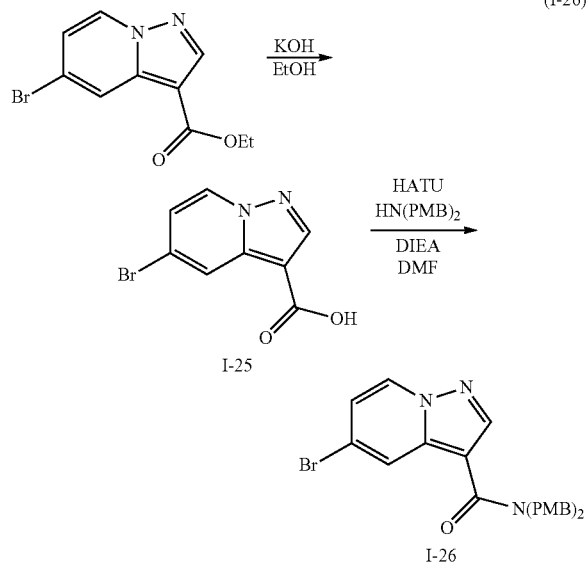

To a solution of 1-bromo-2-(trifluoromethyl)benzene (0.27 mL, 2.0 mmol) in THF (5 mL) at −78° C. was added nBuLi (0.72 mL of a 2.8 M solution in Hexane, 2.0 mmol). The reaction was stirred at −78° C. for 15 minutes then added to a solution of tert-butyl 2-oxopyrrolidine-1-carboxylate (0.33 mL, 2.0 mmol) in THF (5 mL) at −78° C. The reaction was stirred to room temperature over 1 hour, quenched with saturated aqueous ammonium chloride and diluted with EtOAc. The organic layer was separated, dried over magnesium sulfate, filtered and reduced to dryness to afford tert-butyl 2-hydroxy-2-(2-(trifluoromethyl)phenyl)pyrrolidine-1-carboxylate (I-27) as a clear oil. MS m/z 276.1 (M−55)$^+$.

To a solution of tert-butyl 2-hydroxy-2-(2-(trifluoromethyl)phenyl)pyrrolidine-1-carboxylate (I-27) (0.44 g, 1.6 mmol) in DCM (20 mL) was added TFA (10 mL). The reaction was stirred at room temperature until complete by LCMS then reduced to dryness. The crude mixture was dissolved in EtOH:AcOH (10:1, 8 mL) and was added NaCNBH$_3$ (0.17 g, 2.7 mmol). The reaction was stirred for 1 hour then partitioned with EtOAc and saturated aqueous NaHCO$_3$. The organic layer was separated, dried over MgSO$_4$, filtered and To a suspensions of ethyl 5-bromopyrazolo[1,5-a]pyridine-3-carboxylate (0.27 g, 1.0 mmol) in EtOH (5 mL) was reduced to dryness to afford 2-(2-(trifluoromethyl)phenyl)pyrrolidine (I-28) as a clear oil. MS m/z 216.1 (M+1)⁺.

Synthesis of (3S,5R)-5-(3-fluorophenyl)pyrrolidine-3-carbonitrile 2,2,2-trifluoroacetate (I-31)

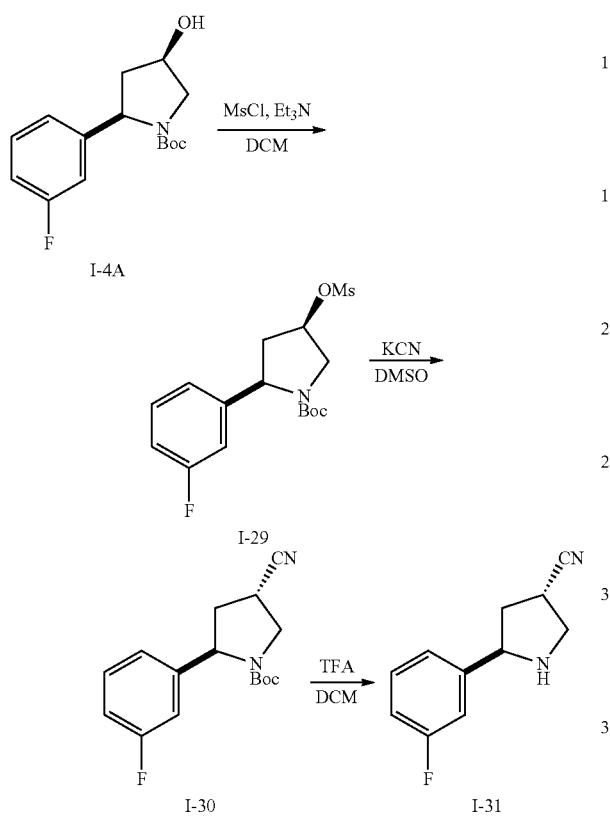

To a solution of (2R,4R)-tert-butyl 2-(3-fluorophenyl)-4-hydroxypyrrolidine-1-carboxylate (I-4A) (253 mg, 0.9 mmol) in DCM (6 mL) at 0° C. was added triethylamine (0.25 mL, 1.8 mmol) followed by dropwise addition of methanesulfonyl chloride (95 µL, 1.3 mmol). After stirring 2 hours at room temperature the reaction mixture was concentrated under reduced pressure and the resulting solid was extracted with Et₂O (2×20 mL). The combined extracts were washed sequentially with 1% aqueous citric acid and brine, dried over MgSO₄, filtered and concentrated under reduced pressure to afford (2R,4R)-tert-butyl 2-(3-fluorophenyl)-4-((methylsulfonyl)oxy)pyrrolidine-1-carboxylate (I-29) as a colorless oil. MS m/z 382.1 (M+23)⁺.

A mixture of (2R,4R)-tert-butyl 2-(3-fluorophenyl)-4-((methylsulfonyl)oxy)pyrrolidine-1-carboxylate (I-29) (165 mg, 0.46 mmol), potassium cyanide (36 mg, 0.55 mmol) and DMSO (2 mL) was heated at 90° C. for 3 hours. After cooling, the reaction mixture was partitioned in Et₂O and water. The organic layer was washed with brine, dried over MgSO₄, filtered and concentrated to dryness. The residue was purified by silica gel chromatography, eluted with EtOAc/Hex (0-50% gradient) to yield (2R,4S)-tert-butyl 4-cyano-2-(3-fluorophenyl)-pyrrolidine-1-carboxylate (I-30) as a colorless oil. ¹H NMR (400 MHz, CDCl₃) δ 7.35-7.30 (m, 1 H), 7.02-6.93 (m, 2 H), 6.87 (d, J=9.6 Hz, 1 H), 5.16ᵣ₁ (bs, 0.4 H), 5.00ᵣ₂ (bs, 0.6 H), 4.00-3.73 (m, 2 H), 3.16 (bs, 1 H), 2.67 (bs, 1 H), 2.25-2.21 (m, 1 H), 1.49 (bs, 3 H), 1.23 (bs, 6 H). MS m/z 313.1 (M+23)⁺.

To a solution of (2R,4S)-tert-butyl 4-cyano-2-(3-fluorophenyl)-pyrrolidine-1-carboxylate (I-30) (72 mg, 0.25 mmol) in DCM (0.5 mL) was added TFA (0.5 mL) with stirring. After 1 hour the volatile organics were removed under reduced pressure. The residue was triturated with Et₂O and the resulting solids collected and dried under vacuum to give (3S,5R)-5-(3-fluorophenyl)pyrrolidine-3-carbonitrile 2,2,2-trifluoroacetate (I-31), which was used without purification. MS m/z 191.1 (M+1)⁺.

Synthesis of 5-((2R,4S)-4-cyano-2-(3-fluorophenyl)pyrrolidin-1-yl)-N,N-bis(4-methoxybenzyl)pyrazolo[1,5-a]pyridine-3-carboxamide (I-35)

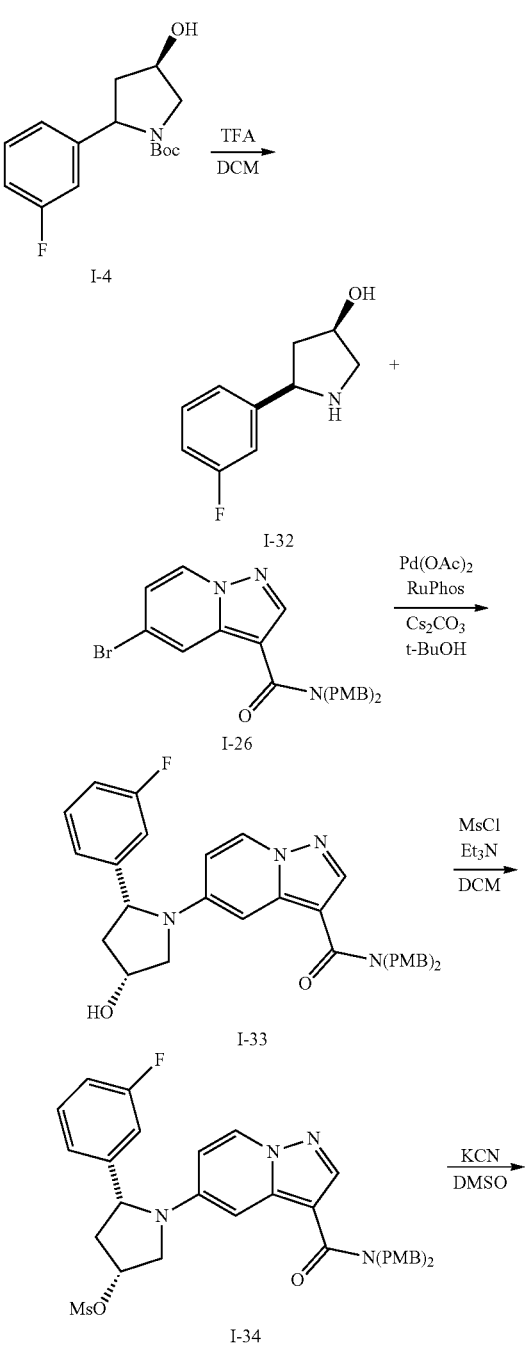

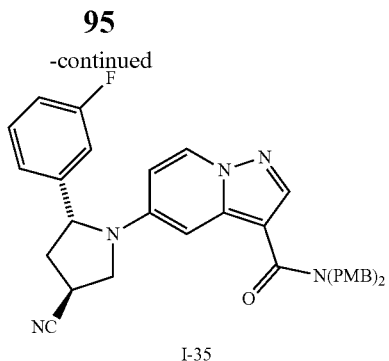

I-35

To a solution of (2R,4R)-tert-butyl 2-(3-fluorophenyl)-4-hydroxypyrrolidine-1-carboxylate (I-4) (890 mg, 3.14 mmol) in DCM (5 mL) at room temperature was added TFA (5 mL). The mixture was stirred at room temperature for 2 hours then concentrated to dryness. The crude was diluted with EtOAc, washed with aqueous NaHCO$_3$ and brine, dried over sodium sulfate, filtered and concentrated to yield (3R,5R)-5-(3-fluorophenyl)pyrrolidin-3-ol (I-32), which was used without purification.

A N$_2$ purged flask was charged with 5-bromo-N,N-bis(4-methoxybenzyl)pyrazolo[1,5-a]pyridine-3-carboxamide (I-26) (0.19 g, 0.39 mmol), palladium acetate (3 mg, 12 μmol), RuPhos (11 mg, 24 μmol), cesium carbonate (0.25 g, 0.78 mmol), tBuOH (1 mL) and (3R,5R)-5-(3-fluorophenyl)pyrrolidin-3-ol (I-32) (71 mg, 0.39 mmol). The contents were heated to 120° C. overnight in an oil bath. Upon cooling to room temperature the reaction was filtered through celite and concentrated. The crude product was purified by column chromatography on silica gel with EtOAc/hexanes gradient as eluant to yield 5-((2R,4R)-2-(3-fluorophenyl)-4-hydroxy-pyrrolidin-1-yl)-N,N-bis(4-methoxybenzyl)pyrazolo[1,5-a]pyridine-3-carboxamide (I-33). $^1$H NMR (400 MHz, CDCl$_3$) δ 7.96-7.84 (m, 1 H), 7.65-7.49 (m, 1 H), 7.09-7.04 (m, 3 H), 7.01-6.95 (m, 3 H), 6.92-6.81 (m, 3 H), 6.72-6.64 (m, 4 H), 6.05-5.92 (m, 1 H), 4.79-4.69 (m, 1 H), 4.56-4.41 (m, 3 H), 4.38-4.26 (m, 2 H), 3.96-3.86 (m, 1 H), 3.66-3.59 (m, 6 H), 2.63-2.49 (m, 1 H), 2.06-1.94 (m, 1 H), 1.87-1.79 (m, 1 H). MS m/z 581.2 (M+1)+

To a solution 5-((2R,4R)-2-(3-fluorophenyl)-4-hydroxy-pyrrolidin-1-yl)-N,N-bis(4-methoxybenzyl)pyrazolo[1,5-a]pyridine-3-carboxamide (I-33) (150 mg, 0.26 mmol) in DCM (anhyd, 2 mL) at 0° C. was added triethylamine (0.070 mL, 0.5 mmol) followed by dropwise addition of methanesulfonyl chloride (28 μL, 0.36 mmol). After stirring 2 hours at room temperature the reaction mixture was concentrated under reduced pressure. The resulting solid was taken up in EtOAc and washed twice with brine, dried over Na$_2$SO$_4$, filtered and concentrated under reduced pressure to afford (3R,5R)-1-(3-(bis(4-methoxybenzyl)carbamoyl)pyrazolo[1,5-a]pyridin-5-yl)-5-(3-fluorophenyl)pyrrolidin-3-yl methanesulfonate (I-34), which was used without further purification. MS m/z 659.2 (M+1)+.

A mixture of (3R,5R)-1-(3-(bis(4-methoxybenzyl)carbamoyl)pyrazolo[1,5-a]pyridin-5-yl)-5-(3-fluorophenyl)pyrrolidin-3-yl methanesulfonate (I-34) (0.17 g, 0.26 mmol), potassium cyanide (20 mg, 0.31 mmol) and DMSO (anhyd, 1 mL) was heated at 90° C. for 3 hours. After cooling, the reaction mixture was partitioned in EtOAc and water. The organic layer was washed with brine, dried over Na$_2$SO$_4$, filtered and concentrated to dryness. The residue was purified by silica chromatography eluting with an EtOAc/Hex gradient to yield 5-((2R,4S)-4-cyano-2-(3-fluorophenyl)pyrrolidin-1-yl)-N,N-bis(4-methoxybenzyl)pyrazolo[1,5-a]pyridine-3-carboxamide (I-35). $^1$H NMR (400 MHz, CDCl$_3$) δ 8.15-8.11 (m, 1 H), 7.80 (s, 1 H), 7.37-7.28 (m, 1 H), 7.22-7.15 (m, 5 H), 7.02-6.93 (m, 2 H), 6.93-6.86 (m, 5 H), 6.15 (dd, J=2.7, 7.7 Hz, 1H), 5.08 (dd, J=2.6, 7.9 Hz, 1 H), 4.72 (d, J=15.7 Hz, 2 H), 4.54 (d, J=15.8 Hz, 2 H), 4.20-4.14 (m, 1 H), 3.91-3.83 (m, 1 H), 3.82 (s, 6 H), 3.37-3.24 (m, 1 H), 2.82 (ddd, J=8.1, 10.1, 12.4 Hz, 1 H), 2.41 (ddd, J=2.8, 6.4, 12.4 Hz, 1 H). MS m/z 590.2 (M+1)+

Synthesis of 5-iodo-N,N-bis(4-methoxybenzyl)pyrazolo[1,5-a]pyridine-3-carboxamide (I-43)

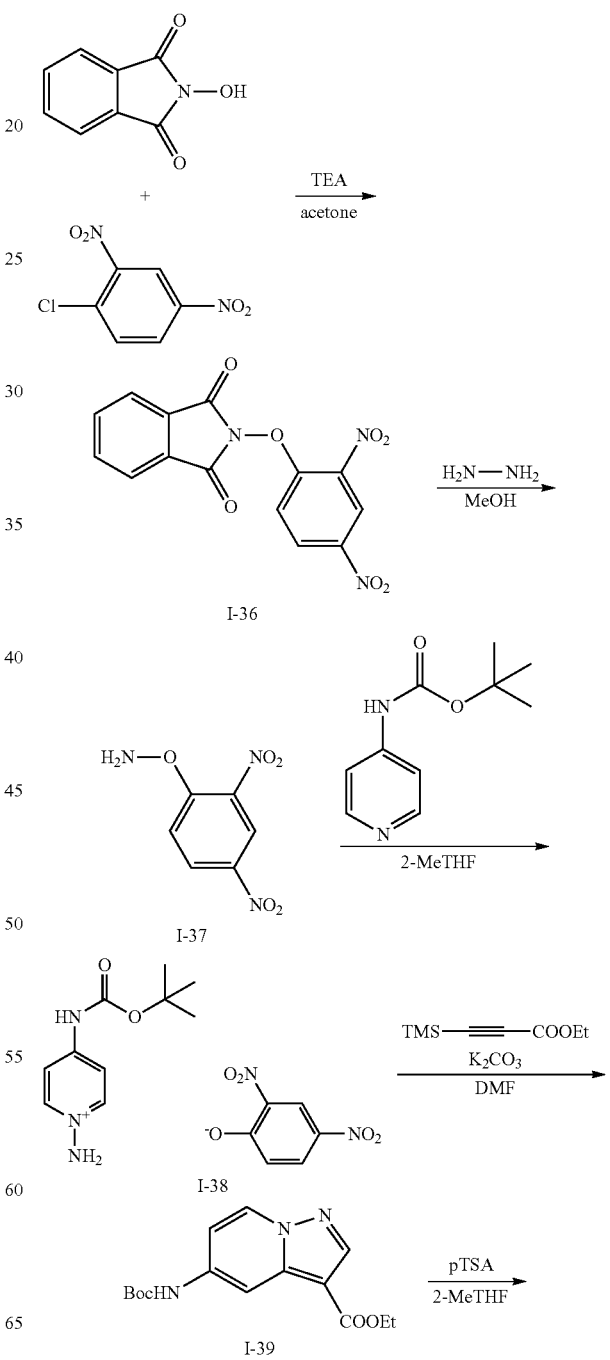

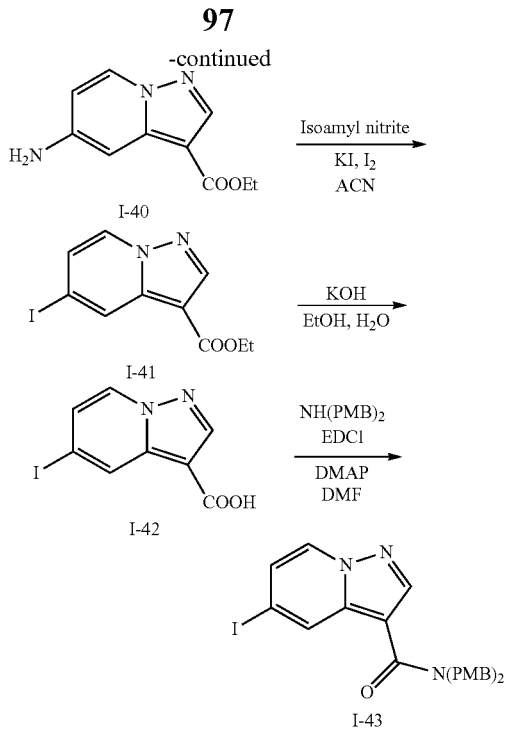

A 1 L four-necked flask equipped with an overhead stirrer, thermocouple and a condenser was charged with 2-hydroxyisoindoline-1,3-dione (25 g, 153 mmol) and acetone (500 mL). To this stirred suspension was added triethylamine (15.7 g, 154 mmol). The reaction mixture turned dark red and 2-hydroxyisoindoline-1,3-dione slowly dissolved and became a homogeneous solution after 10 minutes. 1-Chloro-2,4-dinitrobenzene (31 g, 153 mmol) was added and the reaction was stirred at room temperature for 2 hours. After this time, a bright yellow suspension formed, and the reaction mixture was poured into 500 mL of ice-water. The precipitate was filtered and washed three times with cold MeOH (100 mL). The solid was compressed and washed with heptanes (3×100 mL) and dried under vacuum to give 2-(2,4-dinitrophenoxy)isoindoline-1,3-dione (I-33). $^1$H NMR (400 MHz, CDCl$_3$) δ 8.99 (d, 1 H), 8.44 (dd, 1 H), 8.03-7.97 (m, 2 H), 7.95-7.90 (m, 2 H), 7.46 (d, 1 H).

A 5 L four-necked flask equipped with an overhead stirrer, thermocouple and a condenser was charged with 2-(2,4-dinitrophenoxy)isoindoline-1,3-dione (I-36) (96 g, 291.6 mmol) and DCM (2 L). The stirred solution was cooled to 0° C. and a solution of hydrazine hydrate (36.46 g, 729 mol) in MeOH (300 mL) was added at 0° C. The reaction mixture rapidly became bright yellow and a precipitate formed. The suspension was stirred at 0° C. for 2 hours. 0.5 N HCl (2 L) was added at 0° C. and stirred for 30 minutes. The mixture was filtered and washed with DCM (2×200 mL). The organic layer was separated, dried over MgSO$_4$, filtered and the solvent removed to give O-(2,4-dinitrophenyl)hydroxylamine (I-37) as a red-orange solid. $^1$H NMR (400 MHz, CDCl$_3$) δ 8.82 (d, 1 H), 8.44 (dd, 1 H), 8.07 (d, 1 H), 6.42 (sbr, 2 H).

To a 3 L four-necked flask equipped with an overhead stirrer, thermocouple and a condenser was charged with O-(2,4-dinitrophenyl)hydroxylamine (I-37) (248 g, 1245.5 mmol) and 2-MeTHF (1 L). To the stirred suspension at room temperature were added tert-butyl pyridin-4-ylcarbamate (254.6 g, 1245.5 mmol) and 2-MeTHF (1 L). The mixture was stirred at room temperature for 10 minutes and slowly heated to 40° C. (after 30 minutes the suspension became a solution at 30° C.). An exotherm was observed at 40° C. and the temperature reached 45° C. without heating. The mixture was cooled with a water bath to 40° C. and stirred at 40° C. for 4 hours. The mixture was further cooled to room temperature and stirred for 15 hours. The batch was filtered and the solid was washed with MTBE (2×200 mL) and air dried to give 1-amino-4-(tert-butoxycarbonylamino)pyridinium 2,4-dinitrophenolate (I-38) as a yellow solid. $^1$H NMR (500 MHz, DMSO) δ 10.90 (s, 1 H), 8.62 (s, 1 H), 8.54 (d, 2 H), 7.91 (d, 2 H), 7.85 (m, 3 H), 6.30 (d, 1 H), 1.46 (s, 9 H).

A 22 L flask was charged with 1-amino-4-(tert-butoxycarbonylamino)pyridinium 2,4-dinitrophenolate (I-38) (800 g, 2033.8 mmol), K$_2$CO$_3$ (421.6 g, 3050.7 mmol) and DMF (4 L). The mixture was cooled to 15-18° C. Ethyl 3-(trimethylsilyl)propiolate (400 g, 2338.9 mmol) was added dropwise over 10 minutes. The mixture was allowed to warm to 20-25° C. over 1 hour and the mixture turned dark in color. The mixture was stirred at room temperature for over 3 hours and cooled with an ice-water bath. EtOAc (400 mL) and water (8000 mL) were added while maintaining a batch temperature <25° C. The layers were separated and the aqueous layer was extracted with EtOAc (4 L). The combined organic layers were washed with water (2×2 L) and brine (2 L). The organic layer was concentrated under vacuum to give a dark solid residue (700 g). The solid residue was dissolved in DCM (3 L) with gentle heating. The solution was purified via Biotage using 8×800 g silica cartridges with EtOAc/Heptane as the eluent. Fractions 10 to 15 (300 mL/fraction) were collected and concentrated under vacuum to a volume ~400 mL and heptane (200 mL) was added. The resulting slurry was filtered and the solid was rinsed with heptane (2×300 mL). The solid was air dried to give ethyl 5-((tert-butoxycarbonyl)amino)pyrazolo[1,5-a]pyridine-3-carboxylate (I-38) as an off-white solid. $^1$H NMR (500 MHz, CDCl$_3$) δ 8.39 (d, 1 H), 8.32 (s, 1 H), 7.95 (d, 2 H), 7.27 (m, 1 H), 6.79 (s, 1 H), 4.31 (m, 2 H), 1.50 (s, 9 H), 1.35 (t, 3 H).

A solution of 4-methylbenzenesulfonic acid hydrate (1046 g, 5.50 mol) in 2-methylTHF (2.4 L) was concentrated under vacuum to a volume of ~2 L to azeotropically remove water. The residue was diluted with fresh 2-methyl THF and distilled to further remove water until Karl-Fisher titration showed the solution contained 4.3% water (the final volume should be ~2000 mL). A 22 L ROUND BOTTOM FLASK was charged with ethyl 5-(tert-butoxycarbonylamino)pyrazolo[1,5-a]pyridine-3-carboxylate (I-39) (424 g, 1.39 mol) and the 4-methylbenzenesulfonic acid solution in 2-methylTHF (2000 mL). The mixture was heated to 32° C. to form a suspension and heated to 56° C. to give a solution. The mixture was heated to 71° C. and CO$_2$ started to evolve. The heating was stopped for 20 minutes to slow down the reaction and a suspension was obtained. The mixture was stirred at 73° C. over 2 hours. A sample was taken for analysis and HPLC showed the reaction was complete. The mixture was cooled to 0-5° C. and a solution of KHCO$_3$ (1000 g) in water (6 L) was added slowly (aqueous layer pH~9). (Note: a large amount of gas evolved). The aqueous layer was separated and K$_2$CO$_3$ (100 g) was added to adjust the pH to 10. (Note: the aqueous layer turned dark blue.) The aqueous layer was extracted with 2-methylTHF (2×2 L). The combined organics were washed with 15% NaCl solution (4000 mL), dried over Na$_2$SO$_4$, filtered and concentrated to a volume of 800 mL. To the resulting slurry was added heptane (600 mL). The slurry was filtered and the solid was rinsed with heptane (300 mL). The solid was dried under vacuum at room temperature over 6 hours to give ethyl 5-aminopyrazolo[1,5-a]pyridine-3-carboxylate (I-40) as a grey solid. $^1$H NMR (500 MHz, DMSO-d6) δ 8.39 (d, 1 H), 8.07 (s, 1 H), 6.93 (d, 1 H), 6.49 (dd, 1 H), 6.30 (b, 2 H), 4.21 (q, 2 H), 1.29 (t, 3 H).

A 2 L round bottom flask was charged with ethyl 5-aminopyrazolo[1,5-a]pyridine-3-carboxylate (I-40) (28.8 g, 140 mmol) and CH$_3$CN (450 mL). The suspension was cooled to 10° C. and BF$_3$.Et$_2$O (26.3 mL, 29.7 g, 209 mmol) was added in one portion. The resulting light slurry was cooled to −15° C. and isopentyl nitrite (28 mL, 24.5 g, 209 mmol) was added at −15 to −10° C. over 5 minutes. The mixture was then warmed to 0° C. and stirred at 0-5° C. over 2 hours and a dark suspension was obtained. Iodine (2.7 g, 11 mmol) and KI (35.1 g, 166 mmol) were added at 0 to 5° C. in portions over 2 minutes. A dark mixture was obtained with gas evolution. The mixture was warmed to 20° C. and stirred at 20° C. over 4 hours. A sample was taken for analysis and HPLC showed consumption of the diazonium intermediate. A solution of sodium thiosulfate pentahydrate (75 g, 302 mmol) in water (450 mL) was added and the mixture was stirred at 20° C. over 5 hours. The mixture was cooled to 0-5° C. and stirred at 0-5° C. over 30 minutes. The slurry was filtered and the solid cake was rinsed with CH$_3$CN/H$_2$O (1:1, 400 mL) and water (400 mL). The solid was air dried over 72 hours to give ethyl 5-iodopyrazolo[1,5-a]pyridine-3-carboxylate (I-41) as a red solid. $^1$H NMR (500 MHz, DMSO-d6) δ 8.64 (d, 1 H), 8.41 (d, 1 H), 8.40 (s, 1 H), 7.39 (dd, 1 H), 4.31 (q, 2 H), 1.34 (t, 3 H).

A 22 L round bottom flask was charged with ethyl 5-iodopyrazolo[1,5-a]pyridine-3-carboxylate (I-41) (376 g, 1.19 mol), KOH (133.5 g), EtOH (3856 mL) and water (290 mL). The mixture was heated to 55° C. and stirred at 55° C. for 3 hours. A sample was taken for analysis and HPLC showed no (I-41) remaining. Water (2.5 L) was added to obtain a dark solution with some insoluble solids which were removed by filtration. To the filtrate was added acetic acid (150 g, 2.5 mol) until pH~6 followed by water (4 L). The mixture was stirred at 15 to 20° C. over 30 minutes to form a slurry that was filtered and rinsed with EtOH/H$_2$O (1:2 v/v) to yield 5-iodopyrazolo[1,5-a]pyridine-3-carboxylic acid (I-42) as a red solid. $^1$H NMR (500 MHz, DMSO-d$_6$) δ 12.62 (b, 1 H), 8.65 (d, 1 H), 8.44 (d, 1 H), 8.37 (s, 1 H), 7.37 (dd, 1 H).

A 22 L round bottom flask was charged with 5-iodopyrazolo[1,5-a]pyridine-3-carboxylic acid (I-42) (200 g, 694.3 mmol), bis(4-methoxybenzyl)amine (182.2 g, 708.3 mmol), DMAP (42.4 g, 347.2 mmol), EDCI (146.4 g, 763.8 mmol) and DMF (3500 mL). The suspension was stirred at room temperature over 16 hours and a dark solution was obtained. HPLC showed no (I-42) remaining. 2-MethylTHF (4 L) and water (7 L) were added to the reaction mixture while keeping the batch temperature <25° C. The aqueous layer was separated and extracted with 2-methylTHF (4 L). The combined 2-methylTHF layers were washed with 0.25 N HCl (2×4 L), aqueous saturated NaHCO$_3$ (4 L) and 10% brine (4 L). The 2-methylTHF layer was treated with carbon (20 g) and Na$_2$SO$_4$ (80 g). The solution was passed through a silica gel pad (400 g of silica gel 240-400 mesh) and the pad was washed with 2-MeTHF (3 L). The filtrate was concentrated under vacuum to give 5-iodo-N,N-bis(4-methoxybenzyl) pyrazolo[1,5-a]pyridine-3-carboxamide (I-43) as a solid. $^1$H NMR (500 MHz, CDCl$_3$) δ 8.73 (d, 1 H), 8.17 (d, 1H), 7.86 (s, 1H), 7.22 (d, 4 H), 7.14 (dd, 1 H), 6.92 (d, 4 H), 4.68 (s, 4 H), 3.83 (s, 6 H).

Synthesis of Synthesis of (R)-2-(4,4-difluoropyrrolidin-2-yl)-4-fluoro-N-isopropylbenzamide (I-51)

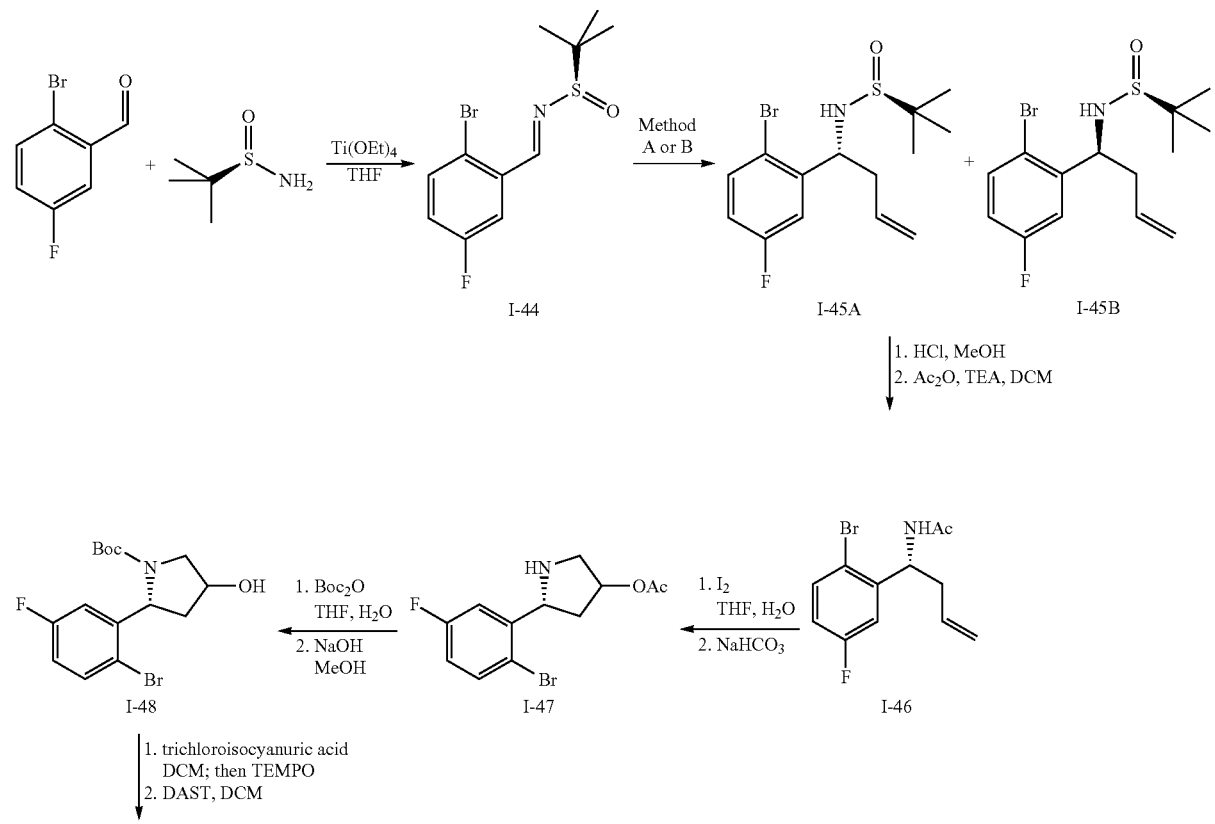

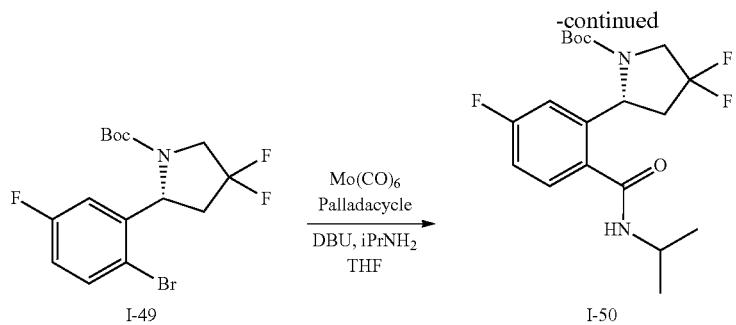 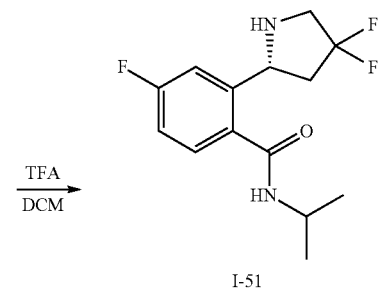

To a solution of 2-bromo-5-fluorobenzaldehyde (2.44 g, 12.0 mmol) and (S)-(−)-2-methyl-2-propane-sulfinamide (1.45 g, 12.0 mmol) in THF (30 mL, anhyd.) was added titanium tetraethoxide (2.8 mL, 13.2 mmol, tech) at room temperature. After stirring 16 hours the reaction mixture was charged with brine (25 mL) and EtOAc (40 mL). After stirring 10 minutes the mixture was filtered through a pad of Celite™. Combined filtrates were washed with water and brine, dried over sodium sulfate and concentrated. The residue was purified by silica chromatography with EtOAc/Hex (0-25%) as eluent to give (S,E)-N-(2-bromo-5-fluorobenzylidene)-2-methylpropane-2-sulfinamide (I-44) as a white solid. $^1$H NMR (400 MHz, CDCl$_3$) δ 8.94 (d, J=2.2 Hz, 1 H), 7.77 (dd, J=3.1, 9.1 Hz, 1 H), 7.64 (dd, J=5.0, 8.8 Hz, 1 H), 7.12 (ddd, J=3.1, 7.5, 8.8 Hz, 1 H), 1.30 (s, 9 H).

Method A

To a solution of (S,E)-N-(2-bromo-5-fluorobenzylidene)-2-methylpropane-2-sulfinamide (I-44) (612 mg, 2.0 mmol) in DCM (6 mL) at −78° C. was added dropwise a solution of allylmagnesium chloride (2.0M in THF, 1.5 mL, 3.0 mmol). After stirring 5 hours at −78° C., the reaction mixture was quenched by addition of saturated aqueous NH$_4$Cl (1 mL) and then allowed to warm to room temperature. The mixture was extracted with EtOAc (2×25 mL) and the combined extracts were washed with brine, dried over sodium sulfate and concentrated. The residue was purified by silica chromatography with EtOAc/Hex (25-50%) as eluent to afford a mixture of (S)-N-((R)-1-(2-bromo-5-fluorophenyl)but-3-en-1-yl)-2-methylpropane-2-sulfinamide (I-45A) and (S)-N-((S)-1-(2-bromo-5-fluorophenyl)but-3-en-1-yl)-2-methylpropane-2-sulfinamide (I-45B) as a clear waxy solid. The latter has been assigned tentatively as the major product of the mixture after analysis of NMR and chiral HPLC data. $^{19}$F NMR (376 MHz, CDCl$_3$) δ −113.32, −113.87. MS m/z 348.0, 350.0 (M+1)$^+$.

Method B

To a stirred suspension of (S,E)-N-(2-bromo-5-fluorobenzylidene)-2-methylpropane-2-sulfinamide (I-44) (153 mg, 0.50 mmol) and indium powder (230 mg, 2.0 mmol) in saturated NaBr (10 mL, aq) was added allyl bromide (169 µL, 2.0 mmol). After stirring 36 hours the reaction mixture was charged with saturated aqueous NaHCO$_3$ and stirred 30 minutes. The mixture was extracted with EtOAc and combined extracts were washed with brine, dried over sodium sulfate and concentrated. The residue was purified by silica gel chromatography with EtOAc/Hex (5-35%) as eluent to yield the (S)-N-((R)-1-(2-bromo-5-fluorophenyl)but-3-en-1-yl)-2-methylpropane-2-sulfinamide (I-45A) as a clear oil. $^1$H NMR (400 MHz, CDCl$_3$) δ 7.52 (dd, J=5.3, 8.8 Hz, 1 H), 7.14 (dd, J=3.1, 9.8 Hz, 1 H), 6.88 (ddd, J=3.1, 7.7, 8.7 Hz, 1 H), 5.77 (dddd, J=6.1, 8.2, 10.9, 16.6 Hz, 1 H), 5.28-5.16 (m, 2 H), 4.98-4.89 (m, 1 H), 3.74 (s, 1 H), 2.76-2.63 (m, 1 H), 2.39 (dt, J=8.3, 14.2 Hz, 1 H), 1.24 (s, 9 H). $^{19}$F NMR (376 MHz, CDCl$_3$) δ −113.87. MS m/z 348.0, 350.0 (M+1)$^+$.

To a solution of (S)-N-((R)-1-(2-bromo-5-fluorophenyl)but-3-en-1-yl)-2-methylpropane-2-sulfinamide I-45A (1.95 g, 5.6 mmol) in MeOH (15 mL) at 0° C. was added 4N solution of HCl in MeOH (7.5 mL, 30 mmol). After stirring 45 minutes at room temperature, the reaction mixture was chilled to 0° C. and slowly made basic with 15% NaOH. The resulting mixture was concentrated to a minimum volume on a rotary evaporator and then partitioned in EtOAc and saturated aqueous NaHCO$_3$. The combined EtOAc extracts were washed with brine, dried over sodium sulfate and concentrated to yield the corresponding homoallylamine. MS m/z 244.0, 246.0 (M+1)$^+$. The amine was dissolved in DCM (20 mL), chilled to 0° C. and charged with triethylamine (0.98 mL, 7.0 mmol) and then acetic anhydride (0.57 mL, 6.05 mmol). After stirring 2 hours the reaction mixture was washed successively with saturated aqueous NaHCO$_3$, water, 1N HCl and brine, then dried over sodium sulfate and concentrated to dryness to afford (R)-N-(1-(2-bromo-5-fluorophenyl)but-3-en-1-yl)acetamide (I-46) as a white solid. MS m/z 286.0, 288.0 (M+1)$^+$.

To a solution of (R)-N-(1-(2-bromo-5-fluorophenyl)but-3-en-1-yl)acetamide (I-46) (1.50 g, 5.24 mmol) in THF (12 mL) was added water (3 mL) followed by iodine (4.0 g, 15.7 mmol). After stirring 6 hours the reaction mixture was poured into a mixture of saturated aqueous NaHCO$_3$ (30 mL) and saturated aqueous Na$_2$S$_2$O$_3$ (25 mL), extracted with EtOAc (2×40 mL), washed successively with saturated aqueous Na$_2$S$_2$O$_3$, water and brine, dried over sodium sulfate and concentrated to dryness to give (5R)-5-(2-bromo-5-fluorophenyl)pyrrolidin-3-yl acetate (I-47) as a pale amber oil, which was used without purification in the next step. MS m/z 302.0, 304.0 (M+1)$^+$.

To a mixture of (5R)-5-(2-bromo-5-fluorophenyl)pyrrolidin-3-yl acetate (I-47) (1.59 g, 5.24 mmol), dioxane (15 mL) and water (15 mL) was added a solution of di-tert-butyl dicarbonate (1M in THF, 6.6 mL, 6.6 mmol). Added 1N NaOH until pH 9 had been achieved. After 3 hours the reaction mixture was partitioned into EtOAc/water and the combined extracts were washed with brine, dried over sodium sulfate and concentrated to dryness to afford the corresponding carbamate. MS m/z 424.0, 426.0 (M+23)$^+$.

The above carbamate was dissolved in MeOH (15 mL) and chilled to 0° C., and then charged dropwise with 1N NaOH (3.93 mL, 0.75 eq). After stirring 2 hours at room temperature, the reaction had not progressed to completion, as determined by LCMS analysis of an aliquot. Added another portion of 1N NaOH (0.75 eq). After hydrolysis was complete (approx. 1 h), the reaction mixture was partitioned into EtOAc/brine. The combined EtOAc extracts were washed with brine, dried over sodium sulfate, and concentrated. The residue was purified by silica chromatography with EtOAc/Hex (25-50%) as eluent, to yield (2R)-tert-butyl 2-(2-bromo-5-fluorophenyl)-4-hydroxypyrrolidine-1-carboxylate (I-48) as white foam. MS m/z 382.0, 384.0 (M+23)$^+$.

To a solution of (2R)-tert-butyl 2-(2-bromo-5-fluorophenyl)-4-hydroxypyrrolidine-1-carboxylate (I-48) (1.38 g, 3.83 mmol) in DCM (30 mL) at −10° C. was added trichloroisocyanuric acid (0.89 g, 3.8 mmol) followed by 2,2,6,6-tetramethylpiperidino-1-oxy (TEMPO) (60 mg, 0.38 mmol). After stirring 25 minutes at room temperature, the reaction mixture was poured into saturated aqueous NaHCO$_3$ and ice (2 g), and then extracted with DCM. The combined extracts were washed with water (2×) and brine (2×), dried over sodium sulfate and concentrated to dryness to give the corresponding ketone as a pale yellow oil, which was used without purification in the next step. MS m/z 380.0, 382.0 (M+23)$^+$.

The above ketone was dissolved in DCM (8 mL), at −78° C. and then charged with diethylaminosulfur trifluoride (DAST) (1.0 mL, 7.6 mmol). After stirring 12 h at room temperature, the reaction mixture was added to cold water and extracted with DCM. The combined extracts were washed with water and brine, dried over sodium sulfate and concentrated to dryness to afford (R)-tert-butyl 2-(2-bromo-5-fluorophenyl)-4,4-difluoro-pyrrolidine-1-carboxylate (I-49) as a pale yellow, crystalline solid. $^1$H NMR (400 MHz, CDCl$_3$) δ 7.52 (dd, J=5.2, 8.7 Hz, 1 H), 7.06-6.85 (m, 2 H), 5.38-5.26 (m, 1 H), 4.16-4.01 (m, 1 H), 3.96 (q, J=12.4 Hz, 1 H), 3.06-2.88 (m, 1 H), 2.32-2.22 (m, 1 H), 1.49 (bs, 3 H), 1.23 (bs, 6 H). MS m/z 324.0, 326.0 (M−55)$^+$.

To a nitrogen-flushed microwave vial was added (R)-tert-butyl 2-(2-bromo-5-fluorophenyl)-4,4-difluoro-pyrrolidine-1-carboxylate (I-49) (304 mg, 0.80 mmol), molybdenum hexacarbonyl (211 mg, 0.80 mmol), trans-di-µ-acetatobis[2-di-o-tolylphosphino)benzyl]-dipalladium(II) (Palladacycle) (30 mg, 4 mol %), THF (1.6 mL), 1,8-diazabicyclo-[5.4.0]undec-7-ene (DBU) (239 µL, 1.6 mmol) and isopropylamine (171 µL, 2.0 mmol). The vial was capped and then heated at 150° C. for 30 minutes in a Biotage microwave reactor. The cooled reaction mixture was diluted with EtOAc and filtered through Celite. The combined filtrates were washed successively with saturated aqueous NH$_4$Cl, water, 2% citric acid and brine, then dried over sodium sulfate and concentrated. The residue was purified by silica chromatography with EtOAc/Hex (5-30%) as eluent, to yield (R)-tert-butyl 4,4-difluoro-2-(5-fluoro-2-(isopropylcarbamoyl)phenyl)pyrrolidine-1-carboxylate (I-50) as an off-white foam. $^1$H NMR (400 MHz, CDCl$_3$) δ 7.44 (bs, 1 H), 7.11 (bs, 1 H), 7.00 (td, J=2.5, 8.2 Hz, 1 H), 5.31 (t, J=7.7 Hz, 1 H), 4.23 (bs, 1 H), 4.09-3.87 (m, 2 H), 2.91 (bs, 1 H), 2.41 (bs, 1 H), 1.45 (bs, 6 H), 1.26 (d, J=6.5 Hz, 6 H), 1.19 (bs, 3 H). MS m/z 331.1 (M−55)$^+$.

To a solution of (R)-tert-butyl 4,4-difluoro-2-(5-fluoro-2-(isopropylcarbamoyl)phenyl)pyrrolidine-1-carboxylate (I-50) (203 mg, 0.525 mmol) in DCM (0.4 mL) was added TFA (1 mL). After stirring for 2 hours the mixture was concentrated to dryness, diluted with DCM, washed with saturated aqueous NaHCO$_3$ and brine, dried over sodium sulfate and concentrated to dryness to give (R)-2-(4,4-difluoropyrrolidin-2-yl)-4-fluoro-N-isopropylbenzamide (I-51) as a pale brown solid. MS m/z 287.1 (M+H)$^+$. I-51 was also isolated as a racemic mixture using un-resolved 1-45A and 1-45B from Method A in the above sequence.

Synthesis of Exemplary Compounds

Synthesis of ethyl 5-((2R,4S)-4-fluoro-2-(3-fluorophenyl)pyrrolidin-1-yl)pyrazolo[1,5-a]pyridine-3-carboxylate (X-1)

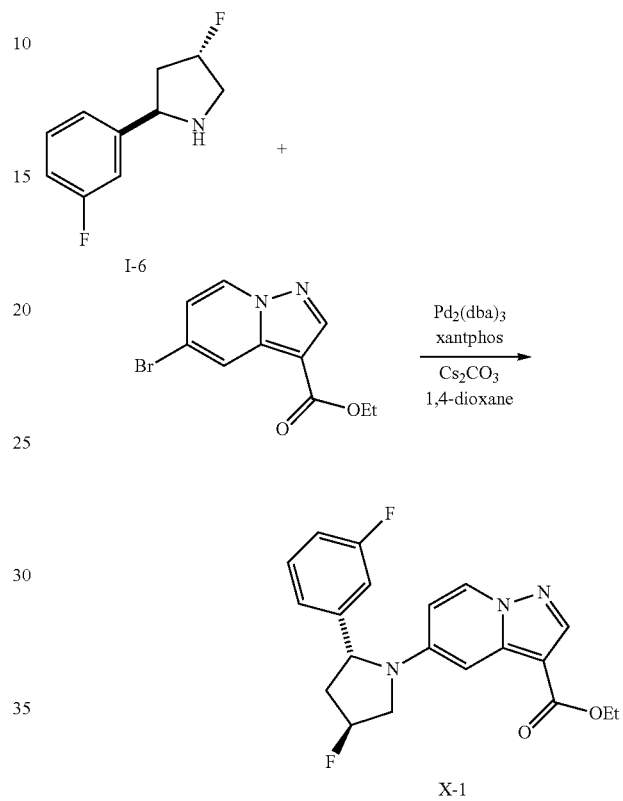

A N$_2$ purged flask was charged with ethyl 5-bromopyrazolo[1,5-a]pyridine-3-carboxylate (27 mg, 0.1 mmol), tris(dibenzylideneacetone)dipalladium(0) (2 mg, 2 µmol), xantphos (5 mg, 8 µmol), cesium carbonate (46 mg, 0.14 mmol), 1,4-dioxane (0.5 mL) and (2R,4S)-4-fluoro-2-(3-fluorophenyl)pyrrolidine (I-6) (18 mg, 0.1 mmol). The contents were heated to 120° C. for 12 hours. Upon cooling to room temperature the reaction was partitioned with EtOAc and water. The organic layer was washed with water, brine, dried over magnesium sulfate, filtered and reduced to dryness. The crude product was purified by column chromatography on silica gel with EtOAc/hexanes gradient as eluant to yield ethyl 5-((2R, 4S)-4-fluoro-2-(3-fluorophenyl)pyrrolidin-1-yl)pyrazolo[1,5-a]pyridine-3-carboxylate (X-1). $^1$H NMR (400 MHz, CDCl$_3$) δ 8.20 (s, 1 H), 8.16 (d, J=7.6 Hz, 1 H), 7.31 (td, J=5.6, 7.6 Hz, 1 H), 7.05 (d, J=7.6 Hz, 1 H), 6.98 (d, J=2.8 Hz, 1 H), 6.96-6.91 (m, 2 H), 6.24 (dd, J=2.8, 8.0 Hz, 1 H), 5.39 (d, J=52.8 Hz, 1 H), 5.04 (dd, J=7.2, 9.2 Hz, 1H), 4.34-4.26 (m, 2 H), 4.17-3.90 (m, 2 H), 2.93-2.81 (m, 1 H), 2.11 (dddd, J=3.6, 9.2, 13.2, 40.8 Hz, 1 H). MS m/z 372.1 (M+1)$^+$.

Synthesis of 5-((2R,4S)-4-fluoro-2-(3-fluorophenyl)pyrrolidin-1-yl)pyrazolo[1,5-a]pyridine-3-carboxylic acid (X-3)

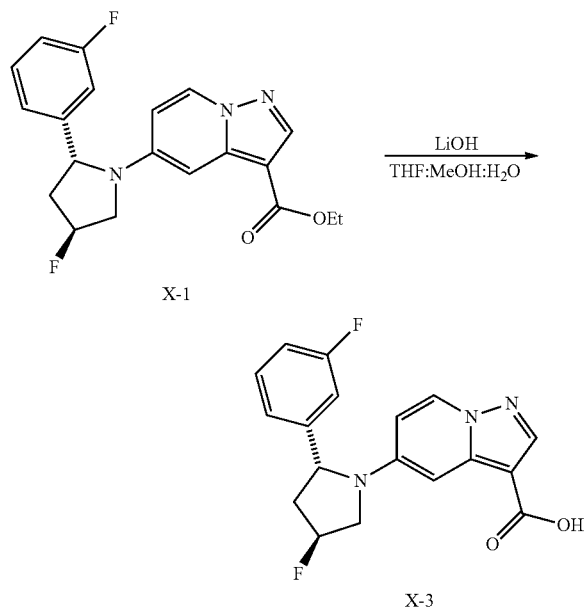

To a suspension of ethyl 5-((2R,4S)-4-fluoro-2-(3-fluorophenyl)pyrrolidin-1-yl)pyrazolo[1,5-a]pyridine-3-carboxylate (X-1) (51 mg, 0.14 mmol) in THF:MeOH:H$_2$O 3:2:1 (3 mL) was added LiOH (29 mg, 0.7 mmol). The reaction was heated to 50° C. for 48 hours then cooled to room temperature and neutralized to pH 6 with 1M NaOH. The mixture was reduced to dryness and purified by column chromatography on silica gel with DCM/MeOH gradient as eluant to yield 5-((2R,4S)-4-fluoro-2-(3-fluorophenyl)pyrrolidin-1-yl)pyrazolo[1,5-a]pyridine-3-carboxylic acid (X-3). $^1$H NMR (400 MHz, CDCl$_3$) δ 8.26 (s, 1 H), 8.15 (d, J=7.6 Hz, 1 H), 7.36-7.29 (m, 1 H), 7.09-7.04 (m, 2 H), 7.00-6.92 (m, 2 H), 6.24 (dd, J=2.4, 7.6 Hz, 1 H), 5.41 (d, J=52.8 Hz, 1 H), 5.06 (t, J=8.4 Hz, 1 H), 4.29-3.92 (m, 2 H), 2.94-2.82 (m, 1 H), 2.24-2.05 (m, 1 H). MS m/z 344.1 (M+1)$^+$.

Synthesis of 5-((2R,4S)-4-fluoro-2-(3-fluorophenyl)pyrrolidin-1-yl)pyrazolo[1,5-a]pyridine-3-carboxamide (X-5)

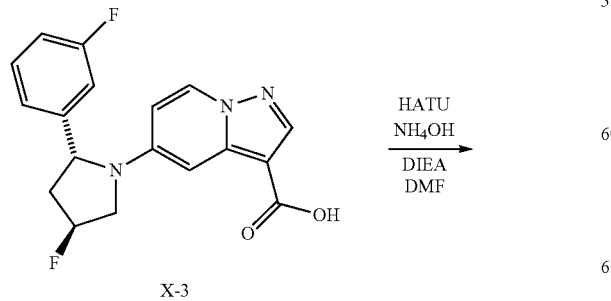

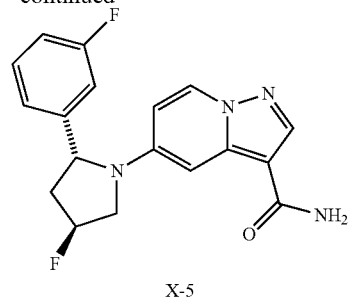

To a solution of 5-((2R,4S)-4-fluoro-2-(3-fluorophenyl)pyrrolidin-1-yl)pyrazolo[1,5-a]pyridine-3-carboxylic acid (X-3) (42 mg, 0.12 mmol) in DMF (1 mL) was added DIEA (64 µL, 0.36 mmol) and HATU (51 mg, 0.13 mmol). The reaction was stirred at room temperature for 10 minutes, then a solution of NH$_4$Cl (20 mg, 0.36 mmol) in NH$_4$OH (100 µL) was added and stirred for 3 hours. The crude reaction mixture was diluted with EtOAc and washed with water, brine, dried over magnesium sulfate, filtered and reduced to dryness. Purification by column chromatography on silica gel with DCM/MeOH gradient as eluant gave 5-((2R,4S)-4-fluoro-2-(3-fluorophenyl)pyrrolidin-1-yl)pyrazolo[1,5-a]pyridine-3-carboxamide (X-5). $^1$H NMR (400 MHz, CDCl$_3$) δ 8.10 (d, J=7.6 Hz, 1 H), 7.96 (s, 1H), 7.32 (td, J=6.0, 7.8 Hz, 1H), 7.20 (d, J=2.4 Hz, 1 H), 7.06 (d, J=7.6 Hz, 1 H), 6.99-6.90 (m, 2 H), 6.21 (dd, J=2.8, 7.6 Hz, 1 H), 5.40 (bs, 2 H), 5.38 (d, J=52.4 Hz, 1 H), 5.05 (dd, J=7.2, 9.2 Hz, 1 H), 4.18-3.92 (m, 2 H), 2.92-2.80 (m, 1 H), 2.11 (dddd, J=3.6, 9.2, 13.2, 40.0 Hz, 1 H). MS m/z 343.1 (M+1)$^+$.

Synthesis of ethyl 5-((2R,4S)-2-(3-cyano-5-fluorophenyl)-4-fluoropyrrolidin-1-yl)pyrazolo[1,5-a]pyridine-3-carboxylate (X-7)

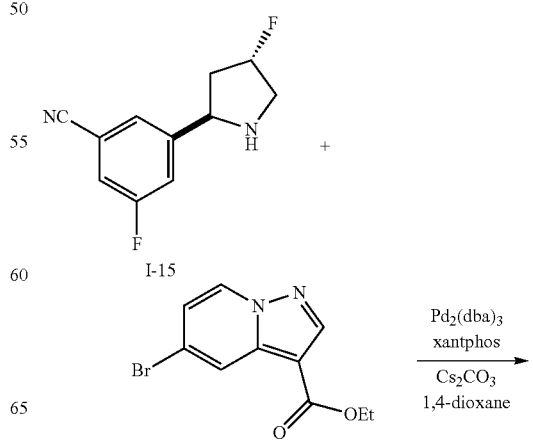

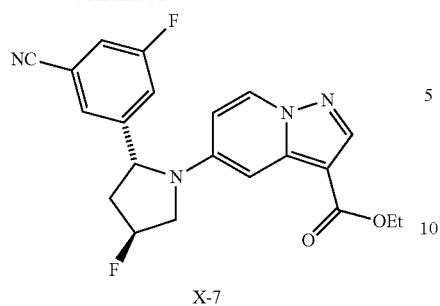

X-7

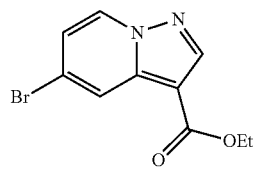

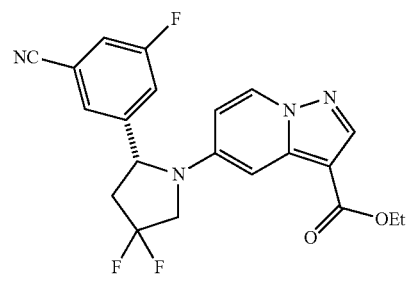

X-8

A N₂ purged flask was charged with ethyl 5-bromopyrazolo[1,5-a]pyridine-3-carboxylate (36 mg, 0.13 mmol), tris(dibenzylideneacetone)dipalladium(0) (2.5 mg, 2 μmol), xantphos (6 mg, 8 μmol), cesium carbonate (61 mg, 0.19 mmol), 1,4-dioxane (0.5 mL) and 3-fluoro-5-((2R,4S)-4-fluoropyrrolidin-2-yl)benzonitrile (I-15) (28 mg, 0.13 mmol). The contents were heated to 140° C. for 25 minutes under microwave irradiation. Upon cooling to room temperature the reaction was partitioned with EtOAc and water. The organic layer was washed with water, brine, dried over magnesium sulfate, filtered and reduced to dryness. The crude product was purified by column chromatography on silica gel with EtOAc/hexanes gradient as eluant to yield ethyl 5-((2R,4S)-2-(3-cyano-5-fluorophenyl)-4-fluoropyrrolidin-1-yl)pyrazolo[1,5-a]pyridine-3-carboxylate (X-7). ¹H NMR (400 MHz, CDCl₃) δ 8.22 (s, 1 H), 8.21 (d, J=7.6 Hz, 1 H), 7.39 (s, 1 H), 7.31-7.27 (m, 1 H), 7.26-7.21 (m, 1 H), 6.94 (d, J=2.4 Hz, 1 H), 6.24 (dd, J=2.8, 7.6 Hz, 1 H), 5.40 (d, J=52.4 Hz, 1 H), 5.07 (dd, J=7.2, 9.6 Hz, 1 H), 4.35-4.26 (m, 2 H), 4.23-4.08 (m, 1 H), 4.05-3.93 (m, 1 H), 2.97-2.85 (m, 1 H), 2.17-1.99 (m, 1 H), 1.35 (t, J=7.2 Hz, 3 H). MS m/z 397.1 (M+1)⁺.

A N₂ purged flask was charged with ethyl 5-bromopyrazolo[1,5-a]pyridine-3-carboxylate (100 mg, 0.37 mmol), palladium acetate (1.7 mg, 7 μmol), xantphos (7 mg, 11 μmol), cesium carbonate (170 mg, 0.52 mmol), 1,4-dioxane (0.5 mL) and (R)-3-(4,4-difluoropyrrolidin-2-yl)-5-fluorobenzonitrile (I-24) (84 mg, 0.37 mmol). The contents were heated to 140° C. for 1 hour under microwave irradiation. Upon cooling to room temperature the reaction was partitioned with EtOAc and water. The organic layer was washed with water, brine, dried over magnesium sulfate, filtered and reduced to dryness. The crude product was purified by column chromatography on silica gel with EtOAc/hexanes gradient as eluant to yield (R)-ethyl 5-(2-(3-cyano-5-fluorophenyl)-4,4-difluoropyrrolidin-1-yl)pyrazolo[1,5-a]pyridine-3-carboxylate (X-8). ¹H NMR (400 MHz, CDCl₃) δ 8.26 (d, J=7.6 Hz, 1 H), 8.24 (s, 1 H), 7.38 (s, 1 H), 7.33-7.29 (m, 1 H), 7.25-7.21 (m, 1 H), 6.93 (d, J=2.8 Hz, 1 H), 6.19 (dd, J=2.8, 7.6 Hz, 1 H), 5.14 (dd, J=4.4, 9.2 Hz, 1 H), 4.34-4.25 (m, 2 H), 4.25-4.16 (m, 1 H), 4.05-3.93 (m, 1 H), 3.14-2.98 (m, 1 H), 2.53-2.42 (m, 1 H), 1.34 (t, J=7.2 Hz, 3 H). MS m/z 415.1 (M+1)⁺.

Synthesis of (R)-ethyl 5-(2-(3-cyano-5-fluorophenyl)-4,4-difluoropyrrolidin-1-yl)pyrazolo[1,5-a]pyridine-3-carboxylate (X-8)

Synthesis of (R)-5-(2-(3-carbamoyl-5-fluorophenyl)-4,4-difluoropyrrolidin-1-yl)pyrazolo[1,5-a]pyridine-3-carboxamide (X-9)

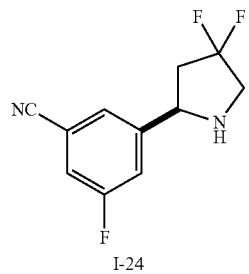

I-24

+

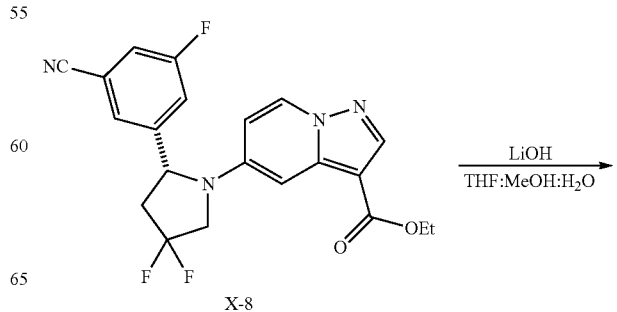

X-8

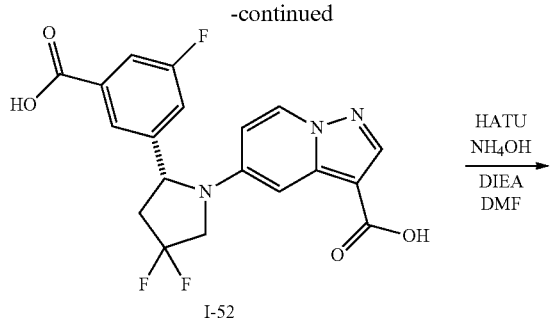

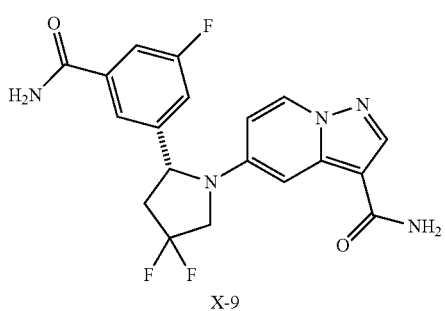

A solution of (R)-ethyl 5-(2-(3-cyano-5-fluorophenyl)-4,4-difluoropyrrolidin-1-yl)pyrazolo[1,5-a]pyridine-3-carboxylate (X-8) (90 mg, 0.22 mmol) in THF:MeOH:H$_2$O 3:2:1 (2.5 mL) was added LiOH (46 mg, 1.1 mmol) and stirred at 50° C. for 12 hours. The reaction was subsequently neutralized and concentrated to dryness. The crude product was purified by column chromatography on silica gel with DCM/MeOH gradient as eluant to yield (R)-5-(2-(3-carboxy-5-fluorophenyl)-4,4-difluoropyrrolidin-1-yl)pyrazolo[1,5-a]pyridine-3-carboxylic acid (I-52), which was immediately used in the next reaction. MS m/z 406.1 (M+1)$^+$.

To a solution of (R)-5-(2-(3-carboxy-5-fluorophenyl)-4,4-difluoropyrrolidin-1-yl)pyrazolo[1,5-a]pyridine-3-carboxylic acid (I-52) (54 mg, 0.13 mmol) in DMF (2 mL) was added DIEA (116 µL, 0.67 mmol) and HATU (126 mg, 0.33 mmol). The reaction was stirred for 30 minutes, then a solution of NH$_4$Cl (29 mg, 0.52 mmol) in NH$_4$OH (0.25 mL) was added and stirring continued for 2 hours. The crude reaction mixture was diluted with EtOAc and washed with water, brine, dried over magnesium sulfate, filtered and reduced to dryness. Purification by column chromatography on silica gel with DCM/MeOH gradient as eluant gave (R)-5-(2-(3-carbamoyl-5-fluorophenyl)-4,4-difluoropyrrolidin-1-yl)pyrazolo[1,5-a]pyridine-3-carboxamide (X-9). $^1$H NMR (400 MHz, CD$_3$OD) δ 8.24 (d, J=7.6 Hz, 1 H), 8.19 (s, 1 H), 7.65 (s, 1 H), 7.46 (d, J=8.4 Hz, 1 H), 7.22 (d, J=9.2 Hz, 1 H), 7.04 (d, J=2.4 Hz, 1 H), 6.44 (dd, J=2.8, 7.6 Hz, 1 H), 5.25 (dd, J=4.4, 8.8 Hz, 1 H), 4.26 (q, J=11.6 Hz, 1 H), 3.99 (q, J=14.0 Hz, 1 H), 3.20-3.02 (m, 1 H), 2.52-2.40 (m, 1 H). MS m/z 404.1 (M+1)$^+$.

Synthesis of 5-((2R,4S)-2-(3-cyano-5-fluorophenyl)-4-fluoropyrrolidin-1-yl)pyrazolo[1,5-a]pyridine-3-carboxamide (X-10)

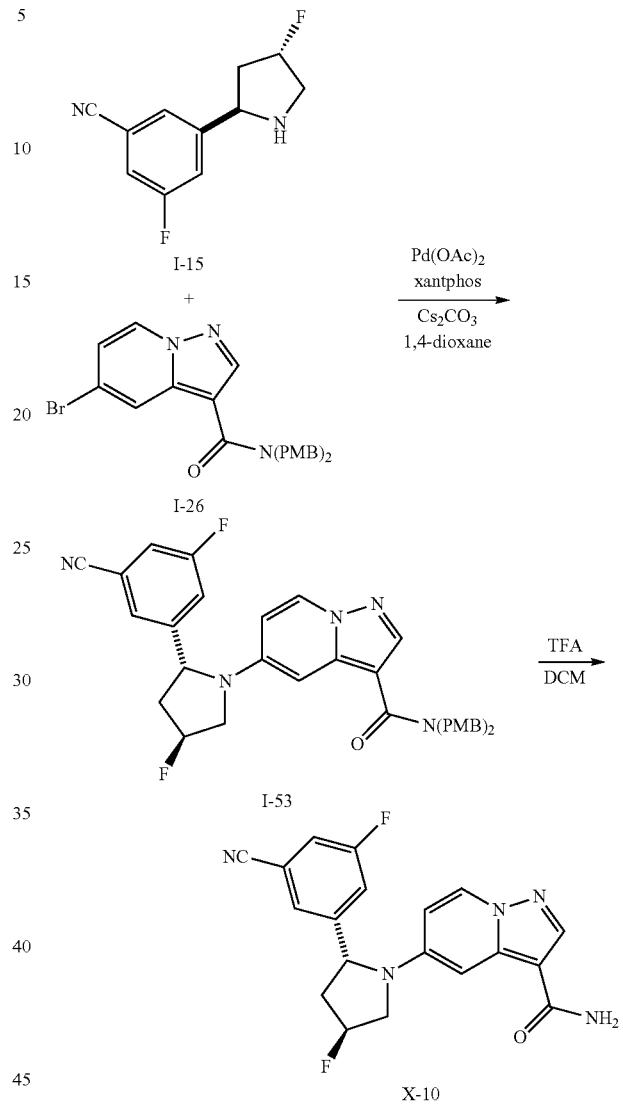

Method A

A N$_2$ purged flask was charged with 5-bromo-N,N-bis(4-methoxybenzyl)pyrazolo[1,5-a]pyridine-3-carboxamide (I-26) (25 mg, 0.05 mmol), palladium acetate (1.0 mg, 5.1 µmol), xantphos (4.5 mg, 7.8 µmol), cesium carbonate (24 mg, 0.07 mmol), 1,4-dioxane (0.25 mL) and 3-fluoro-5-((2R,4S)-4-fluoropyrrolidin-2-yl)benzonitrile (I-15) (11 mg, 0.05 mmol). The contents were heated to 140° C. for 30 minutes under microwave irradiation. Upon cooling to room temperature the reaction was partitioned with EtOAc and water. The organic layer was washed with water, brine, dried over magnesium sulfate, filtered and reduced to dryness. The crude product was purified by column chromatography on silica gel with EtOAc/hexanes gradient as eluant to yield 5-((2R,4S)-2-(3-cyano-5-fluorophenyl)-4-fluoropyrrolidin-1-yl)-N,N-bis(4-methoxybenzyl)pyrazolo[1,5-a]pyridine-3-carboxamide (I-53). $^1$H NMR (400 MHz, CDCl$_3$) δ 8.14 (d, J=7.6 Hz, 1 H), 7.78 (s, 1 H), 7.38 (s, 1 H), 7.30-7.26 (m, 1 H), 7.25-7.23 (m, 1 H), 7.22-7.16 (m, 5 H), 6.92-6.87 (m, 4 H), 6.16 (dd, J=2.4, 7.6 Hz, 1 H), 5.40 (d, J=52.4 Hz, 1 H), 5.09 (dd, J=6.8, 9.2 Hz, 1 H), 4.74 (d, J=16.0 Hz, 2 H), 4.50 (d, J=15.6 Hz, 2 H), 4.22-3.94 (m, 2 H), 3.82 (s, 6 H), 2.96-2.84 (m, 1 H), 2.07 (dddd, J=4.0, 9.6, 13.6, 40.0 Hz, 1 H). MS m/z 608.1 (M+1)$^+$.

A solution of 5-((2R,4S)-2-(3-cyano-5-fluorophenyl)-4-fluoropyrrolidin-1-yl)-N,N-bis(4-methoxybenzyl)pyrazolo[1,5-a]pyridine-3-carboxamide (I-53) (10 mg, 0.02 mmol) in DCM (0.5 mL) was added TFA (0.5 mL) and heated to 50° C. for 12 hours. The reaction was reduced to dryness and purified by column chromatography on silica gel with DCM/MeOH gradient as eluant to yield 5-((2R,4S)-2-(3-cyano-5-fluorophenyl)-4-fluoropyrrolidin-1-yl)pyrazolo[1,5-a]pyridine-3-carboxamide (X-10). $^1$H NMR (400 MHz, CD$_3$OD) δ 8.28 (d, J=8.0 Hz, 1 H), 8.23 (s, 1 H), 7.61 (m, 1 H), 7.48-7.42 (m, 1 H), 7.03 (d, J=2.4 Hz, 1 H), 6.52 (dd, J=2.8, 7.6 Hz, 1 H), 5.42 (d, J=52.4 Hz, 1 H), 5.14 (dd, J=7.2, 9.6 Hz, 1 H), 4.21 (ddd, J=3.2, 12.0, 36.8 Hz, 1 H), 3.94 (ddd, J=2.0, 12.4, 23.6 Hz, 1 H), 2.98-2.85 (m, 1 H), 2.16 (dddd, J=3.6, 9.6, 14.0, 40.4 Hz, 1 H). MS m/z 368.1 (M+1)$^+$.

Method B

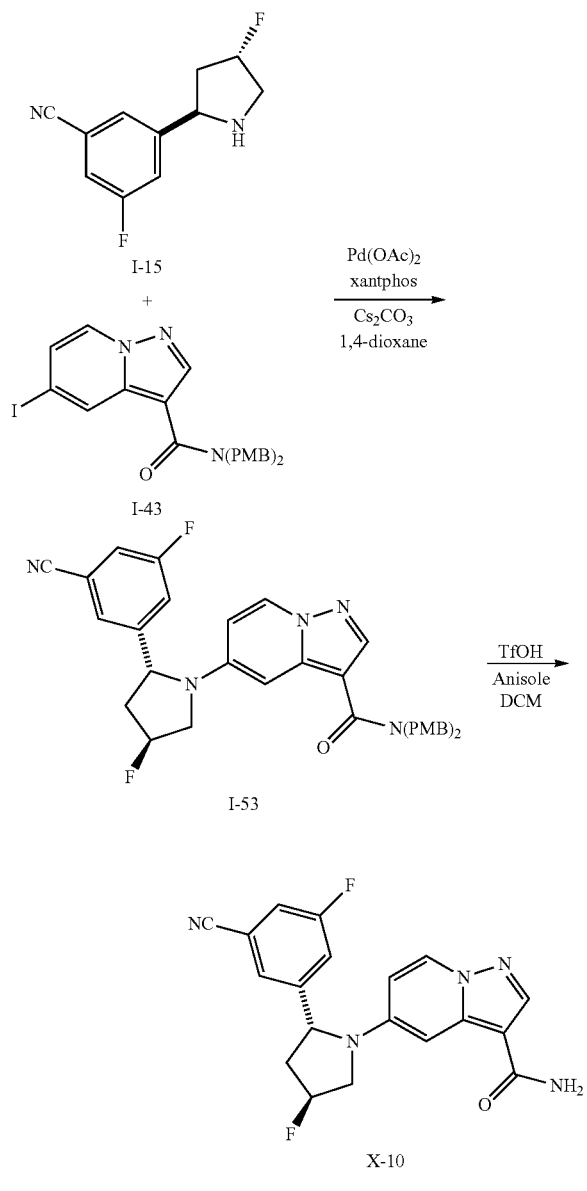

A 3 L flask was charged with 3-fluoro-5-((2R,4S)-4-fluoropyrrolidin-2-yl)benzonitrile (I-15) (50 g, 240 mmol), 5-iodo-N,N-bis(4-methoxybenzyl)pyrazolo[1,5-a]pyridine-3-carboxamide (I-43) (158 g, 290 mmol), Cs$_2$CO$_3$ (133 g, 408 mmol) and 1,4-dioxane (1125 mL). The reaction was heated to 98° C. and maintained for 30 minutes. Pd(OAc)$_2$ (3.5 g, 15.6 mmol) and Xantphos (9.5 g, 16.4 mmol) were added and the reaction was heated to 102° C., and maintained for 3 hours. After 3 hours, additional 5-iodo-N,N-bis(4-methoxybenzyl)pyrazolo[1,5-a]pyridine-3-carboxamide (I-43) (7 g, 13.3 mmol) was added and maintained at 102° C. for 1 hour. HPLC analysis (UV=215 nm) was used to monitor the reaction. The mixture was cooled to 20° C. and water (500 mL) and EtOAc (2 L) were added. The above procedure was repeated on the same scale and the two runs were combined. The suspension was filtered through 200 g of silica gel and concentrated to dryness under vacuum to give a dark brown sticky solid. The solids were dissolved in i-PrOAc (3 L) with heat and washed with water (500 mL). The organic layer was concentrated to dryness to give a dark brown solid. The solids were purified by column chromatography on silica gel with 50% EtOAc in heptanes as eluant to yield 5-((2R,4S)-2-(3-cyano-5-fluorophenyl)-4-fluoropyrrolidin-1-yl)-N,N-bis(4-methoxybenzyl)pyrazolo[1,5-a]pyridine-3-carboxamide (I-53). Melting point: 90° C. (dec.). $^1$H NMR (400 MHz, CDCl$_3$) δ 8.14 (d, J=7.6 Hz, 1 H), 7.78 (s, 1 H), 7.38 (s, 1 H), 7.30-7.26 (m, 1 H), 7.25-7.23 (m, 1 H), 7.22-7.16 (m, 5 H), 6.92-6.87 (m, 4 H), 6.6 (dd, J=2.4, 7.6 Hz, 1 H), 5.40 (d, J=52.4 Hz, 1 H), 5.09 (dd, J=6.8, 9.2 Hz, 1 H), 4.74 (d, J=16.0 Hz, 2 H), 4.50 (d, J=15.6 Hz, 2 H), 4.22-3.94 (m, 2 H), 3.82 (s, 6 H), 2.96-2.84 (m, 1 H), 2.18-2.05 (m, 1 H).

A flask was charged with TfOH (136.4 g, 909 mmol) and DCM (505 mL) and cooled to −20° C. Anisole (45 g, 416 mmol) was added followed by a solution of 5-((2R,4S)-2-(3-cyano-5-fluorophenyl)-4-fluoropyrrolidin-1-yl)-N,N-bis(4-methoxybenzyl)pyrazolo[1,5-a]pyridine-3-carboxamide (I-53) (101 g, 166 mmol) in DCM (303 mL). The mixture was warmed to 20° C., and maintained for 15 hours. HPLC showed consumption of (I-53). The reaction was cooled to <0° C. and DCM (1 L) and an aqueous saturated K$_2$CO$_3$ (1 L) was added (aqueous layer pH=9-10). The aqueous layer was separated and extracted with DCM (500 mL). The rag layer was filtered through Celite and the two layers were separated. The organic layers were combined and concentrated to dryness. The resulting solid was triturated with TBME (250 mL) at 20° C. to yield 5-((2R,4S)-2-(3-cyano-5-fluorophenyl)-4-fluoropyrrolidin-1-yl)pyrazolo[1,5-a]pyridine-3-carboxamide (X-10). Melting point: 140° C. (dec.). $^1$H NMR (400 MHz, CD$_3$OD) δ 8.28 (d, J=8.0 Hz, 1 H), 8.23 (s, 1 H), 7.61-7.58 (m, 1 H), 7.48-7.42 (m, 1 H), 7.03 (d, J=2.4 Hz, 1 H), 6.52 (dd, J=2.8, 7.6 Hz, 1 H), 5.42 (d, J=52.4 1 H), 5.14 (dd, J=7.2, 9.6 Hz, 1 H), 4.21 (ddd, J=3.2, 12.0, 36.8 Hz, 1 H), 3.94 (ddd, J=2.0, 12.3, 23.8 Hz, 1 H), 2.98-2.85 (m, 1 H), 2.16 (dddd, J=3.6, 9.6, 14.0, 40.4 Hz, 1 H).

Synthesis of Ethyl 5-((2R,4S)-4-cyano-2-(3-fluorophenyl)pyrrolidin-1-yl)pyrazolo[1,5-a]pyridine-3-carboxylate (X-19) and ethyl 5-((2R,4S)-4-carbamoyl-2-(3-fluorophenyl)pyrrolidin-1-yl)pyrazolo[1,5-a]pyridine-3-carboxylate (X-20)

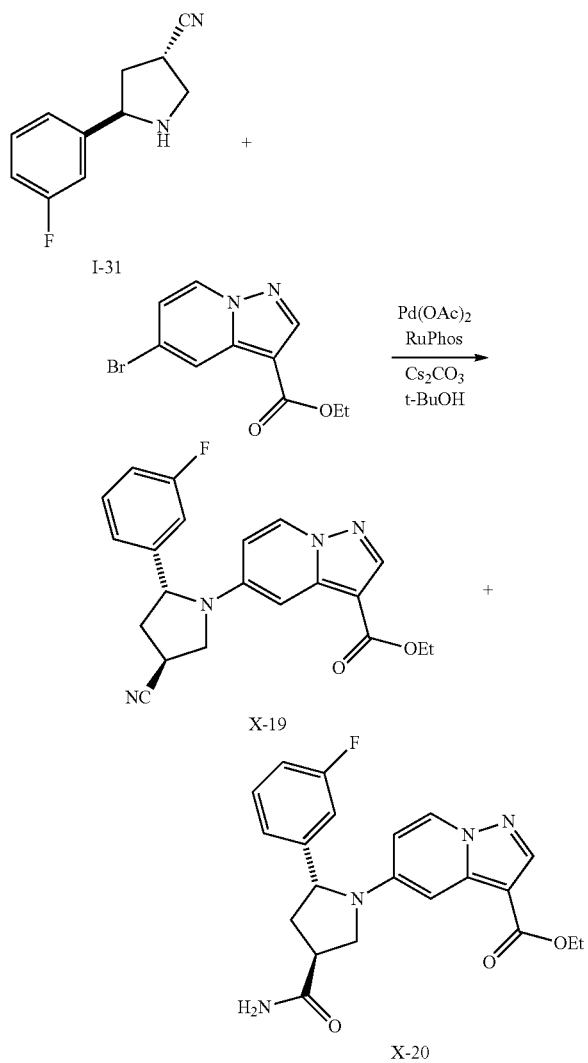

A $N_2$ purged flask was charged with ethyl 5-bromopyrazolo[1,5-a]pyridine-3-carboxylate (30 mg, 0.11 mmol), palladium acetate (1.0 mg, 5 μmol), RuPhos (5 mg, 10 μmol), cesium carbonate (65 mg, 0.20 mmol), tBuOH (0.5 mL) and (3S,5R)-5-(3-fluorophenyl)pyrrolidine-3-carbonitrile 2,2,2-trifluoroacetate (I-31) (30 mg, 0.10 mmol). The contents were heated to 120° C. overnight in an oil bath. Upon cooling to room temperature the reaction was filtered through celite and concentrated. The crude product was purified by column chromatography on silica gel with an EtOAc/hexane gradient as eluant to yield ethyl 5-((2R,4S)-4-cyano-2-(3-fluorophenyl)pyrrolidin-1-yl)pyrazolo[1,5-a]pyridine-3-carboxylate (X-19). $^1$H NMR (400 MHz, CDCl3) δ 8.25 (s, 1 H), 8.22 (d, J=7.6 Hz, 1 H), 7.40-7.32 (m, 1 H), 7.07-6.96 (m, 3 H), 6.88 (d, J=9.4 Hz, 1 H), 6.24 (dd, J=2.7, 7.6 Hz, 1 H), 5.10 (dd, J=2.5, 8.0 Hz, 1 H), 4.39-4.29 (m, 2 H), 4.23-4.14 (m, 1 H), 3.95-3.78 (m, 1 H), 3.42-3.29 (m, 1 H), 2.92-2.78 (m, 1 H), 2.50-2.39 (m, 1 H), 1.36 (t, J=7.1 Hz, 3 H). MS m/z 379.1 (M+1)$^+$. Further elution with MeOH/DCM gradient afforded ethyl 5-((2R,4S)-4-carbamoyl-2-(3-fluorophenyl)pyrrolidin-1-yl)pyrazolo[1,5-a]pyridine-3-carboxylate (X-20). MS m/z 397.1 (M+1)$^+$.

Synthesis of Benzyl (5-((2R,4S)-4-fluoro-2-(3-fluorophenyl)pyrrolidin-1-yl)pyrazolo[1,5-a]pyridin-3-yl)carbamate (X-21)

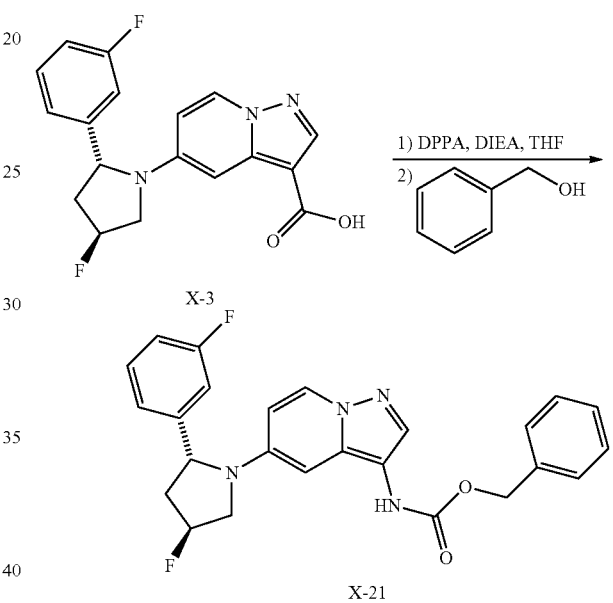

To a solution of 5-((2R,4S)-4-fluoro-2-(3-fluorophenyl)pyrrolidin-1-yl)pyrazolo[1,5-a]pyridine-3-carboxylic acid (X-3) (50 mg, 0.15 mmol) and DIEA (0.052 mL, 0.30 mmol) in THF (0.75 mL) under $N_2$ was added DPPA (0.035 mL, 0.17 mmol) and the reaction was stirred overnight at room temperature. Benzyl alcohol (0.025 mL, 0.24 mmol) was added to the reaction and the mixture was heated to 65° C. for 3 days. Upon cooling to room temperature the reaction was partitioned with EtOAc and aqueous saturated NaHCO$_3$. The organics were dried over Na$_2$SO$_4$, filtered, and concentrated. The crude product was purified by column chromatography on silica gel with an EtOAc/hexane gradient as eluant to yield benzyl (5-((2R,4S)-4-fluoro-2-(3-fluorophenyl)pyrrolidin-1-yl)pyrazolo[1,5-a]pyridin-3-yl)carbamate (X-21). $^1$H NMR (400 MHz, CDCl3) δ 8.03 (d, J=8.2 Hz, 1 H), 7.78 (s, 1 H), 7.52-7.25 (m, 6 H), 7.01 (d, J=7.6 Hz, 1 H), 6.98-6.84 (m, 2 H), 6.13 (d, J=6.9 Hz, 2 H), 5.36 (d, J=52.9 Hz, 1 H), 5.20 (s, 2 H), 5.03-4.86 (m, 1 H), 4.17-3.93 (m, 1 H), 3.93-3.72 (m, 1 H), 2.92-2.73 (m, 1 H), 2.16-1.97 (m, 1 H). MS m/z 449.1 (M+1)$^+$.

Synthesis of 1-(5-((2R,4S)-4-fluoro-2-(3-fluorophenyl)pyrrolidin-1-yl)pyrazolo[1,5-a]pyridin-3-yl)urea (X-23)

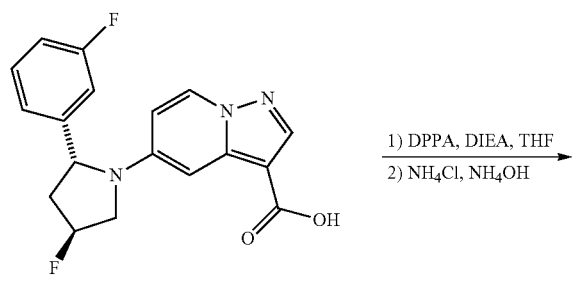

To a solution of 5-((2R,4S)-4-fluoro-2-(3-fluorophenyl)pyrrolidin-1-yl)pyrazolo[1,5-a]pyridine-3-carboxylic acid (X-3) (50 mg, 0.15 mmol) and DIEA (0.052 mL, 0.30 mmol) in THF (0.75 mL) under $N_2$ was added DPPA (0.035 mL, 0.17 mmol) and the reaction was stirred overnight at room temperature. $NH_4Cl$ (42 mg, 0.73 mmol) and $NH_4OH$ were added to the reaction and the mixture was heated to 65° C. overnight. Upon cooling to room temperature the reaction was concentrated, taken up in MeOH and filtered. The filtrate was purified by preparative LCMS and lyophilized to give 1-(5-((2R,4S)-4-fluoro-2-(3-fluorophenyl)pyrrolidin-1-yl)pyrazolo[1,5-a]pyridin-3-yl)urea (X-23). $^1$H NMR (400 MHz, MeOD) δ 8.19-8.08 (m, 1 H), 7.83-7.67 (m, 1 H), 7.35 (dd, J=7.8, 14.0 Hz, 1 H), 7.16 (d, J=7.6 Hz, 1H), 7.11-7.01 (m, 1 H), 6.97 (t, J=8.5 Hz, 1 H), 6.44 (bd, J=5.7 Hz, 1 H), 6.26 (bs, 1 H), 5.40 (d, J=52.9 Hz, 1 H), 5.12-4.99 (m, 1 H), 4.16 (dd, J=11.4, 35.7 Hz, 1 H), 3.87 (dd, J=12.0, 23.4 Hz, 1 H), 2.93-2.77 (m, 1 H), 2.24-2.04 (m, 1 H). MS m/z 358.1 (M+1)$^+$.

Synthesis of 5-((2R,4S)-4-cyano-2-(3-fluorophenyl)pyrrolidin-1-yl)pyrazolo[1,5-a]pyridine-3-carboxamide (X-25)

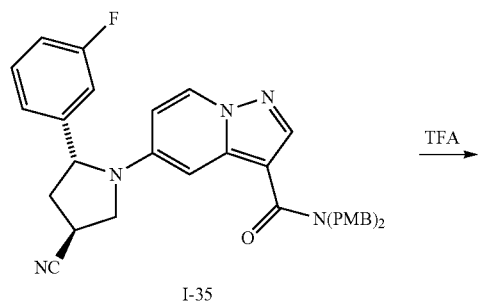

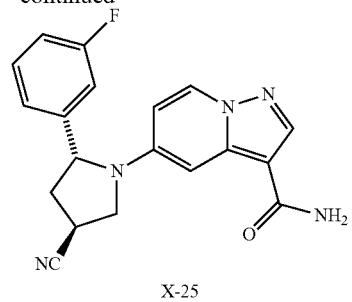

A solution of 5-((2R,4S)-4-cyano-2-(3-fluorophenyl)pyrrolidin-1-yl)-N,N-bis(4-methoxybenzyl)pyrazolo[1,5-a]pyridine-3-carboxamide (I-35) (15 mg, 0.025 mmol) in TFA (0.5 mL) was heated to 60° C. for 2 hours. The reaction was reduced to dryness and the crude material was taken up in DMSO and purified by preparative LCMS and lyophilized to give 5-((2R,4S)-4-cyano-2-(3-fluorophenyl)pyrrolidin-1-yl)pyrazolo[1,5-a]pyridine-3-carboxamide (X-25). $^1$H NMR (400 MHz, $CD_3CN$) δ 8.22 (d, J=7.8 Hz, 1 H), 8.05 (s, 1 H), 7.43-7.28 (m, 1 H), 7.10 (d, J=7.7 Hz, 1 H), 7.06-6.96 (m, 3 H), 6.38 (dd, J=2.8, 7.7 Hz, 1 H), 5.09 (dd, J=3.0, 8.1 Hz, 1 H), 4.18 (dd, J=7.6, 9.6 Hz, 1 H), 3.82-3.70 (m, 1 H), 3.49-3.34 (m, 1 H), 2.86-2.68 (m, 1 H), 2.38-2.28 (m, 1 H). MS m/z 350.1 (M+1)$^+$.

Synthesis of 5-((2R,4S)-4-carbamoyl-2-(3-fluorophenyl)pyrrolidin-1-yl)pyrazolo[1,5-a]pyridine-3-carboxamide (X-26)

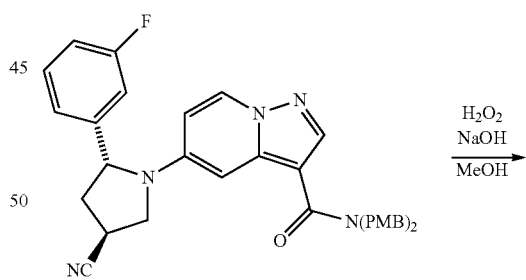

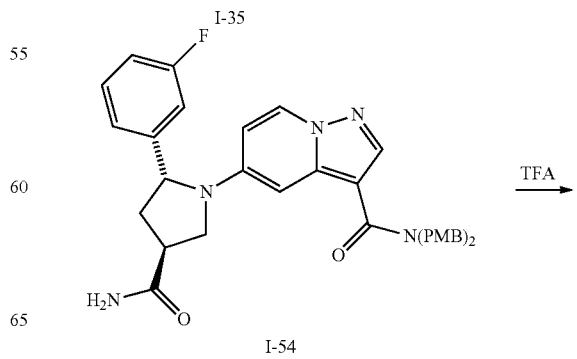

-continued

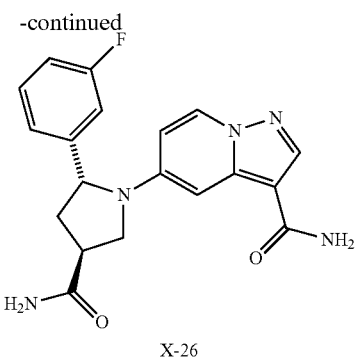

X-26

A solution of 5-((2R,4S)-4-cyano-2-(3-fluorophenyl)pyrrolidin-1-yl)-N,N-bis(4-methoxybenzyl)pyrazolo[1,5-a]pyridine-3-carboxamide (I-35) (25 mg, 0.042 mmol) in MeOH (1 mL) was cooled to 0° C. A 1M NaOH solution (0.17 mL, 0.17 mmol) and 30% $H_2O_2$ (0.01 mL) were added to the reaction and stirred at 0° C. for 1 hour followed by room temperature for 1 hour. The reaction was concentrated to dryness and the residue was partitioned between EtOAc and $H_2O$. The aqueous layer was extracted twice with EtOAc and the combined organics were dried over $Na_2SO_4$, filtered, and concentrated. The residue was purified by silica chromatography with EtOAc/hexane gradient as eluent to yield 5-((2R,4S)-4-carbamoyl-2-(3-fluorophenyl)pyrrolidin-1-yl)-N,N-bis(4-methoxybenzyl)pyrazolo[1,5-a]pyridine-3-carboxamide (I-54). $^1$H NMR (400 MHz, $CDCl_3$) δ 8.09 (d, J=7.7 Hz, 1 H), 7.78 (s, 1 H), 7.32-7.27 (m, 1H), 7.18 (d, J=8.5 Hz, 4 H), 7.14-7.09 (m, 1 H), 7.00-6.92 (m, 2 H), 6.89 (d, J=8.6 Hz, 4 H), 6.85 (s, 1 H), 6.15 (dd, J=2.7, 7.6 Hz, 1 H), 5.75 (bs, 1 H), 5.54 (bs, 1 H), 5.05 (d, J=7.7 Hz, 1 H), 4.72 (d, J=15.7 Hz, 2 H), 4.51 (d, J=15.8 Hz, 2 H), 4.04-3.97 (m, 1H), 3.88-3.82 (m, 1 H), 3.81 (s, 6 H), 3.23-3.11 (m, 1 H), 2.87-2.73 (m, 1 H), 2.19 (ddd, J=1.4, 6.5, 12.3 Hz, 1 H). MS m/z 608.3 $(M+1)^+$.

A solution of 5-((2R,4S)-4-carbamoyl-2-(3-fluorophenyl)pyrrolidin-1-yl)-N,N-bis(4-methoxybenzyl)pyrazolo[1,5-a]pyridine-3-carboxamide (I-54) (10 mg, 0.016 mmol) in TFA (0.5 mL) was heated to 60° C. for 2 hours. The reaction was reduced to dryness and the crude material was taken up in DMSO and purified by preparative LCMS and lyophilized to give 5-((2R,4S)-4-carbamoyl-2-(3-fluorophenyl)pyrrolidin-1-yl)pyrazolo[1,5-a]pyridine-3-carboxamide (X-26). $^1$H NMR (400 MHz, DMSO) δ 8.38 (d, J=7.7 Hz, 1 H), 8.26 (s, 1 H), 7.53 (s, 1 H), 7.44-7.31 (m, 1H), 7.15-7.01 (m, 2 H), 6.96 (s, 1 H), 6.31 (d, J=7.1 Hz, 1 H), 5.13 (d, J=8.0 Hz, 1 H), 3.98-3.85 (m, 1 H), 3.65-3.54 (m, 1 H), 3.20-3.07 (m, 1 H), 2.60-2.52 (m, 1 H), 2.08 (dd, J=6.9, 12.0 Hz, 1 H). MS m/z 368.1 $(M+1)^+$.

By repeating the procedures described in the above examples, using appropriate starting materials, the following compounds of Formula I, as identified in Table 1, were obtained.

TABLE 1

| Ex. No. | STRUCTURE | NMR and LC/MS | BaF3/ TRKA-NGF | Ba/ F3Tel-TrkA | BAF3/ WT |
|---|---|---|---|---|---|
| X-1 | 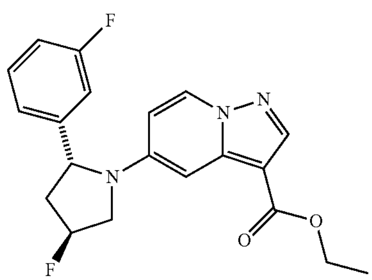 [SMILES: CCOC(=O)c1cnn2ccc(N3C[C@@H](F)C[C@@H]3c3cccc(F)c3)cc12] | $^1$H NMR (400 MHz, $CDCl_3$) δ 8.20 (s, 1 H), 8.16 (d, J = 7.6 Hz, 1 H), 7.31 (td, J = 5.6, 7.6 Hz, 1 H), 7.05 (d, J = 7.6 Hz, 1 H), 6.98 (d, J = 2.8 Hz, 1 H), 6.96-6.91 (m, 2 H), 6.24 (dd, J = 2.8, 8.0 Hz, 1 H), 5.39 (d, J = 52.8 Hz, 1 H), 5.04 (dd, J = 7.2, 9.2 Hz, 1 H), 4.34-4.26 (m, 2 H), 4.17-3.90 (m, 2H), 2.93-2.81 (m, 1 H), 2.11 (dddd, J = 3.6, 9.2, 13.2, 40.8 Hz, 1 H). MS m/z 372.1 $(M + 1)^+$. | 0.001 | 0.0 | 4.1 |
| X-2 | 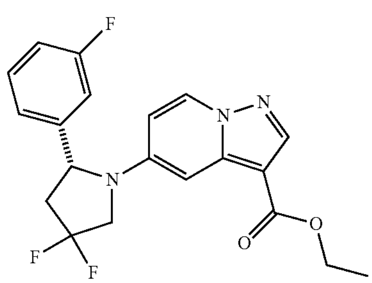 [SMILES: CCOC(=O)c1cnn2ccc(N3CC(F)(F)C[C@@H]3c3cccc(F)c3)cc12] | $^1$H NMR (400 MHz, $CDCl_3$) δ 8.22 (s, 1 H), 8.19 (d, J = 7.6 Hz, 1 H), 7.34 (td, J = 5.6, 7.6 Hz, 1 H), 7.05 (d, J = 7.6 Hz, 1 H), 7.02-6.93 (m, 3 H), 6.22 (dd, J = 2.8, 8.0 Hz, 1 H), 5.11 (dd, J = 5.2, 8.8 Hz, 1 H), 4.35-4.27 (m, 2 H), 4.19 (q, J = 11.2 Hz, 1 H), 4.00 (q, J = 12.8 Hz, 1 H), 3.10-2.95 (m, 1 H), 2.56-2.44 (m, 1 H), 1.35 (t, J = 7.2 Hz, 3 H). MS m/z 390.1 $(M + 1)^+$. | 0.003 | 0.003 | >10 |

TABLE 1-continued

| Ex. No. | STRUCTURE | NMR and LC/MS | BaF3/ TRKA-NGF | Ba/ F3Tel-TrkA | BAF3/ WT |
|---|---|---|---|---|---|
| X-3 | 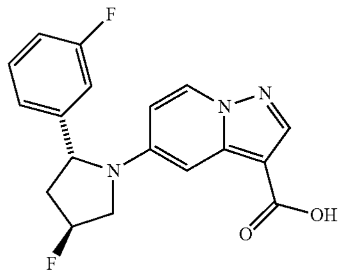 [SMILES: O=C(O)c1cnn2ccc(N3C[C@@H](F)C[C@@H]3c3cccc(F)c3)cc12] | $^1$H NMR (400 MHz, CDCl$_3$) δ 8.26 (s, 1 H), 8.15 (d, J = 7.6 Hz, 1 H), 7.36-7.29 (m, 1 H), 7.09-7.04 (m, 2 H), 7.00-6.92 (m, 2 H), 6.24 (dd, J = 2.4, 7.6 Hz, 1 H), 5.41 (d, J = 52.8 Hz, 1 H), 5.06 (t, J = 8.4 Hz, 1 H), 4.29-3.92 (m, 2 H), 2.94-2.82 (m, 1 H), 2.24-2.05 (m, 1 H). MS m/z 344.1 (M + 1)$^+$. | 0.11 | 0.147 | >10 |
| X-4 | 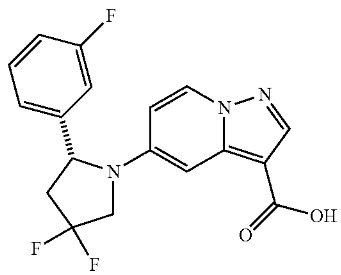 [SMILES: O=C(O)c1cnn2ccc(N3CC(F)(F)C[C@@H]3c3cccc(F)c3)cc12] | $^1$H NMR (400 MHz, CDCl$_3$) δ 8.29 (s, 1 H), 8.21 (d, J = 8.0 Hz, 1 H), 7.35 (td, J = 5.6, 8.0 Hz, 1 H), 7.09-6.95 (m, 4 H), 6.22 (dd, J = 2.8, 7.6 Hz, 1 H), 5.13 (dd, J = 5.2, 8.8 Hz, 1 H), 4.22 (q, J = 11.6 Hz, 1 H), 4.03 (q, J = 12.4 Hz, 1 H), 3.13-2.96 (m, 1 H), 2.60-2.46 (m, 1 H). MS m/z 362.1 (M + 1)$^+$. | 0.666 | 1.683 | >10 |
| X-5 | 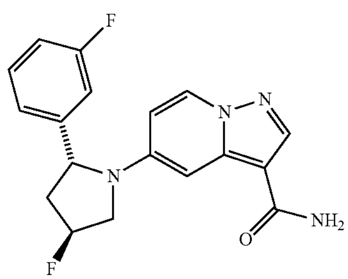 [SMILES: NC(=O)c1cnn2ccc(N3C[C@@H](F)C[C@@H]3c3cccc(F)c3)cc12] | $^1$H NMR (400 MHz, CDCl$_3$) δ 8.10 (d, J = 7.6 Hz, 1 H), 7.96 (s, 1 H), 7.32 (td, J = 6.0, 7.8 Hz, 1 H), 7.20 (d, J = 2.4 Hz, 1 H), 7.06 (d, J = 7.6 Hz, 1 H), 6.99-6.90 (m, 2 H), 6.21 (dd, J = 2.8, 7.6 Hz, 1 H), 5.40 (bs, 2 H), 5.38 (d, J = 52.4 Hz, 1 H), 5.05 (dd, J = 7.2, 9.2 Hz, 1 H), 4.18-3.92 (m, 2 H), 2.92-2.80 (m, 1 H), 2.11 (dddd, J = 3.6, 9.2, 13.2, 40.0 Hz, 1 H). MS m/z 343.1 (M + 1)$^+$. | 0.007 | 0.006 | >10 |
| X-6 | 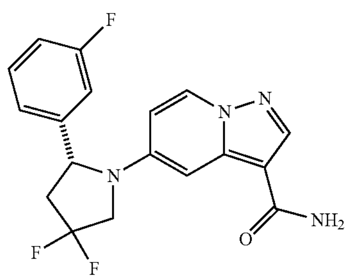 [SMILES: NC(=O)c1cnn2ccc(N3CC(F)(F)C[C@@H]3c3cccc(F)c3)cc12] | $^1$H NMR (400 MHz, CDCl$_3$) δ 8.16 (d, J = 7.6 Hz, 1 H), 7.99 (s, 1 H), 7.34 (td, J = 6.0, 8.0 Hz, 1 H), 7.18 (d, J = 2.4 Hz, 1 H), 7.05 (d, J = 8.0 Hz, 1 H), 7.01-6.92 (m, 2 H), 6.20 (dd, J = 2.8, 7.6 Hz, 1 H), 5.44 (bs, 2 H), 5.11 (dd, J = 4.8, 8.8 Hz, 1 H), 4.20 (q, J = 11.2 Hz, 1 H), 4.01 (q, J = 12.8, Hz, 1 H), 3.10-2.94 (m, 1 H), 2.56-2.42 (td, J = 4.8, 13.6 Hz, 1 H). MS m/z 361.1 (M + 1)$^+$. | 0.016 | 0.024 | >10 |
| X-7 | 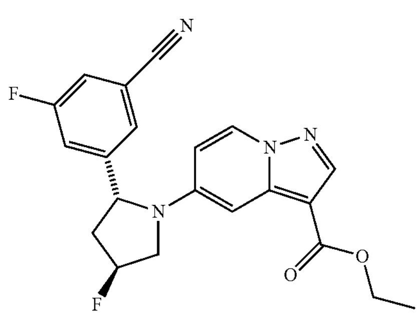 [SMILES: CCOC(=O)c1cnn2ccc(N3C[C@@H](F)C[C@@H]3c3cc(F)cc(C#N)c3)cc12] | $^1$H NMR (400 MHz, CDCl$_3$) δ 8.22 (s, 1 H), 8.21 (d, J = 7.6 Hz, 1 H), 7.39 (s, 1 H), 7.31-7.27 (m, 1 H), 7.26-7.21 (m, 1 H), 6.94 (d, J = 2.4 Hz, 1 H), 6.24 (dd, J = 2.8, 7.6 Hz, 1 H), 5.40 (d, J = 52.4 Hz, 1 H), 5.07 (dd, J = 7.2, 9.6 Hz, 1 H), 4.35-4.26 (m, 2 H), 4.23-4.08 (m, 1 H), 4.05-3.93 (m, 1 H), 2.97-2.85 (m, 1 H), 2.17-1.99 (m, 1 H), 1.35 (t, J = 7.2 Hz, 3 H). MS m/z 397.1 (M + 1)$^+$. | 0.002 | 0.001 | 4.49 |

TABLE 1-continued

| Ex. No. | STRUCTURE | NMR and LC/MS | BaF3/ TRKA- NGF | Ba/ F3Tel- TrkA | BAF3/ WT |
|---|---|---|---|---|---|
| X-8 | 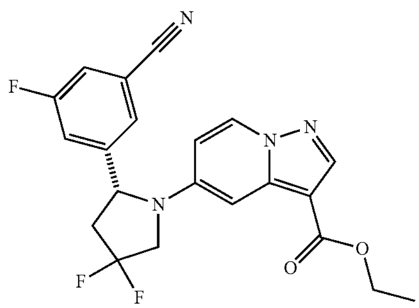 [SMILES: CCOC(=O)c1cnn2ccc(N3CC(F)(F)C[C@@H]3c3cc(F)cc(C#N)c3)cc12] | $^1$H NMR (400 MHz, CDCl$_3$) δ 8.26 (d, J = 7.6 Hz, 1 H), 8.24 (s, 1 H), 7.38 (s, 1 H), 7.33-7.29 (m, 1 H), 7.25-7.21 (m, 1 H), 6.93 (d, J = 2.8 Hz, 1 H), 6.19 (dd, J = 2.8, 7.6 Hz, 1 H), 5.14 (dd, J = 4.4, 9.2 Hz, 1 H), 4.34-4.25 (m, 2 H), 4.25-4.16 (m, 1 H), 4.05-3.93 (m, 1 H), 3.14-2.98 (m, 1 H), 2.53-2.42 (m, 1 H), 1.34 (t, J = 7.2 Hz, 3 H). MS m/z 415.1 (M + 1)$^+$. | 0.019 | 0.017 | >10 |
| X-9 | 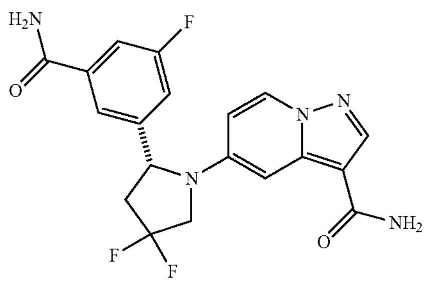 [SMILES: NC(=O)c1cc(F)cc([C@H]2CC(F)(F)CN2c2ccn3ncc(C(N)=O)c3c2)c1] | $^1$H NMR (400 MHz, CD$_3$OD) δ 8.24 (d, J = 7.6 Hz, 1 H), 8.19 (s, 1 H), 7.65 (s, 1 H), 7.46 (d, J = 8.4 Hz, 1 H), 7.22 (d, J = 9.2 Hz, 1 H), 7.04 (d, J = 2.4 Hz, 1 H), 6.44 (dd, J = 2.8, 7.6 Hz, 1 H), 5.25 (dd, J = 4.4, 8.8 Hz, 1 H), 4.26 (q, J = 11.6 Hz, 1 H), 3.99 (q, J = 14.0 Hz, 1 H), 3.20-3.02 (m, 1 H), 2.52-2.40 (m, 1 H). MS m/z 404.1 (M + 1)$^+$. | 0.048 | 0.037 | >10 |
| X-10 | 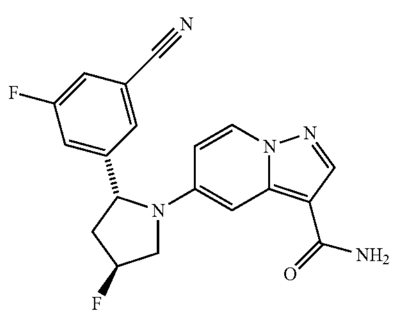 [SMILES: N#Cc1cc(F)cc([C@H]2C[C@H](F)CN2c2ccn3ncc(C(N)=O)c3c2)c1] | $^1$H NMR (400 MHz, CD$_3$OD) δ 8.28 (d, J = 8.0 Hz, 1 H), 8.23 (s, 1 H), 7.61 (m, 1 H), 7.48-7.42 (m, 1 H), 7.03 (d, J = 2.4 Hz, 1 H), 6.52 (dd, J = 2.8, 7.6 Hz, 1 H), 5.42 (d, J = 52.4 Hz, 1 H), 5.14 (dd, J = 7.2, 9.6 Hz, 1 H), 4.21 (ddd, J = 3.2, 12.0, 36.8 Hz, 1 H), 3.94 (ddd, J = 2.0, 12.4, 23.6 Hz, 1 H), 2.98-2.85 (m, 1 H), 2.16 (dddd, J = 3.6, 9.6, 14.0, 40.4 Hz, 1 H). MS m/z 368.1 (M + 1)$^+$. | 0.008 | 0.005 | >10 |
| X-11 | 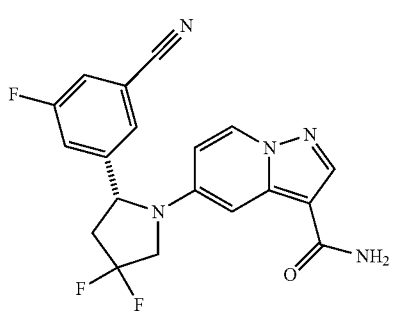 [SMILES: N#Cc1cc(F)cc([C@H]2CC(F)(F)CN2c2ccn3ncc(C(N)=O)c3c2)c1] | $^1$H NMR (400 MHz, CDCl$_3$) δ 8.23 (d, J = 7.6 Hz, 1 H), 8.02 (s, 1 H), 7.38 (s, 1 H), 7.31-7.27 (m, 1 H), 7.25-7.21 (m, 1 H), 7.17 (d, J = 2.4 Hz, 1 H), 6.18 (dd, J = 2.8, 7.6 Hz, 1 H), 5.62 (bs, 2 H), 5.15 (dd, J = 4.0, 9.2 Hz, 1 H), 4.21-4.16 (m, 1 H), 4.05-3.94 (m, 1 H), 3.13-2.97 (m, 1 H), 2.52-2.40 (m, 1 H). MS m/z 386.1 (M + 1)$^+$. | 0.024 | 0.021 | >10 |

TABLE 1-continued

| Ex. No. | STRUCTURE | NMR and LC/MS | BaF3/ TRKA- NGF | Ba/ F3Tel- TrkA | BAF3/ WT |
|---|---|---|---|---|---|
| X-12 | 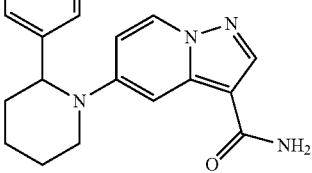 | 1H NMR (400 MHz, CDCl3) δ 8.22 (bd, J = 7.3 Hz, 1 H), 8.04 (s, 1 H), 7.39 (s, 1 H), 7.34-7.28 (m, 1 H), 7.02 (d, J = 7.7 Hz, 1 H), 6.97-6.88 (m, 2 H), 6.59 (bd, J = 5.4 Hz, 1 H), 5.07 (s, 1 H), 3.81-3.74 (m, 1 H), 3.43-3.31 (m, 1 H), 2.27-2.18 (m, 1 H), 2.15-2.02 (m, 1 H), 1.86-1.73 (m, 2 H), 1.72-1.62 (m, 1 H), 1.62-1.48 (m, 1 H). MS m/z 339.1 (M + 1)+. | 0.097 | 0.225 | >10 |
| X-13 | 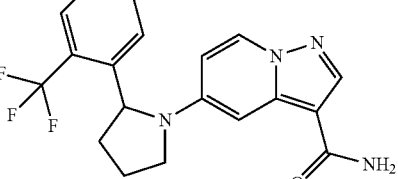 | 1H NMR (400 MHz, CDCl3) δ 8.19-8.08 (m, 1 H), 8.04 (s, 1 H), 7.76 (bd, J = 7.6 Hz, 1 H), 7.52-7.44 (m, 1 H), 7.44-7.35 (m, 1 H), 7.20 (bd, J = 7.5 Hz, 1 H), 7.09 (s, 1 H), 6.19 (bs, 1 H), 5.30 (bd, J = 7.8 Hz, 1 H), 3.97-3.82 (m, 1 H), 3.71-3.59 (m, 1 H), 2.69-2.48 (m, 1 H), 2.28-2.06 (m, 2 H), 2.06-1.88 (m, 1 H). MS m/z 375.1 (M + 1)+. | 0.341 | 0.712 | >10 |
| X-14 | 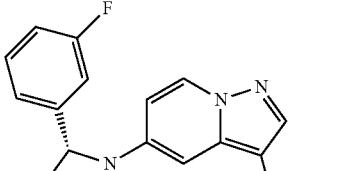 | 1H NMR (400 MHz, CDCl3) δ 8.12 (d, J = 7.6 Hz, 1 H), 7.98 (s, 1 H), 7.33 (td, J = 5.8, 7.9 Hz, 1 H), 7.24 (d, J = 2.7 Hz, 1 H), 7.06 (d, J = 7.7 Hz, 1 H), 7.02-6.88 (m, 2 H), 6.22 (dd, J = 2.7, 7.7 Hz, 1 H), 5.82-5.68 (m, 1 H), 5.40 (d, J = 52.6 Hz, 1 H), 5.12-4.99 (m, 1 H), 4.11 (ddd, J = 3.5, 12.3, 35.4 Hz, 1 H), 4.04-3.91 (m, 1 H), 3.55-3.44 (m, 2 H), 2.95-2.77 (m, 1 H), 2.28-2.00 (m, 1 H), 1.27 (t, J = 7.3 Hz, 3 H). MS m/z 371.1 (M + 1)+. | 0.008 | 0.006 | >10 |
| X-15 | 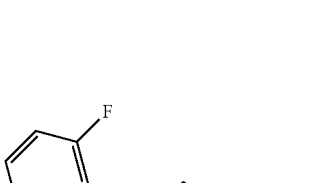 | 1H NMR (400 MHz, MeOD) δ 8.24 (d, J = 7.7 Hz, 1 H), 8.04 (s, 1 H), 7.42-7.32 (m, 1 H), 7.18 (d, J = 7.8 Hz, 1 H), 7.12-7.04 (m, 1 H), 6.99 (td, J = 2.6, 8.5 Hz, 1 H), 6.72 (d, J = 2.6 Hz, 1 H), 6.52 (dd, J = 2.7, 7.7 Hz, 1 H), 5.51-5.46 (m, 1 H), 5.08 (dd, J = 7.1, 9.2 Hz, 1 H), 4.17 (ddd, J = 3.4, 12.2, 36.4 Hz, 1 H), 3.92 (ddd, J = 1.8, 12.3, 23.7 Hz, 1 H), 3.09 (s, 6 H), 2.94-2.80 (m, 1 H), 2.26-2.06 (m, 1 H). MS m/z 371.2 (M + 1)+. | 0.043 | 0.05 | >10 |

TABLE 1-continued

| Ex. No. | STRUCTURE | NMR and LC/MS | BaF3/ TRKA-NGF | Ba/F3Tel-TrkA | BAF3/ WT |
|---|---|---|---|---|---|
| X-16 | 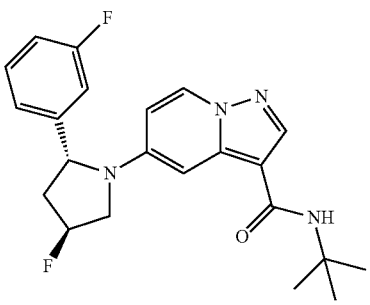 [SMILES: CC(C)(C)NC(=O)c1cnn2ccc(N3C[C@@H](F)C[C@@H]3c3cccc(F)c3)cc12] | 1H NMR (400 MHz, MeOD) δ 8.23 (s, 1 H), 8.17 (d, J = 7.7 Hz, 1 H), 7.40-7.30 (m, 1 H), 7.16 (d, J = 7.7 Hz, 1 H), 7.07 (t, J = 6.1 Hz, 2 H), 6.97 (td, J = 2.5, 8.6 Hz, 1 H), 6.42 (dd, J = 2.5, 7.7 Hz, 1 H), 5.43 (d, J = 52.9 Hz, 1 H), 5.16-5.06 (m, 1 H), 4.16 (ddd, J = 3.2, 12.3, 36.1 Hz, 1 H), 3.92 (dd, J = 12.3, 23.4 Hz, 1 H), 2.96-2.76 (m, 1 H), 2.27-2.06 (m, 1 H), 1.45 (s, 9 H). MS m/z 399.2 (M + 1)+. | 0.006 | 0.005 | >10 |
| X-17 | 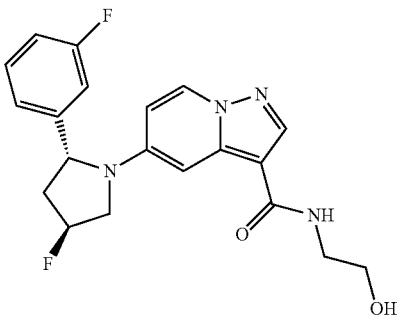 [SMILES: O=C(NCCO)c1cnn2ccc(N3C[C@@H](F)C[C@@H]3c3cccc(F)c3)cc12] | 1H NMR (400 MHz, MeOD) δ 8.26-8.11 (m, 2 H), 7.36 (dd, J = 7.7, 14.0 Hz, 1 H), 7.17 (d, J = 7.7 Hz, 1 H), 7.12-7.03 (m, 2 H), 6.98 (t, J = 8.5 Hz, 1 H), 6.47 (d, J = 7.7 Hz, 1 H), 5.43 (d, J = 52.9 Hz, 1 H), 5.10 (t, J = 8.1 Hz, 1 H), 4.26-4.07 (m, 1 H), 4.00-3.84 (m, 1 H), 3.69 (t, J = 5.9 Hz, 2 H), 3.47 (t, J = 5.8 Hz, 2 H), 2.96-2.79 (m, 1 H), 2.28-2.05 (m, 1 H). MS m/z 387.1 (M + 1)+. | 0.014 | 0.009 | >10 |
| X-18 | 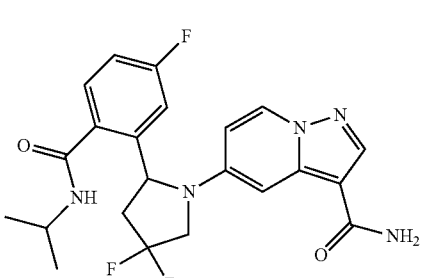 | NMR (400 MHz, MeOD) δ 8.30 (d, J = 7.7 Hz, 1 H), 8.24 (s, 1 H), 7.48 (dd, J = 5.6, 8.4 Hz, 1 H), 7.17-7.04 (m, 2 H), 6.98 (d, J = 2.6 Hz, 1 H), 6.53 (dd, J = 2.7, 7.7 Hz, 1 H), 5.29 (dd, J = 5.8, 8.5 Hz, 1 H), 4.31 (q, J = 11.8 Hz, 1 H), 4.18 (dt, J = 6.6, 13.2 Hz, 1 H), 4.02 (q, J = 12.6 Hz, 1 H), 3.19-3.02 (m, 1 H), 2.60 (tt, J = 6.8, 13.6 Hz, 1 H), 1.27 (d, J = 6.6 Hz, 3 H), 1.24 (d, J = 6.6 Hz, 3 H). MS m/z 446.2 (M + 1)+. | 0.007 | 0.007 | >10 |
| X-19 | 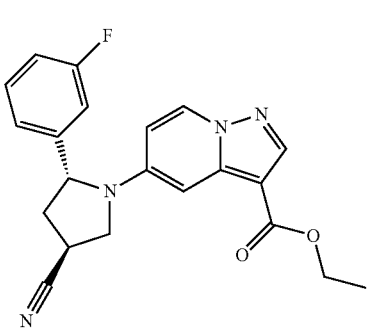 [SMILES: CCOC(=O)c1cnn2ccc(N3C[C@@H](C#N)C[C@@H]3c3cccc(F)c3)cc12] | 1H NMR (400 MHz, CDCl3) δ 8.25 (s, 1 H), 8.22 (d, J = 7.6 Hz, 1 H), 7.40-7.32 (m, 1 H), 7.07-6.96 (m, 3 H), 6.88 (d, J = 9.4 Hz, 1 H), 6.24 (dd, J = 2.7, 7.6 Hz, 1 H), 5.10 (dd, J = 2.5, 8.0 Hz, 1 H), 4.39-4.29 (m, 2 H), 4.23-4.14 (m, 1 H), 3.95-3.78 (m, 1 H), 3.42-3.29 (m, 1 H), 2.92- 2.78 (m, 1 H), 2.50-2.39 (m, 1 H), 1.36 (t, J = 7.1 Hz, 3 H). MS m/z 379.1 (M + 1)+. | 0.007 | 0.007 | >10 |

TABLE 1-continued

| Ex. No. | STRUCTURE | NMR and LC/MS | BaF3/ TRKA-NGF | Ba/ F3Tel-TrkA | BAF3/ WT |
|---|---|---|---|---|---|
| X-20 | 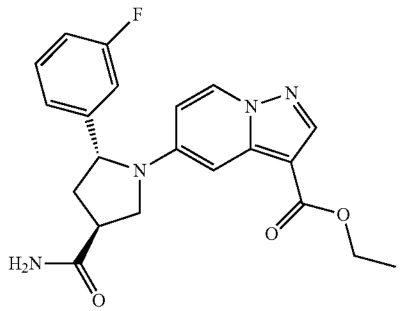 [SMILES: CCOC(=O)c1cnn2ccc(N3C[C@@H](C(N)=O)C[C@@H]3c3cccc(F)c3)cc12] | MS m/z 397.1 (M + 1)+. | 0.002 | 0.002 | >10 |
| X-21 | 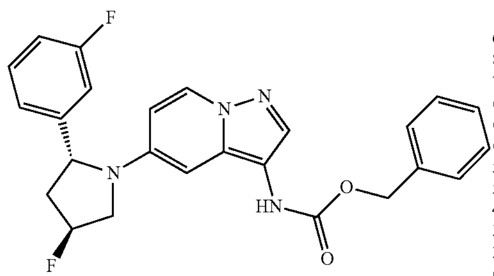 | 1H NMR (400 MHz, CDCl3) δ 8.03 (d, J = 8.2 Hz, 1 H), 7.78 (s, 1 H), 7.52-7.25 (m, 6 H), 7.01 (d, J = 7.6 Hz, 1 H), 6.98-6.84 (m, 2 H), 6.13 (d, J = 6.9 Hz, 2 H), 5.36 (d, J = 52.9 Hz, 1 H), 5.20 (s, 2 H), 5.03-4.86 (m, 1 H), 4.17-3.93 (m, 1 H), 3.93-3.72 (m, 1 H), 2.92-2.73 (m, 1 H), 2.16-1.97 (m, 1 H). MS m/z 449.1 (M + 1)+. | 0.179 | 0.177 | >10 |
| X-22 | 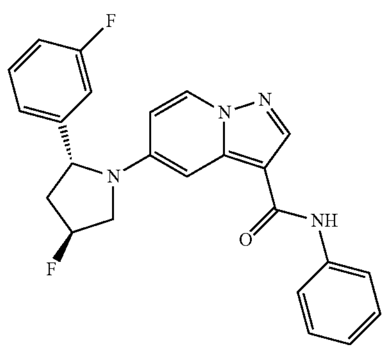 [SMILES: O=C(Nc1ccccc1)c1cnn2ccc(N3C[C@@H](F)C[C@@H]3c3cccc(F)c3)cc12] | 1H NMR (400 MHz, CDCl3) δ 8.45-8.39 (m, 1 H), 8.28-8.13 (m, 1 H), 7.69-7.57 (m, 2 H), 7.43-7.26 (m, 2 H), 7.22-7.13 (m, 2 H), 7.14-7.03 (m, 2 H), 7.02-6.92 (m, 1 H), 6.92-6.83 (m, 1 H), 6.55-6.40 (m, 1 H), 5.54-5.33 (m, 1 H), 5.16-5.07 (m, 1 H), 4.27-4.07 (m, 1 H), 4.03-3.85 (m, 1 H), 2.97-2.76 (m, 1 H), 2.31-2.06 (m, 1 H). MS m/z 419.1 (M + 1)+. | 0.017 | 0.011 | >10 |
| X-23 | 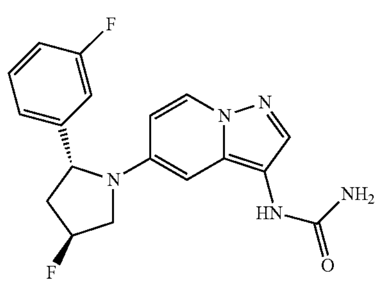 [SMILES: NC(=O)Nc1cnn2ccc(N3C[C@@H](F)C[C@@H]3c3cccc(F)c3)cc12] | 1H NMR (400 MHz, MeOD) δ 8.19-8.08 (m, 1 H), 7.83-7.67 (m, 1 H), 7.35 (dd, J = 7.8, 14.0 Hz, 1 H), 7.16 (d, J = 7.6 Hz, 1 H), 7.11-7.01 (m, 1 H), 6.97 (t, J = 8.5 Hz, 1 H), 6.44 (bd, J = 5.7 Hz, 1 H), 6.26 (bs, 1 H), 5.40 (d, J = 52.9 Hz, 1 H), 5.12-4.99 (m, 1 H), 4.16 (dd, J = 11.4, 35.7 Hz, 1 H), 3.87 (dd, J = 12.0, 23.4 Hz, 1 H), 2.93-2.77 (m, 1 H), 2.24-2.04 (m, 1 H). MS m/z 358.1 (M + 1)+. | 0.176 | 0.154 | >10 |

TABLE 1-continued

| Ex. No. | STRUCTURE | NMR and LC/MS | BaF3/ TRKA-NGF | Ba/ F3Tel-TrkA | BAF3/ WT |
|---|---|---|---|---|---|
| X-24 | 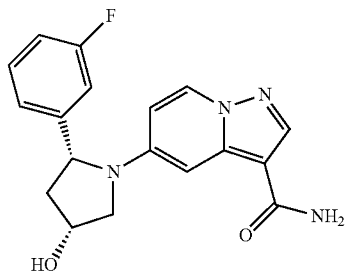 [SMILES: NC(=O)c1cnn2ccc(N3C[C@H](O)C[C@@H]3c3cccc(F)c3)cc12] | 1H NMR (400 MHz, CD3CN) δ 8.18 (d, J = 7.4 Hz, 1 H), 8.02 (s, 1 H), 7.39-7.27 (m, 1 H), 7.18 (d, J = 7.8 Hz, 1 H), 7.12-7.04 (m, 1 H), 7.00-6.89 (m, 2 H), 6.39 (dd, J = 2.8, 7.7 Hz, 1 H), 5.78 (bs, 1 H), 4.92 (d, J = 5.8 Hz, 1 H), 4.60-4.46 (m, 1 H), 3.78-3.67 (m, J = 3.7 Hz, 2 H), 3.11-3.07 (m, J = 3.0 Hz, 1 H), 2.75-2.63 (m, 1 H). MS m/z 341.1 (M + 1)+. | 0.119 | 0.395 | >10 |
| X-25 | 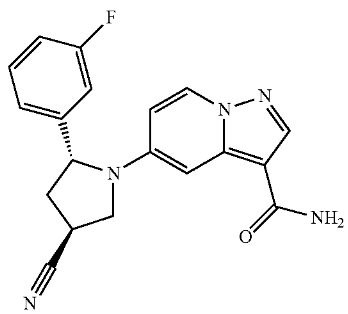 [SMILES: N#C[C@H]1C[C@H](c2cccc(F)c2)N(c2ccn3ncc(C(N)=O)c3c2)C1] | 1H NMR (400 MHz, CD3CN) δ 8.22 (d, J = 7.8 Hz, 1 H), 8.05 (s, 1 H), 7.43-7.28 (m, 1 H), 7.10 (d, J = 7.7 Hz, 1 H), 7.06-6.96 (m, 3 H), 6.38 (dd, J = 2.8, 7.7 Hz, 1 H), 5.09 (dd, J = 3.0, 8.1 Hz, 1 H), 4.18 (dd, J = 7.6, 9.6 Hz, 1 H), 3.82-3.70 (m, 1 H), 3.49-3.34 (m, 1 H), 2.86-2.68 (m, 1 H), 2.38-2.28 (m, 1 H). MS m/z 350.1 (M + 1)+. | 0.058 | 0.125 | >10 |
| X-26 | 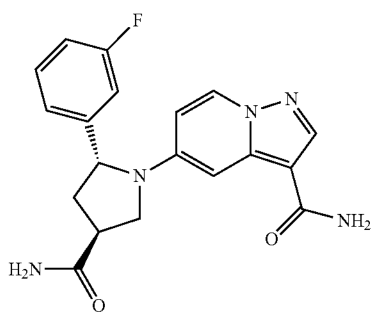 [SMILES: NC(=O)c1cnn2ccc(N3C[C@@H](C(N)=O)C[C@@H]3c3cccc(F)c3)cc12] | 1H NMR (400 MHz, DMSO) δ 8.38 (d, J = 7.7 Hz, 1 H), 8.26 (s, 1 H), 7.53 (s, 1 H), 7.44-7.31 (m, 1 H), 7.15-7.01 (m, 2 H), 6.96 (s, 1 H), 6.31 (d, J = 7.1 Hz, 1 H), 5.13 (d, J = 8.0 Hz, 1 H), 3.98-3.85 (m, 1 H), 3.65-3.54 (m, 1 H), 3.20-3.07 (m, 1 H), 2.60-2.52 (m, 1 H), 2.08 (dd, J = 6.9, 12.0 Hz, 1 H). MS m/z 368.1 (M + 1)+. | 0.232 | 0.443 | >10 |
| X-27 | 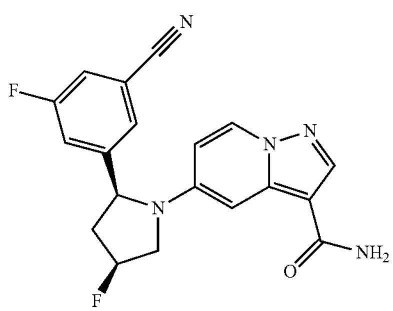 [SMILES: N#Cc1cc(F)cc([C@@H]2C[C@H](F)CN2c2ccn3ncc(C(N)=O)c3c2)c1] | MS m/z 368.1 (M + 1)+. | >10 | >10 | >10 |
| X-28 | 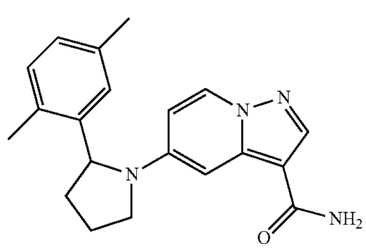 [SMILES: Cc1ccc(C)c(C2CCCN2c2ccn3ncc(C(N)=O)c3c2)c1] | MS m/z 335.1 (M + 1)+. | 1.092 | 2.142 | >10 |

TABLE 1-continued

| Ex. No. | STRUCTURE | NMR and LC/MS | BaF3/ TRKA-NGF | Ba/ F3Tel-TrkA | BAF3/ WT |
|---|---|---|---|---|---|
| X-29 | 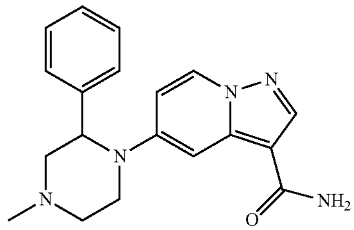 [SMILES: CN1CCN(c2ccn3ncc(C(N)=O)c3c2)C(c2ccccc2)C1] | MS m/z 336.1 (M + 1)+. | >10 | >10 | >10 |

Assays

Preparation of Compound Dilutions

Test compounds were dissolved in DMSO (10 mM) and transferred into 1.4 mL flat bottom or V-shaped Matrix tubes carrying a unique 2D matrix chip by individual compound hubs. The numbers of these chips were distinctively linked to the individual compound identification numbers. The stock solutions were stored at −20° C. if not used immediately. For the test procedure the vials were defrosted and identified by a scanner whereby a working sheet is generated that guides the subsequent working steps.

Compound dilutions were made in 384 well plates. This format enabled the assay of maximally 28 individual test compounds at 11 concentrations (single points) including 2 reference compounds. The dilution protocol included the production of pre-dilution plates, master plates and assay plates:

Compound plates: 30 μL of individual compound (10 mM) DMSO solution including reference compound were transferred into columns 1 and 13 of a 384 well plate. 20 μL of DMSO were added to the rest of the wells and the compounds were serially diluted (1:3) by transferring 10 μL from a well in column 1 or 13 to the next well in column 2 or 14 respectively and successively with the help of a Minitrack robot.

Assay plates: Identical assay plates were then prepared by adding 50 nL each of compound dilutions of the compound plates into 384-well "assay plates". In the following the compounds were mixed with 50 μL of assays components (cells or enzyme) and tested for their inhibitory activity.

Compounds of Formula (I) were assayed to measure their capacity to inhibit TrkA, TrkB, and/or TrkC protein kinases. Other compounds of Formula (I) were assayed to measure their capacity to inhibit a Ba/F3 kinase panel, including but not limited to Ros, KDR, FMS, c-FMS, FLT3, c-Kit, JAK2, PDGFR, Lck, TrkA, TrkB, TrkC, IGF-1R and ALK protein kinases.

Ba/F3 Cell Proliferation Assay Panel

Compounds were tested for their ability to inhibit the proliferation of wt Ba/F3 cells and Ba/F3 cells transformed with constitutively expressed luciferase reporter and BCR-ABL or Tel-FMS or other Tel fusion kinases (EGFR, JAK2, ALK, BMX, FGFR3, FGFR4, FGR2, FLT1, FLT3, IGF1R, INSR, KDR, KIT, LCK, LYN, MEK, MET, PDGFRα, PDGFRβ, RET, RON, ROS, SRC, SYK, TIE and TYRO) or BRafV600E. Parental Ba/F3 cells were maintained in media containing recombinant mouse IL3 and the kinase transformed Ba/F3 cells were maintained in media without IL-3. 7.5 nl of compounds were spotted to each well of 1536-well assay plates by Liquid handling System Echo 555 (Labcyte). 700 cells were then plated into each well of the assay plates in 7 uL culture media per well and compounds were tested at 0.17 nM to 10 uM in 3-fold serial dilutions. The cells were then incubated for 48 hours at 37° C. 3 uL of Bright-Glo® (Promega) was added to each well and the plates were read using ViewLux (PerkinElmer).

Inhibition of Cellular TrkA, TrkB and TrkC Dependent Proliferation

Compounds of Formula (I) were assayed to measure their capacity to selectively inhibit cell proliferation of Ba/F3 cells expressing activated TrkA, TrkB or TrkC through fusion to the dimerization domain of Tel (ETV6) transcription factor as well as Ba/F3 cells co-expressing full length rTrkA and mNGF compared with parental BaF3 cells.

The cell line used is the luciferase expressing Ba/F3 murine hematopoietic progenitor cell line transformed with human Tel-TrkA, Tel-TrkB or Tel-TrkC cDNAs (Ba/F3 EN A/B/C). These cells maintained in RPMI/10% fetal bovine serum (RPMI/FCS) supplemented with penicillin 50 mg/mL, streptomycin 50 mg/mL and L-glutamine 200 mM. Untransformed Ba/F3 cells were similarly maintained with the addition 5 ng/ml of murine recombinant IL3. 50 μl of a Ba/F3 or Ba/F3 EN A/B/C cell suspension were plated in Greiner 384 well microplates (white)) at a density of 2000 cells per well. 50 nl of serially diluted test compound (10-0.0001 mM in DMSO solution) is added to each well. The cells were incubated for 48 hours at 37° C., 5% $CO_2$. 25 μl of Bright Glo® (Promega) luciferase substrate is added to each well. The emited luminiscence is quantified using ViewLux (PerkinElmer). $IC_{50}$ values were calculated by linear regression analysis of the percentage inhibition of each compound at 11 concentrations.

Certain Assay Results

Various compounds of Formula (I) in free form or in pharmaceutically acceptable salt form, exhibit pharmacological properties, for example, as indicated by the in vitro and in vivo tests described in this application. The $IC_{50}$ value in those experiments is given as that concentration of the test compound in question that results in a cell count that is 50% lower than that obtained using the control without inhibitor. In certain examples compounds of Formula (I) have $IC_{50}$ values from 0.1 nM 1 μM. In other examples, compounds of Formula (I) have $IC_{50}$ values from 0.0001 μM to 0.8 μM. In other examples, compounds of Formula (I) have $IC_{50}$ values from 0.0001 μM to 0.6 μM. In other examples, compounds of Formula (I) have $IC_{50}$ values from 0.0001 μM to 0.4 μM. In other examples, compounds of Formula (I) have $IC_{50}$ values from 0.0001 μM to 0.2 μM. In other examples, compounds of Formula (I) have $IC_{50}$ values from 0.0001 μM to 0.1 μM. In other examples, compounds of Formula (I) have $IC_{50}$ values from 0.0001 μM to 0.08 μM. In other examples, compounds of Formula (I) have $IC_{50}$ values from 0.0001 μM to 0.06 μM.

In other examples, compounds of Formula (I) have IC$_{50}$ values from 0.0001 μM to 0.04 μM. In other examples, compounds of Formula (I) have IC$_{50}$ values from 0.0001 μM to 0.02 μM. In other examples, compounds of Formula (I) have IC$_{50}$ values from 0.0001 μM to 0.01 μM. In other examples, compounds of Formula (I) have IC$_{50}$ values from 0.01 μM to 1 μM. In yet other examples, compounds of Formula (I) have IC$_{50}$ values of less than 1 nM. In certain embodiments, compounds of Formula (I) exhibit a percentage inhibition of greater than 50%, or in other embodiments compounds of Formula (I) exhibit a percentage inhibition greater than about 70%.

Embodiments

The following are further embodiments of the invention:

Embodiment 1: A compound of Formula (I):

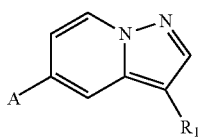

Formula (I)

wherein:
A is

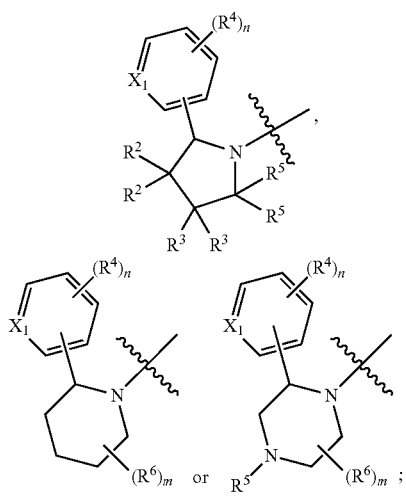

X$_1$ is CH or N;
R$^1$ is —C(O)NH$_2$, —C(O)N(R$^7$)$_2$, —C(O)N(R$^8$)$_2$, —NR$^7$C(O)R$^8$, —NR$^7$C(O)N(R$^7$)$_2$, —NR$^7$C(O)N(R$^8$)$_2$, —NR$^7$C(O)N(R$^9$)$_2$; —C(O)OR$^7$, —NR$^7$C(O)OR$^7$, —NR$^7$C(O)OR$^8$, —C(O)NR$^7$R$^8$, —C(O)NR$^7$C(O)OR$^7$, —C(O)NR$^7$C(O)NH$_2$, —C(O)NR$^7$C(O)N(R$^7$)$_2$ or H;
each R$^2$ is independently selected from H and C$_1$-C$_6$alkyl;
each R$^3$ is independently selected from H, C$_1$-C$_6$alkyl, —CN, —C(O)N(R$^7$)$_2$, —OR$^7$ and halo, or the two R$^3$ together with the C atom they are attached form a cyclopropyl group spiro attached to the pyrrolidine;
or a R$^2$ and a R$^3$ together with the C atom they are attached form a cyclopropyl ring fused to the pyrrolidine;
each R$^4$ is independently selected from H, halo, —OR$^7$, C$_1$-C$_6$alkyl, C$_1$-C$_6$alkyl substituted with 1-3 halo, C$_1$-C$_6$alkoxy substituted with 1-3 halo, —CN and —C(O)N(R$^7$)$_2$;
each R$^5$ is independently selected from H and C$_1$-C$_6$alkyl;
each R$^6$ is independently selected from H, C$_1$-C$_6$alkyl, —CN, —OR$^7$ and halo;
each R$^7$ is independently selected from H, C$_1$-C$_6$alkyl or C$_1$-C$_6$alkyl substituted with 1-3 —OH;
each R$^8$ is independently selected from H, C$_1$-C$_6$alkyl, phenyl, benzyl, phenyl substituted with 1-3 groups independently selected from R$^6$, benzyl substituted with 1-3 groups independently selected from R$^6$, an unsubstituted 5-6 membered heterocycloalkyl having 1 to 2 heteroatoms independently selected from O and N, a 5-6 membered heterocycloalkyl having 1 to 2 heteroatoms independently selected from O and N which is substituted with 1-3 groups independently selected from R$^6$, an unsubstituted C$_3$-C$_6$cycloalkyl, a C$_3$-C$_6$cycloalkyl substituted with 1-3 groups independently selected from R$^6$, an unsubstituted 5-6 membered heteroaryl having 1 to 2 heteroatoms independently selected from O and N, a 5-6 membered heteroaryl having 1 to 2 heteroatoms independently selected from O and N which is substituted with 1-3 groups independently selected from R$^6$;
each R$^9$ is a C$_1$-C$_6$alkyl and together with the N atom they are attached form an unsubstituted 5-6 membered heterocycloalkyl or a 5-6 membered heterocycloalkyl substituted with 1-3 groups independently selected from R$^6$;
m is 0, 1, 2, 3 or 4,
n is 0, 1 or 2,
or a pharmaceutically acceptable salt thereof.

Embodiment 2: A compound of Formula (I):

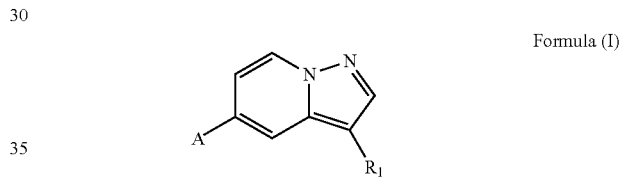

Formula (I)

wherein:
A is

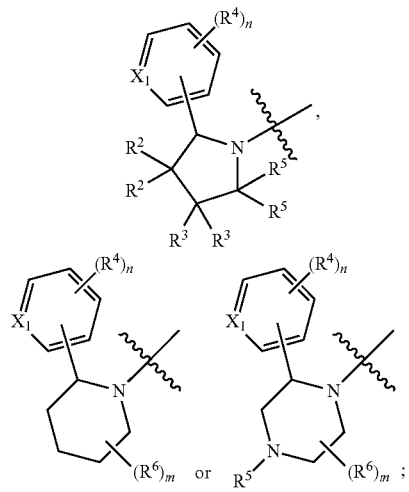

X$_1$ is CH or N;
R$^1$ is —C(O)NH$_2$, —C(O)N(R$^7$)$_2$, —C(O)N(R$^8$)$_2$, —NR$^7$C(O)R$^8$, —NR$^7$C(O)N(R$^7$)$_2$, —NR$^7$C(O)N(R$^8$)$_2$, —NR$^7$C(O)N(R$^9$)$_2$; —C(O)OR$^7$—, —NR$^7$C(O)OR$^7$, —C(O)NR$^7$C(O)OR$^7$, —C(O)NR$^7$C(O)NH$_2$, —C(O)NR$^7$C(O)N(R$^7$)$_2$ or H;

each $R^2$ is independently selected from H and $C_1$-$C_6$alkyl;

each $R^3$ is independently selected from H, $C_1$-$C_6$alkyl, —CN, —$OR^7$ and halo, or the two $R^3$ together with the C atom they are attached form a cyclopropyl group spiro attached to the pyrrolidine;

or a $R^2$ and a $R^3$ together with the C atom they are attached form a cyclopropyl ring fused to the pyrrolidine;

each $R^4$ is independently selected from H, halo, —$OR^7$, $C_1$-$C_6$alkyl, $C_1$-$C_6$alkyl substituted with 1-3 halo, $C_1$-$C_6$alkoxy substituted with 1-3 halo, —CN and —C(O)N($R^7$)$_2$;

each $R^5$ is independently selected from H and $C_1$-$C_6$alkyl;

each $R^6$ is independently selected from H, $C_1$-$C_6$alkyl, —CN, —$OR^7$ and halo;

each $R^7$ is independently selected from H, $C_1$-$C_6$alkyl or $C_1$-$C_6$alkyl substituted with 1-3 —OH;

each $R^8$ is independently selected from H, $C_1$-$C_6$alkyl, phenyl, phenyl substituted with 1-3 groups independently selected from $R^6$, an unsubstituted 5-6 membered heterocycloalkyl having 1 to 2 heteroatoms independently selected from O and N, a 5-6 membered heterocycloalkyl having 1 to 2 heteroatoms independently selected from O and N which is substituted with 1-3 groups independently selected from $R^6$, an unsubstituted $C_3$-$C_6$cycloalkyl, a $C_3$-$C_6$cycloalkyl substituted with 1-3 groups independently selected from $R^6$, an unsubstituted 5-6 membered heteroaryl having 1 to 2 heteroatoms independently selected from O and N, a 5-6 membered heteroaryl having 1 to 2 heteroatoms independently selected from O and N which is substituted with 1-3 groups independently selected from $R^6$;

each $R^9$ is a $C_1$-$C_6$alkyl and together with the N atom they are attached form an unsubstituted 5-6 membered heterocycloalkyl or a 5-6 membered heterocycloalkyl substituted with 1-3 groups independently selected from $R^6$;

m is 0, 1, 2, 3 or 4, n is 0, 1 or 2, or a pharmaceutically acceptable salt thereof.

Embodiment 3: The compound according to embodiment 1, wherein the compound of Formula (I) is a compound having the structure of Formula (II):

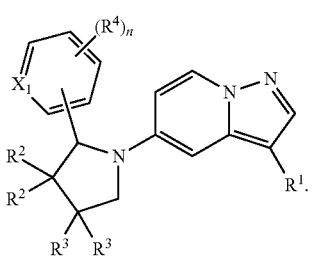

Formula (II)

Embodiment 4: The compound according to embodiment 2, wherein the compound of Formula (II) is a compound having the structure of Formula (II-a) or Formula (II-b):

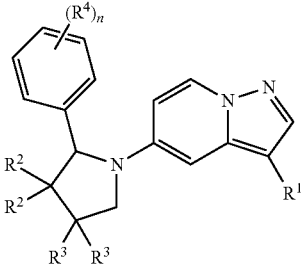

Formula (II-a)

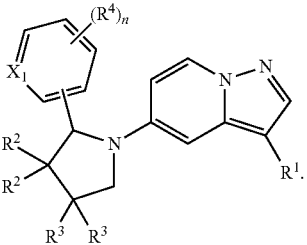

Formula (II-b)

Embodiment 5: The compound of embodiment 2 or embodiment 3, wherein the compound of Formula (II) or Formula (II-a) is a compound having the structure of Formula (II-c):

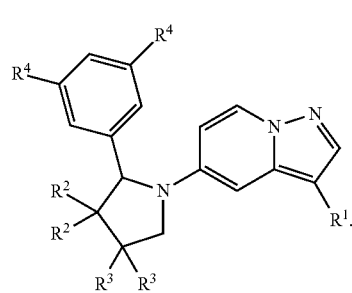

Formula (II-c)

Embodiment 6: The compound of any one of embodiments 1 to 4, wherein each $R^7$ is independently selected from H, methyl and ethyl.

Embodiment 7: The compound of any one of embodiments 1 to 5, wherein each $R^4$ is independently selected from H, F, —CN, —C(O)NH$_2$—OCF$_3$, —OCHF$_2$ and —OCH$_2$F.

Embodiment 8: The compound of any one of the embodiments 1 to 7, wherein each $R^3$ is independently selected from H, —CN, —C(O)NH$_2$ and F, and wherein each $R^2$ is H.

Embodiment 9: The compound of any one of embodiments 1 to 6, wherein each $R^3$ is independently selected from H and F, and wherein each $R^2$ is H.

Embodiment 10: The compound of any one of the embodiments 1 to 9, wherein $R^1$ is —C(O)NH$_2$, —C(O)N($R^7$)$_2$ or —C(O)OR$^7$.

Embodiment 11: The compound of any one of embodiments 1 to 7, wherein each $R^1$ is —C(O)NH$_2$.

Embodiment 12: The compound of embodiments 1 or 2 selected from: 5-((2R,4S)-2-(3-cyano-5-fluorophenyl)-4-fluoropyrrolidin-1-yl)pyrazolo[1,5-a]pyridine-3-carboxamide; ethyl 5-((2R,4S)-4-fluoro-2-(3-fluorophenyl)pyrrolidin-1-yl)pyrazolo[1,5-a]pyridine-3-carboxylate; (R)-ethyl 5-(4,4-difluoro-2-(3-fluorophenyl)pyrrolidin-1-yl)pyrazolo[1,5-a]pyridine-3-carboxylate; 5-((2R,4S)-4- fluoro-2-(3-fluorophenyl)pyrrolidin-1-yl)pyrazolo[1,5-a]pyridine-3-carboxylic acid; (R)-5-(4,4-difluoro-2-(3-fluorophenyl)pyrrolidin-1-yl)pyrazolo[1,5-a]pyridine-3-carboxylic acid; 5-((2R,4S)-4-fluoro-2-(3-fluorophenyl)pyrrolidin-1-yl)pyrazolo[1,5-a]pyridine-3-carboxamide; (R)-5-(4,4-difluoro-2-(3-fluorophenyl)pyrrolidin-1-yl)pyrazolo[1,5-a]pyridine-3-carboxamide; ethyl 5-((2R,4S)-2-(3-cyano-5-fluorophenyl)-4-fluoropyrrolidin-1-yl)pyrazolo[1,5-a]pyridine-3-carboxylate; (R)-ethyl 5-(2-(3-cyano-5-fluorophenyl)-4,4-difluoropyrrolidin-1-yl)pyrazolo[1,5-a]pyridine-3-carboxylate; (R)-5-(2-(3-carbamoyl-5-fluorophenyl)-4,4-difluoropyrrolidin-1-yl)pyrazolo[1,5-a]pyridine-3-carboxamide; (R)-5-(2-(3-cyano-5-fluorophenyl)-4,4-difluoropyrrolidin-1-yl)pyrazolo[1,5-a]pyridine-3-carboxamide; ethyl 5-(4-fluoro-2-(3-fluorophenyl)pyrrolidin-1-yl)pyrazolo[1,5-a]pyridine-3-carboxylate; ethyl 5-(4,4-difluoro-2-(3-fluorophenyl)pyrrolidin-1-yl)pyrazolo[1,5-a]pyridine-3-carboxylate; 5-(4-fluoro-2-(3-fluorophenyl)pyrrolidin-1-yl)pyrazolo[1,5-a]pyridine-3-carboxylic acid; 5-(4,4-difluoro-2-(3-fluorophenyl)pyrrolidin-1-yl)pyrazolo[1,5-a]pyridine-3-carboxylic acid; 5-(4-fluoro-2-(3-fluorophenyl)pyrrolidin-1-yl)pyrazolo[1,5-a]pyridine-3-carboxamide; 5-(4,4-difluoro-2-(3-fluorophenyl)pyrrolidin-1-yl)pyrazolo[1,5-a]pyridine-3-carboxamide; ethyl 5-(2-(3-cyano-5-fluorophenyl)-4-fluoropyrrolidin-1-yl)pyrazolo[1,5-a]pyridine-3-carboxylate; ethyl 5-(2-(3-cyano-5-fluorophenyl)-4,4-difluoropyrrolidin-1-yl)pyrazolo[1,5-a]pyridine-3-carboxylate; 5-(2-(3-carbamoyl-5-fluorophenyl)-4,4-difluoropyrrolidin-1-yl)pyrazolo[1,5-a]pyridine-3-carboxamide; 5-(2-(3-cyano-5-fluorophenyl)-4-fluoropyrrolidin-1-yl)pyrazolo[1,5-a]pyridine-3-carboxamide, and 5-(2-(3-cyano-5-fluorophenyl)-4,4-difluoropyrrolidin-1-yl)pyrazolo[1,5-a]pyridine-3-carboxamide.

Embodiment 13: The compound of embodiment 1 selected from: 5-[2-(3-fluorophenyl)piperidin-1-yl]pyrazolo[1,5-a]pyridine-3-carboxamide; 5-{2-[2-(trifluoromethyl)phenyl]pyrrolidin-1-yl}pyrazolo[1,5-a]pyridine-3-carboxamide; N-ethyl-5-[(2R,4S)-4-fluoro-2-(3-fluorophenyl)pyrrolidin-1-yl]pyrazolo[1,5-a]pyridine-3-carboxamide; 5-[(2R,4S)-4-fluoro-2-(3-fluorophenyl)pyrrolidin-1-yl]-N,N-dimethylpyrazolo[1,5-a]pyridine-3-carboxamide; N-tert-butyl-5-[(2R,4S)-4-fluoro-2-(3-fluorophenyl)pyrrolidin-1-yl]pyrazolo[1,5-a]pyridine-3-carboxamide; 5-[(2R,4S)-4-fluoro-2-(3-fluorophenyl)pyrrolidin-1-yl]-N-(2-hydroxyethyl)pyrazolo[1,5-a]pyridine-3-carboxamide; 5-(4,4-difluoro-2-{5-fluoro-2-[(propan-2-yl)carbamoyl]phenyl}pyrrolidin-1-yl)pyrazolo[1,5-a]pyridine-3-carboxamide; ethyl 5-[(2R,4S)-4-cyano-2-(3-fluorophenyl)pyrrolidin-1-yl]pyrazolo[1,5-a]pyridine-3-carboxylate; ethyl 5-[(2R,4S)-4-carbamoyl-2-(3-fluorophenyl)pyrrolidin-1-yl]pyrazolo[1,5-a]pyridine-3-carboxylate; benzyl N-{5-[(2R,4S)-4-fluoro-2-(3-fluorophenyl)pyrrolidin-1-yl]pyrazolo[1,5-a]pyridin-3-yl}carbamate; 5-[(2R,4S)-4-fluoro-2-(3-fluorophenyl)pyrrolidin-1-yl]-N-phenylpyrazolo[1,5-a]pyridine-3-carboxamide; {5-[(2R,4S)-4-fluoro-2-(3-fluorophenyl)pyrrolidin-1-yl]pyrazolo[1,5-a]pyridin-3-yl}urea; 5-[(2R,4R)-2-(3-fluorophenyl)-4-hydroxypyrrolidin-1-yl]pyrazolo[1,5-a]pyridine-3-carboxamide; 5-[(2R,4S)-4-cyano-2-(3-fluorophenyl)pyrrolidin-1-yl]pyrazolo[1,5-a]pyridine-3-carboxamide, and (3S,5R)-1-{3-carbamoylpyrazolo[1,5-a]pyridin-5-yl}-5-(3-fluorophenyl)pyrrolidine-3-carboxamide.

Embodiment 14: The compound of embodiment 1 selected from: 5-((2R,4S)-2-(3-cyano-5-fluorophenyl)-4-fluoropyrrolidin-1-yl)pyrazolo[1,5-a]pyridine-3-carboxamide.

Embodiment 15: The compound of embodiment 1 selected from: N-ethyl-5-[(2R,4S)-4-fluoro-2-(3-fluorophenyl)pyrrolidin-1-yl]pyrazolo[1,5-a]pyridine-3-carboxamide.

Embodiment 16: The compound of embodiment 1 selected from: ethyl 5-[(2R,4S)-4-cyano-2-(3-fluorophenyl)pyrrolidin-1-yl]pyrazolo[1,5-a]pyridine-3-carboxylate.

Embodiment 17: The compound of embodiment 1 selected from: ethyl 5-[(2R,4S)-4-carbamoyl-2-(3-fluorophenyl)pyrrolidin-1-yl]pyrazolo[1,5-a]pyridine-3-carboxylate.

Embodiment 18: A pharmaceutical composition comprising a therapeutically effective amount of a compound of any one of embodiments 1-17 and a pharmaceutically acceptable carrier.

Embodiment 19: A pharmaceutical composition comprising a therapeutically effective amount of a compound of embodiments 12 and a pharmaceutically acceptable carrier.

Embodiment 20: Use of a compound of any one of embodiments 1-17 in the manufacture of a medicament for treating a TRK kinase-mediated disease or condition, wherein the disease or condition is papillary thyroid carcinoma, pancreatic cancer, colon cancer, breast carcinoma, neuroblastoma, pain, cachexia, dermatitis or asthma.

Embodiment 21: A method for inhibiting a TRK kinase comprising administering to a system or a subject in need thereof, a therapeutically effective amount of a compound any one of embodiments 1-17, or pharmaceutically acceptable salts or pharmaceutical compositions thereof.

Embodiment 22: A method for treating a TRK kinase-mediated disease or condition, comprising administering to a system or subject in need of such treatment an effective amount of a compound of any one of embodiments 1-17, or pharmaceutically acceptable salts or pharmaceutical compositions thereof, wherein the disease or condition is papillary thyroid carcinoma, pancreatic cancer, colon cancer, breast carcinoma, neuroblastoma, pain, cachexia, dermatitis or asthma.

Embodiment 23: A compound of any one of embodiments 1-17 for use in a the treatment of a disease wherein TRK kinase activity is implicated, wherein the disease is selected from papillary thyroid carcinoma, pancreatic cancer, colon cancer, breast carcinoma, neuroblastoma, pain, cachexia, dermatitis and asthma.

Embodiment 24: A combination comprising a therapeutically effective amount of the compound according to any one of embodiments 1 to 17 and one or more therapeutically active co-agents.

Embodiment 25: A combination of embodiment 24, wherein the combination is a pharmaceutical combination.

Embodiment 26: A combination of embodiment 24, wherein the co-agent is selected from a chemotherapeutic agent, an anti-inflammatory agent, a bronchodilatory agent, and an antiproliferative agents.

Embodiment 27: A combination comprising a therapeutically effective amount of the compound according to any one of embodiments 1 to 17 and one or more additional therapeutic agents.

Embodiment 28: A combination of embodiment 27, wherein the combination is a pharmaceutical combination.

Embodiment 29: A combination of embodiment 27, wherein the additional thereapeutic agent is selected from a chemotherapeutic agent, an anti-inflammatory agent, a bronchodilatory agent, and an antiproliferative agents.

Embodiment 30: Compounds of Formula (A), or pharmaceutically acceptable salt thereof:

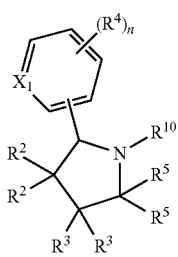

(Formula A)

wherein:
X₁ is CH or N;
each R² is independently selected from H and C₁-C₆alkyl;
each R³ is independently selected from H, C₁-C₆alkyl, —CN, —C(O)N(R⁷)₂, —OR⁷ and halo, or the two R³ together with the C atom they are attached form a cyclopropyl group spiro attached to the pyrrolidine;
or a R² and a R³ together with the C atom they are attached form a cyclopropyl ring fused to the pyrrolidine;
each R⁴ is independently selected from H, halo, —OR⁷, C₁-C₆alkyl, C₁-C₆alkyl substituted with 1-3 halo, C₁-C₆alkoxy substituted with 1-3 halo, —CN and —C(O)N(R⁷)₂;
each R⁵ is independently selected from H;
R¹⁰ is H or an amine protecting group, and
n is 0, 1 or 2.

Embodiment 31: Compounds of Formula (A) of embodiment 30, wherein the compound of Formula (A) are a compounds of Formula (B),

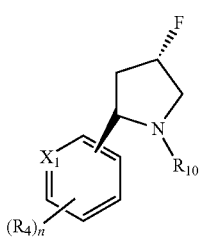

Formula (B)

wherein:
X₁ is CH or N;
each R⁴ is independently selected from H, halo, —OR⁷, C₁-C₆alkyl, C₁-C₆alkyl substituted with 1-3 halo, C₁-C₆alkoxy substituted with 1-3 halo, —CN and —C(O)N(R⁷)₂;
R¹⁰ is H or an amine protecting group, and
n is 0, 1 or 2.

Embodiment 32: Compounds of Formula (B) of embodiment 31, wherein the compound of Formula (B) is

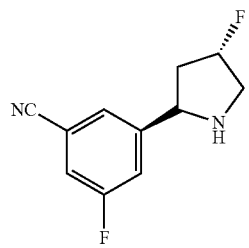

Embodiment 32: Compounds of Formula (II), or pharmaceutically acceptable salt thereof:

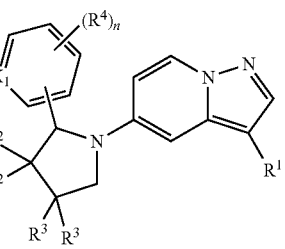

Formula (II)

prepared by a process comprising coupling in the presence of a catalyst an amine of Formula A

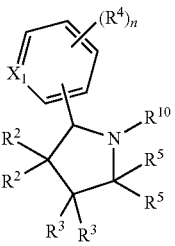

(Formula A)

with a compound of Formula C

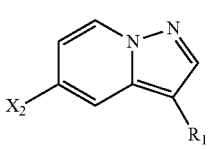

(Formula C)

wherein:
X₁ is CH or N;
X₂ is I, Br or Cl;
R¹ is —C(O)NH₂, —C(O)N(R⁷)₂, —C(O)N(R⁸)₂, —NR⁷C(O)R⁸, —NR⁷C(O)N(R⁷)₂, —NR⁷C(O)N(R⁸)₂, —NR⁷C(O)N(R⁹)₂; —C(O)OR⁷, —NR⁷C(O)OR⁷, —NR⁷C(O)OR⁸, —C(O)NR⁷R⁸, —C(O)NR⁷C(O)OR⁷, —C(O)NR⁷C(O)NH₂, —C(O)NR⁷C(O)N(R⁷)₂ or H;
each R² is independently selected from H and C₁-C₆alkyl;
each R³ is independently selected from H, C₁-C₆alkyl, —CN, —C(O)N(R⁷)₂, —OR⁷ and halo, or the two R³ together with the C atom they are attached form a cyclopropyl group spiro attached to the pyrrolidine;

or a $R^2$ and a $R^3$ together with the C atom they are attached form a cyclopropyl ring fused to the pyrrolidine;

each $R^4$ is independently selected from H, halo, —$OR^7$, $C_1$-$C_6$alkyl, $C_1$-$C_6$alkyl substituted with 1-3 halo, $C_1$-$C_6$alkoxy substituted with 1-3 halo, —CN and —C(O)N($R^7$)$_2$;

each $R^5$ is independently selected from H;

each $R^6$ is independently selected from H, $C_1$-$C_6$alkyl, —CN, —$OR^7$ and halo;

each $R^7$ is independently selected from H, $C_1$-$C_6$alkyl or $C_1$-$C_6$alkyl substituted with 1-3 —OH;

each $R^8$ is independently selected from H, $C_1$-$C_6$alkyl, phenyl, benzyl, phenyl substituted with 1-3 groups independently selected from $R^6$, benzyl substituted with 1-3 groups independently selected from $R^6$, an unsubstituted 5-6 membered heterocycloalkyl having 1 to 2 heteroatoms independently selected from O and N, a 5-6 membered heterocycloalkyl having 1 to 2 heteroatoms independently selected from O and N which is substituted with 1-3 groups independently selected from $R^6$, an unsubstituted $C_3$-$C_6$cycloalkyl, a $C_3$-$C_6$cycloalkyl substituted with 1-3 groups independently selected from $R^6$, an unsubstituted 5-6 membered heteroaryl having 1 to 2 heteroatoms independently selected from O and N, a 5-6 membered heteroaryl having 1 to 2 heteroatoms independently selected from O and N which is substituted with 1-3 groups independently selected from $R^6$;

each $R^9$ is a $C_1$-$C_6$alkyl and together with the N atom they are attached form an unsubstituted 5-6 membered heterocycloalkyl or a 5-6 membered heterocycloalkyl substituted with 1-3 groups independently selected from $R^6$;

$R^{10}$ is H, and m is 0, 1, 2, 3 or 4, and n is 0, 1 or 2.

Embodiment 34: Such compounds of Formula (II) of embodiment 33, the amine of Formula (A) is a compound of Formula (B),

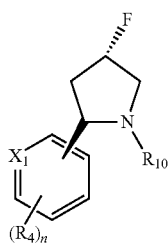

Formula (B)

wherein:

$X_1$ is CH or N;

each $R^4$ is independently selected from H, halo, —$OR^7$, $C_1$-$C_6$alkyl, $C_1$-$C_6$alkyl substituted with 1-3 halo, $C_1$-$C_6$alkoxy substituted with 1-3 halo, —CN and —C(O)N($R^7$)$_2$;

$R^{10}$ is H, and n is 0, 1 or 2.

Embodiment 35: Such compounds of Formula (B) of embodiment 34, wherein the compound of Formula (B) is

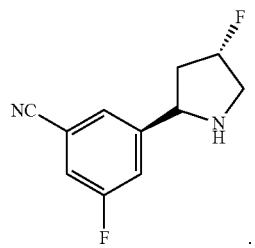

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula (I):

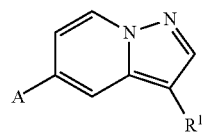

Formula (I)

wherein:

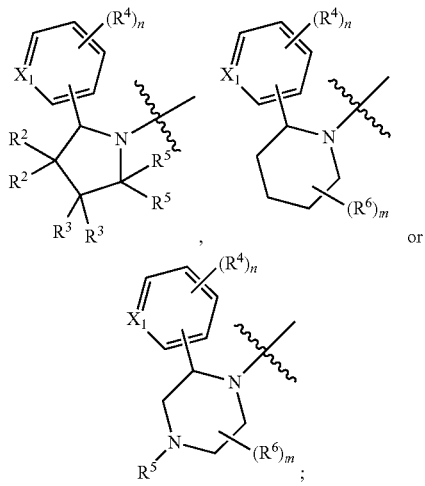

A is $X_1$ is CH or N;

$R^1$ is —C(O)NH$_2$, —C(O)N($R^7$)$_2$, —C(O)N($R^8$)$_2$, —N$R^7$C(O)$R^8$, —N$R^7$C(O)N($R^7$)$_2$, —N$R^7$C(O)N($R^8$)$_2$, —N$R^7$C(O)N($R^9$)$_2$; —C(O)O$R^7$, —N$R^7$C(O)O$R^7$, —N$R^7$C(O)O$R^8$, —C(O)N$R^7$$R^8$, —C(O)N$R^7$C(O)O$R^7$, —C(O)N$R^7$C(O)NH$_2$, —C(O)N$R^7$C(O)N($R^7$)$_2$ or H;

each $R^2$ is independently selected from H and $C_1$-$C_6$alkyl;

each $R^3$ is independently selected from H, $C_1$-$C_6$alkyl, —CN, —C(O)N($R^7$)$_2$, —$OR^7$ and halo, or the two $R^3$ together with the C atom they are attached form a cyclopropyl group spiro attached to the pyrrolidine;

or a $R^2$ and a $R^3$ together with the C atom they are attached form a cyclopropyl ring fused to the pyrrolidine;

each $R^4$ is independently selected from H, halo, —$OR^7$, $C_1$-$C_6$alkyl, $C_1$-$C_6$alkyl substituted with 1-3 halo, $C_1$-$C_6$alkoxy substituted with 1-3 halo, —CN and —$C(O)N(R^7)_2$;

each $R^5$ is independently selected from H and $C_1$-$C_6$alkyl;

each $R^6$ is independently selected from H, $C_1$-$C_6$alkyl, —CN, —$OR^7$ and halo;

each $R^7$ is independently selected from H, $C_1$-$C_6$alkyl or $C_1$-$C_6$alkyl substituted with 1-3 —OH;

each $R^8$ is independently selected from H, $C_1$-$C_6$alkyl, phenyl, benzyl, phenyl substituted with 1-3 groups independently selected from $R^6$, benzyl substituted with 1-3 groups independently selected from $R^6$, an unsubstituted 5-6 membered heterocycloalkyl having 1 to 2 heteroatoms independently selected from O and N, a 5-6 membered heterocycloalkyl having 1 to 2 heteroatoms independently selected from O and N which is substituted with 1-3 groups independently selected from $R^6$, an unsubstituted $C_3$-$C_6$cycloalkyl, a $C_3$-$C_6$cycloalkyl substituted with 1-3 groups independently selected from $R^6$, an unsubstituted 5-6 membered heteroaryl having 1 to 2 heteroatoms independently selected from O and N, a 5-6 membered heteroaryl having 1 to 2 heteroatoms independently selected from O and N which is substituted with 1-3 groups independently selected from $R^6$;

each $R^9$ is a $C_1$-$C_6$alkyl and together with the N atom they are attached form an unsubstituted 5-6 membered heterocycloalkyl or a 5-6 membered heterocycloalkyl substituted with 1-3 groups independently selected from $R^6$;

m is 0, 1, 2, 3 or 4, n is 0, 1 or 2, or a pharmaceutically acceptable salt thereof.

2. The compound of claim 1, wherein:

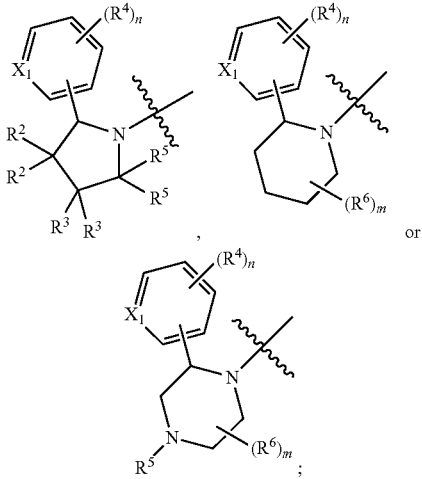

A is $X_1$ is CH or N;

$R^1$ is —$C(O)NH_2$, —$C(O)N(R^7)_2$, —$C(O)N(R^8)_2$, —$NR^7C(O)R^8$, —$NR^7C(O)N(R^7)_2$, —$NR^7C(O)N(R^8)_2$, —$NR^7C(O)N(R^9)_2$; —$C(O)OR^7$, —$NR^7C(O)OR^7$, —$C(O)NR^7C(O)OR^7$, —$C(O)NR^7C(O)NH_2$, —$C(O)NR^7C(O)N(R^7)_2$ or H;

each $R^2$ is independently selected from H and $C_1$-$C_6$alkyl;

each $R^3$ is independently selected from H, $C_1$-$C_6$alkyl, —CN, —$OR^7$ and halo, or the two $R^3$ together with the C atom they are attached form a cyclopropyl group spiro attached to the pyrrolidine;

or a $R^2$ and a $R^3$ together with the C atom they are attached form a cyclopropyl ring fused to the pyrrolidine;

each $R^4$ is independently selected from H, halo, —$OR^7$, $C_1$-$C_6$alkyl, $C_1$-$C_6$alkyl substituted with 1-3 halo, $C_1$-$C_6$alkoxy substituted with 1-3 halo, —CN and —$C(O)N(R^7)_2$;

each $R^5$ is independently selected from H and $C_1$-$C_6$alkyl;

each $R^6$ is independently selected from H, $C_1$-$C_6$alkyl, —CN, —$OR^7$ and halo;

each $R^7$ is independently selected from H, $C_1$-$C_6$alkyl or $C_1$-$C_6$alkyl substituted with 1-3 —OH;

each $R^8$ is independently selected from H, $C_1$-$C_6$alkyl, phenyl, phenyl substituted with 1-3 groups independently selected from $R^6$, an unsubstituted 5-6 membered heterocycloalkyl having 1 to 2 heteroatoms independently selected from O and N, a 5-6 membered heterocycloalkyl having 1 to 2 heteroatoms independently selected from O and N which is substituted with 1-3 groups independently selected from $R^6$, an unsubstituted $C_3$-$C_6$cycloalkyl, a $C_3$-$C_6$cycloalkyl substituted with 1-3 groups independently selected from $R^6$, an unsubstituted 5-6 membered heteroaryl having 1 to 2 heteroatoms independently selected from O and N, a 5-6 membered heteroaryl having 1 to 2 heteroatoms independently selected from O and N which is substituted with 1-3 groups independently selected from $R^6$;

each $R^9$ is a $C_1$-$C_6$alkyl and together with the N atom they are attached form an unsubstituted 5-6 membered heterocycloalkyl or a 5-6 membered heterocycloalkyl substituted with 1-3 groups independently selected from $R^6$;

m is 0, 1, 2, 3 or 4, n is 0, 1 or 2, or a pharmaceutically acceptable salt thereof.

3. The compound of claim 1, wherein the compound of Formula (I) is a compound having the structure of Formula (II):

Formula (II)

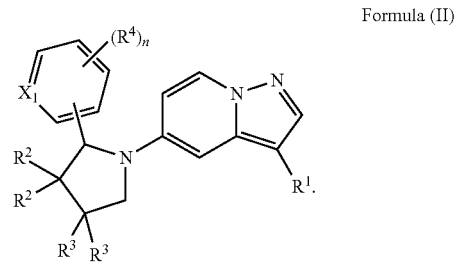

4. The compound of claim 3, wherein the compound of Formula (II) is a compound having the structure of Formula (II-a) or Formula (II-b):

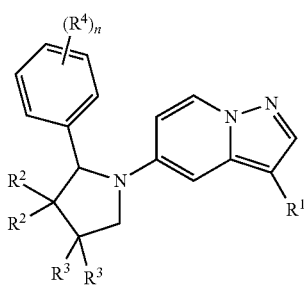

Formula (II-a)

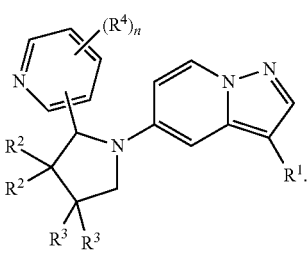

Formula (II-b)

5. The compound of claim 4, wherein the compound of Formula (II-a) is a compound having the structure of Formula (II-c):

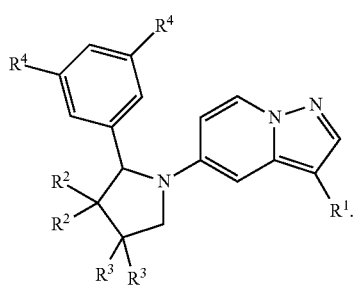

Formula (II-c)

6. The compound of claim 5, wherein each $R^4$ is independently selected from H, F, —CN, —C(O)NH$_2$, —OCF$_3$, —OCHF$_2$ and —OCH$_2$F.

7. The compound of claim 6, wherein each $R^3$ is independently selected from H, —CN, —C(O)NH$_2$ and F, and wherein each $R^2$ is H.

8. The compound of claim 7, wherein each $R^3$ is independently selected from H and F, and wherein each $R^2$ is H.

9. The compound of claim 8, wherein $R^1$ is —C(O)NH$_2$, —C(O)N(R$^7$)$_2$ or —C(O)OR$^7$, wherein each $R^7$ is independently selected from H, methyl and ethyl.

10. The compound of claim 9, wherein $R^1$ is —C(O)NH$_2$.

11. The compound of claim 1 selected from:
5-((2R,4S)-2-(3-cyano-5-fluorophenyl)-4-fluoropyrrolidin-1-yl)pyrazolo[1,5-a]pyridine-3-carboxamide;
ethyl 5-((2R,4S)-4-fluoro-2-(3-fluorophenyl)pyrrolidin-1-yl)pyrazolo[1,5-a]pyridine-3-carboxylate;
(R)-ethyl 5-(4,4-difluoro-2-(3-fluorophenyl)pyrrolidin-1-yl)pyrazolo[1,5-a]pyridine-3-carboxylate;
5-((2R,4S)-4-fluoro-2-(3-fluorophenyl)pyrrolidin-1-yl)pyrazolo[1,5-a]pyridine-3-carboxylic acid;
(R)-5-(4,4-difluoro-2-(3-fluorophenyl)pyrrolidin-1-yl)pyrazolo[1,5-a]pyridine-3-carboxylic acid;
5-((2R,4S)-4-fluoro-2-(3-fluorophenyl)pyrrolidin-1-yl)pyrazolo[1,5-a]pyridine-3-carboxamide;
(R)-5-(4,4-difluoro-2-(3-fluorophenyl)pyrrolidin-1-yl)pyrazolo[1,5-a]pyridine-3-carboxamide;
ethyl 5-((2R,4S)-2-(3-cyano-5-fluorophenyl)-4-fluoropyrrolidin-1-yl)pyrazolo[1,5-a]pyridine-3-carboxylate;
(R)-ethyl 5-(2-(3-cyano-5-fluorophenyl)-4,4-difluoropyrrolidin-1-yl)pyrazolo[1,5-a]pyridine-3-carboxylate;
(R)-5-(2-(3-carbamoyl-5-fluorophenyl)-4,4-difluoropyrrolidin-1-yl)pyrazolo[1,5-a]pyridine -3-carboxamide, and
(R)-5-(2-(3-cyano-5-fluorophenyl)-4,4-difluoropyrrolidin-1-yl)pyrazolo[1,5-a]pyridine-3-carboxamide.

12. The compound of claim 1 selected from:
5-[2-(3-fluorophenyl)piperidin-1-yl]pyrazolo[1,5-a]pyridine-3-carboxamide
5-{2-[2-(trifluoromethyl)phenyl]pyrrolidin-1-yl}pyrazolo[1,5-a]pyridine-3-carboxamide;
N-ethyl-5-[(2R,4S)-4-fluoro-2-(3-fluorophenyl)pyrrolidin-1-yl]pyrazolo[1,5-a]pyridine-3-carboxamide;
5-[(2R,4S)-4-fluoro-2-(3-fluorophenyl)pyrrolidin-1-yl]-N,N-dimethylpyrazolo[1,5-a]pyridine-3-carboxamide;
N-tert-butyl-5-[(2R,4S)-4-fluoro-2-(3-fluorophenyl)pyrrolidin-1-yl]pyrazolo[1,5-a]pyridine-3-carboxamide;
5-[(2R,4S)-4-fluoro-2-(3-fluorophenyl)pyrrolidin-1-yl]-N-(2-hydroxyethyl)pyrazolo[1,5-a]pyridine-3-carboxamide;
5-(4,4-difluoro-2-{5-fluoro-2-[(propan-2-yl)carbamoyl]phenyl}pyrrolidin-1-yl)pyrazolo[1,5-a]pyridine-3-carboxamide;
ethyl 5-[(2R,4S)-4-cyano-2-(3-fluorophenyl)pyrrolidin-1-yl]pyrazolo[1,5-a]pyridine-3-carboxylate;
ethyl 5-[(2R,4S)-4-carbamoyl-2-(3-fluorophenyl)pyrrolidin-1-yl]pyrazolo[1,5-a]pyridine-3-carboxylate;
benzyl N-{5-[(2R,4S)-4-fluoro-2-(3-fluorophenyl)pyrrolidin-1-yl]pyrazolo[1,5-a]pyridin-3-yl}carbamate;
5-[(2R,4S)-4-fluoro-2-(3-fluorophenyl)pyrrolidin-1-yl]-N-phenylpyrazolo[1,5-a]pyridine-3-carboxamide;
{-[(2R,4S)-4-fluoro-2-(3-fluorophenyl)pyrrolidin-1-yl]pyrazolo[1,5-a]pyridin-3-yl}urea;
5-[(2R,4R)-2-(3-fluorophenyl)-4-hydroxypyrrolidin-1-yl]pyrazolo[1,5-a]pyridine-3-carboxamide;
5-[(2R,4S)-4-cyano-2-(3-fluorophenyl)pyrrolidin-1-yl]pyrazolo[1,5-a]pyridine-3-carboxamide, and
(3S,5R)-1-{3-carbamoylpyrazolo[1,5-a]pyridin-5-yl}-5-(3-fluorophenyl)pyrrolidine-3-carboxamide.

13. The compound of claim 1 selected from:
5-((2R,4S)-2-(3-cyano-5-fluorophenyl)-4-fluoropyrrolidin-1-yl)pyrazolo[1,5-a]pyridine-3-carboxamide.

14. The compound of claim 1 selected from:
N-ethyl-5-[(2R,4S)-4-fluoro-2-(3-fluorophenyl)pyrrolidin-1-yl]pyrazolo[1,5-a]pyridine-3-carboxamide.

15. The compound of claim 1 selected from:
ethyl 5-[(2R,4S)-4-cyano-2-(3-fluorophenyl)pyrrolidin-1-yl]pyrazolo[1,5-a]pyridine-3-carboxylate.

16. The compound of claim 1 selected from:
ethyl 5-[(2R,4S)-4-carbamoyl-2-(3-fluorophenyl)pyrrolidin-1-yl]pyrazolo[1,5-a]pyridine-3-carboxylate.

17. A pharmaceutical composition comprising a therapeutically effective amount of a compound of claim 1 and a pharmaceutically acceptable carrier.

18. A pharmaceutical composition comprising a therapeutically effective amount of a compound of claim 11 and a pharmaceutically acceptable carrier.

19. A pharmaceutical composition comprising a therapeutically effective amount of a compound of claim 12 and a pharmaceutically acceptable carrier.

* * * * *